(12) United States Patent
Mukerji et al.

(10) Patent No.: US 6,287,866 B1
(45) Date of Patent: *Sep. 11, 2001

(54) β-CASEIN EXPRESSING CONSTRUCTS

(75) Inventors: Pradip Mukerji, Gahanna; Steven A. Lemmel, Columbus; Amanda Eun-Yeong Leonard, Gahannna, all of OH (US); Sunita Chaudhary, Pearland, TX (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/131,028

(22) Filed: Aug. 7, 1998

Related U.S. Application Data

(60) Continuation-in-part of application No. 09/064,440, filed on Apr. 22, 1998, now abandoned, which is a division of application No. 08/757,177, filed on Nov. 27, 1996, now Pat. No. 6,071,718.

(51) Int. Cl.⁷ .................................................. C12N 15/74
(52) U.S. Cl. ..................... 435/488; 435/471; 435/252.33
(58) Field of Search ............................ 435/69.1, 252.33, 435/325, 320.1, 488, 471; 536/23.1, 23.5, 23.2

(56) References Cited

U.S. PATENT DOCUMENTS

| 4,543,329 | 9/1985 | Daum et al. ......................... 435/69.1 |
| 5,013,662 | 5/1991 | Ben-Bassat et al. .................... 435/212 |
| 5,506,209 | 4/1996 | Mukerji et al. ........................ 514/21 |
| 5,538,952 | 7/1996 | Mukerji ................................... 514/12 |
| 5,710,044 | * 1/1998 | Mukerji et al. .................... 435/320.1 |
| 5,773,273 | * 6/1998 | Nishino et al. ...................... 435/193 |
| 5,807,702 | * 9/1998 | Mukerji et al. ...................... 435/69.1 |

FOREIGN PATENT DOCUMENTS

| 32536 | 12/1989 | (AU) . |
| 37170 | 4/1990 | (AU) . |
| 0348780 | 1/1990 | (EP) . |
| 9627017 | 9/1996 | (WO) . |
| 9627018 | 9/1996 | (WO) . |
| 9823762 | 6/1998 | (WO) . |

OTHER PUBLICATIONS

Greenberg et al., *Journal of Biological Chemistry*, 259:5132–38.

Hanson et al,. *Protein Expression and Purification*, 4:373–381 (1993).

A. B–Bassat et al., *Journal of Bacteriology*, 169:751–757 (1987).

Lingappa et al., *Proceeding of the National Academy of Science USA*, 74:2432–2436 (1977).

Hitzeman et al., *Science*, 219:620–25 (1983).

Klein et al., *Microbiology* (1994) 140, 1133–1139.

Leenhouts et al., *Applied and Environmental Microbiology*, 55:2, 394–400 (1989).

Johnson et al., *Bio/Technology*, 12:1357–1360 (1994).

Mayo et al., "Applied and Environmental Microbiology" Jan. 1991 p. 38–44.

A B–Bassat et al., *Purification and Analysis of Recombinant Proteins* eds. Seetharam and Sharma, pp. 147–159, Marcel Dekker Inc., N.Y. (1991).

J. M. Thurmond et al., "Expression And Characterization Of Phosphorylated Recombinant Human B–Casein In*Escherichia Coli*"—Vol. 10, 1997, pp. 202–208, Protein Expression and Purication.

Shen T.–J. et al., *Proceedings of the National Academy of Sciences of USA*, vol. 90, Sep. 1993, pp. 8108–8112— XP002058672.

Sabin E. A. et al., "High –Level Expression And In Vivo Processing of Chimeric Ubiquitin Fusion Proteins In*Saccharomyces Cerevisiae*", vol. 7, No. 7, Jul. 1989, pp. 705–709, XP000034178.

* cited by examiner

*Primary Examiner*—Nashaat T. Nashed
(74) *Attorney, Agent, or Firm*—Cheryl L. Becker

(57) ABSTRACT

The subject invention relates to β-casein expressing constructs which have significant stability when introduced into host cells. These constructs, for purposes of the present invention, have been designated as pRAB-84-69 and pRSB-14. Each construct comprises an isolated DNA sequence comprising i) a nucleotide sequence encoding a protein, wherein said nucleotide sequence is operably linked to a promoter, ii) a nucleotide sequence encoding a first subunit of a kinase, iii) a nucleotide sequence encoding a second subunit of a kinase, iv) a nucleotide encoding a peptidase and v) a nucleotide sequence encoding a bacterial resistance marker. These constructs, once introduced into a host cell, may be used in the production of, for example, recombinant human beta-casein.

1 Claim, 54 Drawing Sheets

Lane 1: LMW marker
Lane 2: 20 ng of rHBCN
Lane 3: lys of HMS174(DE3)(pRJB-36)
Lane 4: lys of HMS174(DE3)(pRAB-84-69)

Lane 1: LMW marker
Lane 2: 20 ng of rHBCN
Lane 3: lys of HMS174(DE3)(pRJB-36)
Lane 4: lys of HMS174(DE3)(pRSB-14)

```
            10          20          30          40
       *     *     *     *     *     *     *     *
      TCGAC CTA GTC CTG GCT GAT TAA CCA GTC AGA CAA CAG CTC TTG
      AGCTG GAT CAG GAC CGA CTA ATT GGT CAG TCT GTT GTC GAG AAC
           <*** Asp Gln Ser Ile Leu Trp Asp Ser Leu Leu Glu Gln
           <__o__o__o__o__o__PEPI__o__o__o__o__o__

50          60          70          80
       *     *     *     *     *     *     *     *     *
      ATA CTT GGC ATT TTC CTG GAC AAA AGG CAT GTG GCC GCA GCC GGC
      TAT GAA CCG TAA AAG GAC CTG TTT TCC GTA CAC CGG CGT CGG CCG
      <Tyr Lys Ala Asn Glu Gln Val Phe Pro Met His Gly Cys Gly Ala
      <__o__o__o__o__o__o__PEPI__o__o__o__o__o__o__

90         100         110         120         130
       *     *     *     *     *     *     *     *     *
      AAA GAG CTC CCA GCG GGC ATT TGG CAA GTG ATC GTA CAT GCT TTT
      TTT CTC GAG GGT CGC CCG TAA ACC GTT CAC TAG CAT GTA CGA AAA
      <Phe Leu Glu Trp Arg Ala Asn Pro Leu His Asp Tyr Met Ser Lys
      <__o__o__o__o__o__o__PEPI__o__o__o__o__o__o__

140         150         160         170
       *     *     *     *     *     *     *     *     *
      AGC CAC TAG GGG AGT GCA CAA GTC GTC AGT GCC GCT GGT AAT CAA
      TCG GTG ATC CCC TCA CGT GTT CAG CAG TCA CGG CGA CCA TTA GTT
      <Ala Val Leu Pro Thr Cys Leu Asp Asp Thr Gly Ser Thr Ile Leu
      <__o__o__o__o__o__o__PEPI__o__o__o__o__o__o__

180         190         200         210         220
       *     *     *     *     *     *     *     *     *
      GGC CGG CAA GTC CAG GTC CTT TAA GCG GTC AGT GTA CTC ATA GCC
      CCG GCC GTT CAG GTC CAG GAA ATT CGC CAG TCA CAT GAG TAT CGG
      <Ala Pro Leu Asp Leu Asp Lys Leu Arg Asp Thr Tyr Glu Tyr Gly
      <__o__o__o__o__o__o__PEPI__o__o__o__o__o__o__

230         240         250         260
       *     *     *     *     *     *     *     *     *
      GTG CAG GTT GCC AAT CGG CGT ATA TTC ATT AGG GCC CCA GCC TGT
      CAC GTC CAA CGG TTA GCC GCA TAT AAG TAA TCC CGG GGT CGG ACA
      <His Leu Asn Gly Ile Pro Thr Tyr Glu Asn Pro Gly Trp Gly Thr
      <__o__o__o__o__o__o__PEPI__o__o__o__o__o__o__
```

FIG. 7A

```
        270         280         290         300         310
         *    *      *    *      *    *      *    *      *
       CAA GTA GGC CAG GTT GCC GCC CTT TTT TTT GCG CAA AAC TGG CTC
       GTT CAT CCG GTC CAA CGG CGG GAA AAA AAA CGC GTT TTG ACC GAG
       <Leu Tyr Ala Leu Asn Gly Gly Lys Lys Lys Arg Leu Val Pro Glu
       <___a___a___a___a___a___a__PEPI___a___a___a___a___a___a___

320         330         340         350
                *    *      *    *      *    *      *    *
       CGG CAG GTC CGG CGT AAG CTT GAT GGC GTG CTG GTC CAT GAA GTG
       GCC GTC CAG GCC GCA TTC GAA CTA CCG CAC GAC CAG GTA CTT CAC
       <Pro Leu Asp Pro Thr Leu Lys Ile Ala His Gln Asp Met Phe His
       <___a___a___a___a___a___a__PEPI___a___a___a___a___a___a___

360         370         380         390         400
          *    *      *    *      *    *      *    *      *
       GGC ATT GGC CGC CTG GTA GGC CGG GGA GTC GTA GTT GCC AGT TGT
       CCG TAA CCG GCG GAC CAT CCG GCC CCT CAG CAT CAA CGG TCA ACA
       <Ala Asn Ala Ala Gln Tyr Ala Pro Ser Asp Tyr Asn Gly Thr Thr
       <___a___a___a___a___a___a__PEPI___a___a___a___a___a___a___

410         420         430         440
                *    *      *    *      *    *      *    *
       TTC AGC TTC CTT GAT AGC GGC CTG CTC GCC CTT GGG CAG GTA CTT
       AAG TCG AAG GAA CTA TCG CCG GAC GAG CGG GAA CCC GTC CAT GAA
       <Glu Ala Glu Lys Ile Ala Ala Gln Glu Gly Lys Pro Leu Tyr Lys
       <___a___a___a___a___a___a__PEPI___a___a___a___a___a___a___

450         460         470         480         490
          *    *      *    *      *    *      *    *      *
       GAT CAA GCG GTG CAG TTC CTG GCT CCA AAG CTT GGC GGA GGC TAA
       CTA GTT CGC CAC GTC AAG GAC CGA GGT TTC GAA CCG CCT CCG ATT
       <Ile Leu Arg His Leu Glu Gln Ser Trp Leu Lys Ala Ser Ala Leu
       <___a___a___a___a___a___a__PEPI___a___a___a___a___a___a___

500         510         520         530
                *    *      *    *      *    *      *    *
       AGT GGA GGA GAG GAT CAG GCT CTT GAC CCC TTT AGG CTG GTA GTC
       TCA CCT CCT CTC CTA GTC CGA GAA CTG GGG AAA TCC GAC CAT CAG
       <Thr Ser Ser Leu Ile Leu Ser Lys Val Gly Lys Pro Gln Tyr Asp
       <___a___a___a___a___a___a__PEPI___a___a___a___a___a___a___
```

FIG. 7B

```
        540         550         560         570         580
         *     *     *     *     *     *     *     *     *
      GCA CAG GTA GAT CAA AGC CAG CAT CCC GCC CCA GCT TTG CCC CAA
      CGT GTC CAT CTA GTT TCG GTC GTA GGG CGG GGT CGA AAC GGG GTT
     <Cys Leu Tyr Ile Leu Ala Leu Met Gly Gly Trp Ser Gln Gly Leu
     <___o___o___o___o___o___o__PEPI___o___o___o___o___o___o__

590         600         610         620
               *     *     *     *     *     *     *     *     *
      AAG GTG GAT CTG GTC AAG GCC CAG CTG CTC TCT GAC ATT TTC CAG
      TTC CAC CTA GAC CAG TTC CGG GTC GAC GAG AGA CTG TAA AAG GTC
     <Leu His Ile Gln Asp Leu Gly Leu Gln Glu Arg Val Asn Glu Leu
     <___o___o___o___o___o___o__PEPI___o___o___o___o___o___o__

630         640         650         660         670
         *     *     *     *     *     *     *     *     *
      CTC CTT GAC CCA GGT TTG GGC CGT GTA GGC TGT TTC CGC CTG GTC
      GAG GAA CTG GGT CCA AAC CCG GCA CAT CCG ACA AAG GCG GAC CAG
     <Glu Lys Val Trp Thr Gln Ala Thr Tyr Ala Thr Glu Ala Gln Asp
     <___o___o___o___o___o___o__PEPI___o___o___o___o___o___o__

680         690         700         710
               *     *     *     *     *     *     *     *     *
      GTC GGG GAT GCT GGA GTT GCC GCA GCC TAA TTG GTC ATA CAT GAT
      CAG CCC CTA CGA CCT CAA CGG CGT CGG ATT AAC CAG TAT GTA CTA
     <Asp Pro Ile Ser Ser Asn Gly Cys Gly Leu Gln Asp Tyr Met Ile
     <___o___o___o___o___o___o__PEPI___o___o___o___o___o___o__

720         730         740         750         760
         *     *     *     *     *     *     *     *     *
      GAC CTG GCG GCC GCT TTT TTC AGC GAC TTG GTC GAG GAC TTC AAA
      CTG GAC CGC CGG CGA AAA AAG TCG CTG AAC CAG CTC CTG AAG TTT
     <Val Gln Arg Gly Ser Lys Glu Ala Val Gln Asp Leu Val Glu Phe
     <___o___o___o___o___o___o__PEPI___o___o___o___o___o___o__

770         780         790         800
               *     *     *     *     *     *     *     *     *
      ATA GTT GTG ACT GCT GCC GGG CCC GCC GTG GAG AAG GAG GAG CGG
      TAT CAA CAC TGA CGA CGG CCC GGG CGG CAC CTC TTC CTC CTC GCC
     <Tyr Asn His Ser Ser Gly Pro Gly Gly His Leu Leu Leu Leu Pro
     <___o___o___o___o___o___o__PEPI___o___o___o___o___o___o__
```

FIG. 7C

```
        810         820         830         840         850
         *     *     *     *     *     *     *     *     *
        GGC GCG GTC AGT AGC CTC GCC CAC GAT CCG GCA GTA GGT TTG CCA
        CCG CGC CAG TCA TCG GAG CGG GTG CTA GGC CGT CAT CCA AAC GGT
        <Ala Arg Asp Thr Ala Glu Gly Val Ile Trp Cys Tyr Thr Gln Trp
        <__a__a__a__a__a__a__PEP1___a__a__a__a__a__a__

860         870         880         890         900
         *     *     *     *     *     *     *     *     *    *
        ATT TCC AAA TGG AAG ATA TTT TTC TGT GAT TTG CAT CTTGAATTGA
        TAA AGG TTT ACC TTC TAT AAA AAG ACA CTA AAC GTA GAACTTAACT
        <Asn Gly Phe Pro Leu Tyr Lys Glu Thr Ile Gln Met
        <__a__a__a__a__a_PEP1__a__a__a__a__a__

910         920         930         940         950
             *     *     *     *     *     *     *     *     *
        TCCCCGGGAA TTCTGTTTCC TGTGTGAAAT TGTTATCCGC TCACAATTCC
        AGGGGCCCTT AAGACAAAGG ACACACTTTA ACAATAGGCG AGTGTTAAGG
                  <_____b_____PTAC_____b_____

960         970         980         990        1000
             *     *     *     *     *     *     *     *     *    *
        ACACATTATA CGAGCCGATG ATTAATTGTC AACAGCTCAT TTCAGAATAT
        TGTGTAATAT GCTCGGCTAC TAATTAACAG TTGTCGAGTA AAGTCTTATA
        <_____b_PTAC____b_____

1010        1020        1030        1040        1050
             *     *     *     *     *     *     *     *     *    *
        TTGCCAGAAC CGTTATGATG TCGGCGCAAA AAACATTATC CAGAACGGGA
        AACGGTCTTG GCAATACTAC AGCCGCGTTT TTTGTAATAG GTCTTGCCCT 1060        1070        1080        1090        1100
             *     *     *     *     *     *     *     *     *    *
        GTGCGCCTTG AGCGACACGA ATTATGCAGT GATTTACGAC CTGCACAGCC
        CACGCGGAAC TCGCTGTGCT TAATACGTCA CTAAATGCTG GACGTGTCGG 1110        1120        1130        1140        1150
             *     *     *     *     *     *     *     *     *    *
        ATACCACAGC TTCCGATGGC TGCCTGACGC CAGAAGCATT GGTGCACCGT
        TATGGTGTCG AAGGCTACCG ACGGACTGCG GTCTTCGTAA CCACGTGGCA
```

FIG. 7D

```
          1160       1170       1180       1190       1200
           *  *       *  *       *  *       *  *       *  *
      GCAGTCGATA AGCCCGGATC AATTCGGATC GCTTCACGAC CACGCTGATG
      CGTCAGCTAT TCGGGCCTAG TTAAGCCTAG CGAAGTGCTG GTGCGACTAC 1210       1220       1230       1240       1250
           *  *       *  *       *  *       *  *       *  *
      AGCTTTACCG CAGCTGCCTC GCGCGTTTCG GTGATGACGG TGAAAACCTC
      TCGAAATGGC GTCGACGGAG CGCGCAAAGC CACTACTGCC ACTTTTGGAG 1260       1270       1280       1290       1300
           *  *       *  *       *  *       *  *       *  *
      TGACACATGC AGCTCCCGGA GACGGTCACA GCTTGTCTGT AAGCGGATGC
      ACTGTGTACG TCGAGGGCCT CTGCCAGTGT CGAACAGACA TTCGCCTACG 1310       1320       1330       1340       1350
           *  *       *  *       *  *       *  *       *  *
      CGGGAGCAGA CAAGCCCGTC AGGGCGCGTC AGCGGGTGTT GGCGGGTGTC
      GCCCTCGTCT GTTCGGGCAG TCCCGCGCAG TCGCCCACAA CCGCCCACAG 1360       1370       1380       1390       1400
           *  *       *  *       *  *       *  *       *  *
      GGGGCGCAGC CATGACCCAG TCACGTAGCG ATAGCGGAGT GTACGAACGC
      CCCCGCGTCG GTACTGGGTC AGTGCATCGC TATCGCCTCA CATGCTTGCG 1410       1420       1430       1440       1450
           *  *       *  *       *  *       *  *       *  *
      CAGCAAGACG TAGCCCAGCG CGTCGGCCGC CATGCCGGCG ATAATGGCCT
      GTCGTTCTGC ATCGGGTCGC GCAGCCGGCG GTACGGCCGC TATTACCGGA 1460       1470       1480       1490       1500
           *  *       *  *       *  *       *  *       *  *
      GCTTCTCGCC GAAACGTTTG GTGGCGGGAC CAGTGACGAA GGCTTGAGCG
      CGAAGAGCGG CTTTGCAAAC CACCGCCCTG GTCACTGCTT CCGAACTCGC 1510       1520       1530       1540       1550
           *  *       *  *       *  *       *  *       *  *
      AGGGCGTGCA AGATTCCGAA TACCGCAAGC GACAGGCCGA TCATCGTCGC
      TCCCGCACGT TCTAAGGCTT ATGGCGTTCG CTGTCCGGCT AGTAGCAGCG 1560       1570       1580       1590       1600
           *  *       *  *       *  *       *  *       *  *
      GCTCCAGCGA AAGCGGTCCT CGCCGAAAAT GACCCAGAGC GCTGCCGGCA
      CGAGGTCGCT TTCGCCAGGA GCGGCTTTTA CTGGGTCTCG CGACGGCCGT
```

FIG. 7E

```
        1610       1620       1630       1640       1650
         *  *       *  *       *  *       *  *       *  *
     CCTGTCCTAC GAGTTGCATG ATAAAGAAGA CAGTCATAAG TGCGGCGACG
     GGACAGGATG CTCAACGTAC TATTTCTTCT GTCAGTATTC ACGCCGCTGC 1660       1670       1680       1690       1700
         *  *       *  *       *  *       *  *       *  *
     ATAGTCATGC CCCGCGCCCA CCGGAAGGAG CTGACTGGGT TGAAGGCTCT
     TATCAGTACG GGGCGCGGGT GGCCTTCCTC GACTGACCCA ACTTCCGAGA 1710       1720       1730       1740       1750
         *  *       *  *       *  *       *  *       *  *
     CAAGGGCATC GGTCGACGCT CTCCCTTATG CGACTCCTGC ATTAGGAAGC
     GTTCCCGTAG CCAGCTGCGA GAGGGAATAC GCTGAGGACG TAATCCTTCG 1760       1770       1780       1790       1800
         *  *       *  *       *  *       *  *       *  *
     AGCCCAGTAG TAGGTTGAGG CCGTTGAGCA CCGCCGCCGC AAGGAATGGT
     TCGGGTCATC ATCCAACTCC GGCAACTCGT GGCGGCGGCG TTCCTTACCA 1810       1820       1830       1840       1850
         *  *       *  *       *  *       *  *       *  *
     GCATGCAAGG AGATGGCGCC CAACAGTCCC CCGGCCACGG GGCCTGCCAC
     CGTACGTTCC TCTACCGCGG GTTGTCAGGG GGCCGGTGCC CCGGACGGTG 1860       1870       1880       1890       1900
         *  *       *  *       *  *       *  *       *  *
     CATACCCACG CCGAAACAAG CGCTCATGAG CCCGAAGTGG CGAGCCCGAT
     GTATGGGTGC GGCTTTGTTC GCGAGTACTC GGGCTTCACC GCTCGGGCTA 1910       1920       1930       1940       1950
         *  *       *  *       *  *       *  *       *  *
     CTTCCCCATC GGTGATGTCG GCGATATAGG CGCCAGCAAC CGCACCTGTG
     GAAGGGGTAG CCACTACAGC CGCTATATCC GCGGTCGTTG GCGTGGACAC 1960       1970       1980       1990       2000
         *  *       *  *       *  *       *  *       *  *
     GCGCCGGTGA TGCCGGCCAC GATGCGTCCG GCGTAGAGGA TCGAGATCTC
     CGCGGCCACT ACGGCCGGTG CTACGCAGGC CGCATCTCCT AGCTCTAGAG 2010       2020       2030       2040       2050
         *  *       *  *       *  *       *  *       *  *
     GATCCCGCGA AATTAATACG ACTCACTATA GGGAGACCAC AACGGTTTCC
     CTAGGGCGCT TTAATTATGC TGAGTGATAT CCCTCTGGTG TTGCCAAAGG
                         ___T7 PROMOTER___e_>
```

FIG. 7F

```
          2060        2070        2080        2090        2100
            *           *           *           *           *
       CTCTAGAAAT  AATTTTGTTT  AACTTTAAGA  AGGAGATATA  CAT ATG CCG CGT
       GAGATCTTTA  TTAAAACAAA  TTGAAATTCT  TCCTCTATAT  GTA TAC GGC GCA
                                                          Met Pro Arg>
                                                          __f__f__>

2110        2120        2130        2140
            *           *           *           *
       GAA ACC ATC GAA TCC CTG AGC TCG AGC GAA GAA TCG ATC ACC GAA
       CTT TGG TAG CTT AGG GAC TCG AGC TCG CTT CTT AGC TAG TGG CTT
       Glu Thr Ile Glu Ser Leu Ser Ser Ser Glu Glu Ser Ile Thr Glu>
       __f__f__f__f__f__f__HBCN__f__f__f__f__f__f__>

2150        2160        2170        2180        2190
          *           *           *           *           *
       TAC AAA CAG AAA GTT GAA AAA GTT AAA CAC GAG GAC CAG CAG CAA
       ATG TTT GTC TTT CAA CTT TTT CAA TTT GTG CTC CTG GTC GTC GTT
       Tyr Lys Gln Lys Val Glu Lys Val Lys His Glu Asp Gln Gln Gln>
       __f__f__f__f__f__f__HBCN__f__f__f__f__f__f__>

2200        2210        2220        2230
            *           *           *           *
       GGA GAG GAT GAA CAC CAG GAT AAA ATC TAC CCC TCT TTC CAG CCA
       CCT CTC CTA CTT GTG GTC CTA TTT TAG ATG GGG AGA AAG GTC GGT
       Gly Glu Asp Glu His Gln Asp Lys Ile Tyr Pro Ser Phe Gln Pro>
       __f__f__f__f__f__f__HBCN__f__f__f__f__f__f__>

2240        2250        2260        2270        2280
            *           *           *           *           *
       CAG CCT CTG ATC TAT CCA TTC GTT GAA CCT ATC CCC TAT GGT TTT
       GTC GGA GAC TAG ATA GGT AAG CAA CTT GGA TAG GGG ATA CCA AAA
       Gln Pro Leu Ile Tyr Pro Phe Val Glu Pro Ile Pro Tyr Gly Phe>
       __f__f__f__f__f__f__HBCN__f__f__f__f__f__f__>

2290        2300        2310        2320
            *           *           *           *
       CTT CCA CAA AAC ATT CTG CCT CTT GCT CAG CCT GCT GTG GTG CTG
       GAA GGT GTT TTG TAA GAC GGA GAA CGA GTC GGA CGA CAC CAC GAC
       Leu Pro Gln Asn Ile Leu Pro Leu Ala Gln Pro Ala Val Val Leu>
       __f__f__f__f__f__f__HBCN__f__f__f__f__f__f__>
```

FIG. 7G

```
          2330        2340        2350        2360        2370
            *           *           *           *           *
      CCT GTC CCT CAG CCT GAA ATA ATG GAA GTC CCT AAA GCT AAA GAC
      GGA CAG GGA GTC GGA CTT TAT TAC CTT CAG GGA TTT CGA TTT CTG
      Pro Val Pro Gln Pro Glu Ile Met Glu Val Pro Lys Ala Lys Asp>
      __f___f___f___f___f___f___HBCN___f___f___f___f___f___f___>

2380        2390        2400        2410
                *           *           *           *           *
      ACT GTC TAC ACT AAG GGC AGA GTG ATG CCT GTC CTT AAA TCT CCA
      TGA CAG ATG TGA TTC CCG TCT CAC TAC GGA CAG GAA TTT AGA GGT
      Thr Val Tyr Thr Lys Gly Arg Val Met Pro Val Leu Lys Ser Pro>
      __f___f___f___f___f___f___HBCN___f___f___f___f___f___f___>

2420        2430        2440        2450        2460
           *           *           *           *           *
      ACG ATA CCC TTT TTT GAC CCT CAA ATC CCA AAA CTC ACT GAT CTT
      TGC TAT GGG AAA AAA CTG GGA GTT TAG GGT TTT GAG TGA CTA GAA
      Thr Ile Pro Phe Phe Asp Pro Gln Ile Pro Lys Leu Thr Asp Leu>
      __f___f___f___f___f___f___HBCN___f___f___f___f___f___f___>

2470        2480        2490        2500
                *           *           *           *           *
      GAA AAT CTG CAT CTT CCT CTG CCT CTG CTC CAG CCC TTG ATG CAG
      CTT TTA GAC GTA GAA GGA GAC GGA GAC GAG GTC GGG AAC TAC GTC
      Glu Asn Leu His Leu Pro Leu Pro Leu Leu Gln Pro Leu Met Gln>
      __f___f___f___f___f___f___HBCN___f___f___f___f___f___f___>

2510        2520        2530        2540        2550
           *           *           *           *           *
      CAG GTC CCT CAG CCT ATT CCT CAG ACT CTT GCA CTT CCC CCT CAG
      GTC CAG GGA GTC GGA TAA GGA GTC TGA GAA CGT GAA GGG GGA GTC
      Gln Val Pro Gln Pro Ile Pro Gln Thr Leu Ala Leu Pro Pro Gln>
      __f___f___f___f___f___f___HBCN___f___f___f___f___f___f___>

2560        2570        2580        2590
                *           *           *           *           *
      CCC CTG TGG TCT GTT CCT CAG CCC AAA GTC CTG CCT ATC CCC CAG
      GGG GAC ACC AGA CAA GGA GTC GGG TTT CAG GAC GGA TAG GGG GTC
      Pro Leu Trp Ser Val Pro Gln Pro Lys Val Leu Pro Ile Pro Gln>
      __f___f___f___f___f___f___HBCN___f___f___f___f___f___f___>
```

FIG. 7H

```
           2600        2610        2620        2630        2640
            *     *     *     *     *     *     *     *     *
           CAA GTG GTG CCC TAC CCT CAG AGA GCT GTG CCT GTT CAA GCC CTT
           GTT CAC CAC GGG ATG GGA GTC TCT CGA CAC GGA CAA GTT CGG GAA
           Gln Val Val Pro Tyr Pro Gln Arg Ala Val Pro Val Gln Ala Leu>
           ___f___f___f___f___f___f___HBCN___f___f___f___f___f___f___>

2650        2660        2670        2680
              *     *     *     *     *     *     *     *     *
           CTG CTC AAC CAA GAA CTT CTA CTT AAC CCC ACC CAC CAG ATC TAC
           GAC GAG TTG GTT CTT GAA GAT GAA TTG GGG TGG GTG GTC TAG ATG
           Leu Leu Asn Gln Glu Leu Leu Leu Asn Pro Thr His Gln Ile Tyr>
           ___f___f___f___f___f___f___HBCN___f___f___f___f___f___f___>

2690        2700        2710        2720        2730
            *     *     *     *     *     *     *     *     *
           CCT GTG ACT CAG CCA CTT GCC CCA GTT CAT AAC CCC ATT AGT GTC
           GGA CAC TGA GTC GGT GAA CGG GGT CAA GTA TTG GGG TAA TCA CAG
           Pro Val Thr Gln Pro Leu Ala Pro Val His Asn Pro Ile Ser Val>
           ___f___f___f___f___f___f___HBCN___f___f___f___f___f___f___>

2740        2750        2760        2770        2780
              *     *     *     *     *     *     *     *     *
           TAA TAA GG ATCCGGCTGC TAACAAAGCC CGAAAGGAAG CTGAGTTGGC
           ATT ATT CC TAGGCCGACG ATTGTTTCGG GCTTTCCTTC GACTCAACCG
           *** ***>
           ___f___>

2790        2800        2810        2820        2830
              *     *     *     *     *     *     *     *     *     *
           TGCTGCCACC GCTGAGCAAT AACTAGCATA ACCCCTTGGG GCCTCTAAAC
           ACGACGGTGG CGACTCGTTA TTGATCGTAT TGGGGAACCC CGGAGATTTG
                                         _____T7 TERMINATOR_____>

2840        2850        2860        2870        2880
              *     *     *     *     *     *     *     *     *
           GGGTCTTGAG GGGTTTTTTG CTGAAAGGAG GAACTATATC CGGATCGATT
           CCCAGAACTC CCCAAAAAAC GACTTTCCTC CTTGATATAG GCCTAGCTAA
           ___T7 TERMINATOR____>

2890        2900        2910        2920
              *     *     *     *  '  *     *     *     *     *
           AAATAAGGAG GAATAACAT ATG AGC AGC TCA GAG GAG GTG TCC TGG ATT
           TTTATTCCTC CTTATTGTA TAC TCG TCG AGT CTC CTC CAC AGG ACC TAA
                                Met Ser Ser Ser Glu Glu Val Ser Trp Ile>
                                ___h___h___h____CKIIB__h___h___h___h___>
```

FIG. 71

```
         2930        2940        2950        2960        2970
           *    *    *    *    *    *    *    *    *
         TCC  TGG  TTC  TGT  GGG  CTC  CGT  GGC  AAT  GAA  TTC  TTC  TGT  GAA  GTG
         AGG  ACC  AAG  ACA  CCC  GAG  GCA  CCG  TTA  CTT  AAG  AAG  ACA  CTT  CAC
         Ser  Trp  Phe  Cys  Gly  Leu  Arg  Gly  Asn  Glu  Phe  Phe  Cys  Glu  Val>
         ___h___h___h___h___h___h_CKIIB___h___h___h___h___h___h___>

2980        2990        3000        3010
                *    *    *    *    *    *    *    *    *
              GAT  GAA  GAC  TAC  ATC  CAG  GAC  AAA  TTT  AAT  CTT  ACT  GGA  CTC  AAT
              CTA  CTT  CTG  ATG  TAG  GTC  CTG  TTT  AAA  TTA  GAA  TGA  CCT  GAG  TTA
              Asp  Glu  Asp  Tyr  Ile  Gln  Asp  Lys  Phe  Asn  Leu  Thr  Gly  Leu  Asn>
              ___h___h___h___h___h___h_CKIIB___h___h___h___h___h___h___>

3020        3030        3040        3050        3060
           *    *    *    *    *    *    *    *    *
         GAG  CAG  GTC  CCT  CAC  TAC  CGA  CAA  GCT  CTA  GAC  ATG  ATC  TTG  GAC
         CTC  GTC  CAG  GGA  GTG  ATG  GCT  GTT  CGA  GAT  CTG  TAC  TAG  AAC  CTG
         Glu  Gln  Val  Pro  His  Tyr  Arg  Gln  Ala  Leu  Asp  Met  Ile  Leu  Asp>
         ___h___h___h___h___h___h_CKIIB___h___h___h___h___h___h___>

3070        3080        3090        3100
                *    *    *    *    *    *    *    *    *
              CTG  GAG  CCT  GAT  GAA  GAA  CTG  GAA  GAC  AAC  CCC  AAC  CAG  AGT  GAC
              GAC  CTC  GGA  CTA  CTT  CTT  GAC  CTT  CTG  TTG  GGG  TTG  GTC  TCA  CTG
              Leu  Glu  Pro  Asp  Glu  Glu  Leu  Glu  Asp  Asn  Pro  Asn  Gln  Ser  Asp>
              ___h___h___h___h___h___h_CKIIB___h___h___h___h___h___h___>

3110        3120        3130        3140        3150
           *    *    *    *    *    *    *    *    *
         CTG  ATT  GAG  CAG  GCA  GCC  GAG  ATG  CTT  TAT  GGA  TTG  ATC  CAC  GCC
         GAC  TAA  CTC  GTC  CGT  CGG  CTC  TAC  GAA  ATA  CCT  AAC  TAG  GTG  CGG
         Leu  Ile  Glu  Gln  Ala  Ala  Glu  Met  Leu  Tyr  Gly  Leu  Ile  His  Ala>
         ___h___h___h___h___h___h_CKIIB___h___h___h___h___h___h___>

3160        3170        3180        3190
                *    *    *    *    *    *    *    *    *
              CGC  TAC  ATC  CTT  ACC  AAC  CGT  GGC  ATC  GCC  CAG  ATG  TTG  GAA  AAG
              GCG  ATG  TAG  GAA  TGG  TTG  GCA  CCG  TAG  CGG  GTC  TAC  AAC  CTT  TTC
              Arg  Tyr  Ile  Leu  Thr  Asn  Arg  Gly  Ile  Ala  Gln  Met  Leu  Glu  Lys>
              ___h___h___h___h___h___h_CKIIB___h___h___h___h___h___h___>
```

FIG. 7J

```
       3200        3210        3220        3230        3240
         *    *    *    *    *    *    *    *    *    *
       TAC CAG CAA GGA GAC TTT GGT TAC TGT CCT CGT GTG TAC TGT GAG
       ATG GTC GTT CCT CTG AAA CCA ATG ACA GGA GCA CAC ATG ACA CTC
       Tyr Gln Gln Gly Asp Phe Gly Tyr Cys Pro Arg Val Tyr Cys Glu>
       __h___h___h___h___h___h_CKIIB____h___h___h___h___h___h___>

3250        3260        3270        3280
         *    *    *    *    *    *    *    *    *
       AAC CAG CCA ATG CTT CCC ATT GGC CTT TCA GAC ATC CCA GGT GAA
       TTG GTC GGT TAC GAA GGG TAA CCG GAA AGT CTG TAG GGT CCA CTT
       Asn Gln Pro Met Leu Pro Ile Gly Leu Ser Asp Ile Pro Gly Glu>
       __h___h___h___h___h___h_CKIIB____h___h___h___h___h___h___>

3290        3300        3310        3320        3330
         *    *    *    *    *    *    *    *    *    *
       GCC ATG GTG AAG CTC TAC TGC CCC AAG TGC ATG GAT GTG TAC ACA
       CGG TAC CAC TTC GAG ATG ACG GGG TTC ACG TAC CTA CAC ATG TGT
       Ala Met Val Lys Leu Tyr Cys Pro Lys Cys Met Asp Val Tyr Thr>
       __h___h___h___h___h___h_CKIIB____h___h___h___h___h___h___>

3340        3350        3360        3370
         *    *    *    *    *    *    *    *    *
       CCC AAG TCA TCA AGA CAC CAT CAC ACG GAT GGC GCC TAC TTC GGC
       GGG TTC AGT AGT TCT GTG GTA GTG TGC CTA CCG CGG ATG AAG CCG
       Pro Lys Ser Ser Arg His His His Thr Asp Gly Ala Tyr Phe Gly>
       __h___h___h___h___h___h_CKIIB____h___h___h___h___h___h___>

3380        3390        3400        3410        3420
         *    *    *    *    *    *    *    *    *
       ACT GGT TTC CCT CAC ATG CTC TTC ATG GTG CAT CCC GAG TAC CGG
       TGA CCA AAG GGA GTG TAC GAG AAG TAC CAC GTA GGG CTC ATG GCC
       Thr Gly Phe Pro His Met Leu Phe Met Val His Pro Glu Tyr Trp>
       __h___h___h___h___h___h_CKIIB____h___h___h___h___h___h___>

3430        3440        3450        3460
         *    *    *    *    *    *    *    *    *
       CCC AAG AGA CCT GCC AAC CAG TTT GTG CCC AGG CTC TAC GGT TTC
       GGG TTC TCT GGA CGG TTG GTC AAA CAC GGG TCC GAG ATG CCA AAG
       Pro Lys Arg Pro Ala Asn Gln Phe Val Pro Arg Leu Tyr Gly Phe>
       __h___h___h___h___h___h_CKIIB____h___h___h___h___h___h___>
```

FIG. 7K

```
              3470         3480         3490         3500         3510
               *    *    *    *    *    *    *    *    *    *
              AAG  ATC  CAT  GCG  ATG  GCC  TAC  CAG  CTG  CAG  CTC  CAA  GCC  GCC  AGC
              TTC  TAG  GTA  CGC  TAC  CGG  ATG  GTC  GAC  GTC  GAG  GTT  CGG  CGG  TCG
              Lys  Ile  His  Ala  Met  Ala  Tyr  Gln  Leu  Gln  Leu  Gln  Ala  Ala  Ser>
              ___h___h___h___h___h___h_CKIIB____h___h___h___h___h___h___>

3520         3530         3540         3550         3560
                *    *    *    *    *    *    *    *    *    *
              AAC  TTC  AAG  AGC  CCA  GTC  AAG  ACG  ATT  CGC  TAA  GTC  GACAAGAAGG
              TTG  AAG  TTC  TCG  GGT  CAG  TTC  TGC  TAA  GCG  ATT  CAG  CTGTTCTTCC
              Asn  Phe  Lys  Ser  Pro  Val  Lys  Thr  Ile  Arg  ***>
              ___h___h___h___h_CKIIB____h___h___h___h___>

3570         3580         3590         3600
                    *    *    *    *    *    *    *    *    *
              AGATATACAT  ATG  TCG  GGA  CCC  GTG  CCA  AGC  AGG  GCC  AGA  GTT  TAC
              TCTATATGTA  TAC  AGC  CCT  GGG  CAC  GGT  TCG  TCC  CGG  TCT  CAA  ATG
                          Met  Ser  Gly  Pro  Val  Pro  Ser  Arg  Ala  Arg  Val  Tyr>
                          ___i___i___i___i____CKIIA__i___i___i___i___>

3610         3620         3630         3640         3650
               *    *    *    *    *    *    *    *    *    *
              ACA  GAT  GTT  AAT  ACA  CAC  AGA  CCT  CGA  GAA  TAC  TGG  GAT  TAC  GAG
              TGT  CTA  CAA  TTA  TGT  GTG  TCT  GGA  GCT  CTT  ATG  ACC  CTA  ATG  CTC
              Thr  Asp  Val  Asn  Thr  His  Arg  Pro  Arg  Glu  Tyr  Trp  Asp  Tyr  Glu>
              ___i___i___i___i___i___i_CKIIA____i___i___i___i___i___i___>

3660         3670         3680         3690
                *    *    *    *    *    *    *    *    *
              TCA  CAT  GTG  GTG  GAA  TGG  GGA  AAT  CAA  GAT  GAC  TAC  CAG  CTG  GTT
              AGT  GTA  CAC  CAC  CTT  ACC  CCT  TTA  GTT  CTA  CTG  ATG  GTC  GAC  CAA
              Ser  His  Val  Val  Glu  Trp  Gly  Asn  Gln  Asp  Asp  Tyr  Gln  Leu  Val>
              ___i___i___i___i___i___i_CKIIA____i___i___i___i___i___i___>

3700         3710         3720         3730         3740
               *    *    *    *    *    *    *    *    *    *
              CGA  AAA  TTA  GGC  CGA  GGT  AAA  TAC  AGT  GAA  GTA  TTT  GAA  GCC  ATC
              GCT  TTT  AAT  CCG  GCT  CCA  TTT  ATG  TCA  CTT  CAT  AAA  CTT  CGG  TAG
              Arg  Lys  Leu  Gly  Arg  Gly  Lys  Tyr  Ser  Glu  Val  Phe  Glu  Ala  Ile>
              ___i___i___i___i___i___i_CKIIA____i___i___i___i___i___i___>
```

FIG. 7L

```
              3750         3760         3770         3780
               *    *    *    *    *    *    *    *    *
              AAC  ATC  ACA  AAT  AAT  GAA  AAA  GTT  GTT  GTT  AAA  ATT  CTC  AAG  CCA
              TTG  TAG  TGT  TTA  TTA  CTT  TTT  CAA  CAA  CAA  TTT  TAA  GAG  TTC  GGT
              Asn  Ile  Thr  Asn  Asn  Glu  Lys  Val  Val  Val  Lys  Ile  Leu  Lys  Pro>
              __i___i___i___i___i___i_CKIIA___i___i___i___i___i___i__>

3790         3800         3810         3820         3830
          *    *    *    *    *    *    *    *    *
         GTA  AAA  AAG  AAG  AAA  ATT  AAG  CGT  GAA  ATA  AAG  ATT  TTG  GAG  AAT
         CAT  TTT  TTC  TTC  TTT  TAA  TTC  GCA  CTT  TAT  TTC  TAA  AAC  CTC  TTA
         Val  Lys  Lys  Lys  Lys  Ile  Lys  Arg  Glu  Ile  Lys  Ile  Leu  Glu  Asn>
         __i___i___i___i___i___i_CKIIA___i___i___i___i___i___i__>

3840         3850         3860         3870
               *    *    *    *    *    *    *    *    *
              TTG  AGA  GGA  GGT  CCC  AAC  ATC  ATC  ACA  CTG  GCA  GAC  ATT  GTA  AAA
              AAC  TCT  CCT  CCA  GGG  TTG  TAG  TAG  TGT  GAC  CGT  CTG  TAA  CAT  TTT
              Leu  Arg  Gly  Gly  Pro  Asn  Ile  Ile  Thr  Leu  Ala  Asp  Ile  Val  Lys>
              __i___i___i___i___i___i_CKIIA___i___i___i___i___i___i__>

3880         3890         3900         3910         3920
               *    *    *    *    *    *    *    *    *
              GAC  CCT  GTG  TCA  CGA  ACC  CCC  GCC  TTG  GTT  TTT  GAA  CAC  GTA  AAC
              CTG  GGA  CAC  AGT  GCT  TGG  GGG  CGG  AAC  CAA  AAA  CTT  GTG  CAT  TTG
              Asp  Pro  Val  Ser  Arg  Thr  Pro  Ala  Leu  Val  Phe  Glu  His  Val  Asn>
              __i___i___i___i___i___i_CKIIA___i___i___i___i___i___i__>

3930         3940         3950         3960
               *    *    *    *    *    *    *    *    *
              AAC  ACA  GAC  TTC  AAG  CAA  TTG  TAC  CAG  ACG  TTA  ACA  GAC  TAT  GAT
              TTG  TGT  CTG  AAG  TTC  GTT  AAC  ATG  GTC  TGC  AAT  TGT  CTG  ATA  CTA
              Asn  Thr  Asp  Phe  Lys  Gln  Leu  Tyr  Gln  Thr  Leu  Thr  Asp  Tyr  Asp>
              __i___i___i___i___i___i_CKIIA___i___i___i___i___i___i__>

3970         3980         3990         4000         4010
               *    *    *    *    *    *    *    *    *
              ATT  CGA  TTT  TAC  ATG  TAT  GAG  ATT  CTG  AAG  GCC  CTG  GAT  TAT  TGT
              TAA  GCT  AAA  ATG  TAC  ATA  CTC  TAA  GAC  TTC  CGG  GAC  CTA  ATA  ACA
              Ile  Arg  Phe  Tyr  Met  Tyr  Glu  Ile  Leu  Lys  Ala  Leu  Asp  Tyr  Cys>
              __i___i___i___i___i___i_CKIIA___i___i___i___i___i___i__>
```

FIG. 7M

```
        4020        4030        4040        4050
         *  *  *  *  *  *  *  *  *
        CAC AGC ATG GGA ATT ATG CAC AGA GAT GTC AAG CCC CAT AAT GTC
        GTG TCG TAC CCT TAA TAC GTG TCT CTA CAG TTC GGG GTA TTA CAG
        His Ser Met Gly Ile Met His Arg Asp Val Lys Pro His Asn Val>
        __i__i__i__i__i__i_CKIIA___i__i__i__i__i__i__>

4060        4070        4080        4090        4100
         *  *  *  *  *  *  *  *  *
        ATG ATT GAT CAT GAG CAC AGA AAG CTA CGA CTA ATA GAC TGG GGT
        TAC TAA CTA GTA CTC GTG TCT TTC GAT GCT GAT TAT CTG ACC CCA
        Met Ile Asp His Glu His Arg Lys Leu Arg Leu Ile Asp Trp Gly>
        __i__i__i__i__i__i_CKIIA___i__i__i__i__i__i__>

4110        4120        4130        4140
         *  *  *  *  *  *  *  *  *
        TTG GCT GAG TTT TAT CAT CCT GGC CAA GAA TAT AAT GTC CGA GTT
        AAC CGA CTC AAA ATA GTA GGA CCG GTT CTT ATA TTA CAG GCT CAA
        Leu Ala Glu Phe Tyr His Pro Gly Gln Glu Tyr Asn Val Arg Val>
        __i__i__i__i__i__i_CKIIA___i__i__i__i__i__i__>

4150        4160        4170        4180        4190
         *  *  *  *  *  *  *  *  *
        GCT TCC CGA TAC TTC AAA GGT CCT GAG CTA CTT GTA GAC TAT CAG
        CGA AGG GCT ATG AAG TTT CCA GGA CTC GAT GAA CAT CTG ATA GTC
        Ala Ser Arg Tyr Phe Lys Gly Pro Glu Leu Leu Val Asp Tyr Gln>
        __i__i__i__i__i__i_CKIIA___i__i__i__i__i__i__>

4200        4210        4220        4230
         *  *  *  *  *  *  *  *  *
        ATG TAC GAT TAT AGT TTG GAT ATG TGG AGT TTG GGT TGT ATG CTG
        TAC ATG CTA ATA TCA AAC CTA TAC ACC TCA AAC CCA ACA TAC GAC
        Met Tyr Asp Tyr Ser Leu Asp Met Trp Ser Leu Gly Cys Met Leu>
        __i__i__i__i__i__i_CKIIA___i__i__i__i__i__i__>

4240        4250        4260        4270        4280
         *  *  *  *  *  *  *  *  *
        GCA AGT ATG ATC TTT CGG AAG GAG CCA TTT TTC CAT GGA CAT GAC
        CGT TCA TAC TAG AAA GCC TTC CTC GGT AAA AAG GTA CCT GTA CTG
        Ala Ser Met Ile Phe Trp Lys Glu Pro Phe Phe His Gly His Asp>
        __i__i__i__i__i__i_CKIIA___i__i__i__i__i__i__>
```

FIG. 7N

```
              4290         4300         4310         4320
               *            *            *            *     *    *    *    *    *
         AAT  TAT  GAT  CAG  TTG  GTG  AGG  ATA  GCC  AAG  GTT  CTG  GGG  ACA  GAA
         TTA  ATA  CTA  GTC  AAC  CAC  TCC  TAT  CGG  TTC  CAA  GAC  CCC  TGT  CTT
         Asn  Tyr  Asp  Gln  Leu  Val  Arg  Ile  Ala  Lys  Val  Leu  Gly  Thr  Glu>
         ___i___i___i___i___i___i__CKIIA___i___i___i___i___i___i___>

4330         4340         4350         4360         4370
               *            *            *            *            *     *    *    *    *
         GAT  TTA  TAT  GAC  TAT  ATT  GAC  AAA  TAC  AAC  ATT  GAA  TTA  GAT  CCA
         CTA  AAT  ATA  CTG  ATA  TAA  CTG  TTT  ATG  TTG  TAA  CTT  AAT  CTA  GGT
         Asp  Leu  Tyr  Asp  Tyr  Ile  Asp  Lys  Tyr  Asn  Ile  Glu  Leu  Asp  Pro>
         ___i___i___i___i___i___i__CKIIA___i___i___i___i___i___i___>

4380         4390         4400         4410
                    *            *            *            *     *    *    *    *    *
         CGT  TTC  AAT  GAT  ATC  TTG  GGC  AGA  CAC  TCT  CGA  AAG  CGA  TGG  GAA
         GCA  AAG  TTA  CTA  TAG  AAC  CCG  TCT  GTG  AGA  GCT  TTC  GCT  ACC  CTT
         Arg  Phe  Asn  Asp  Ile  Leu  Gly  Arg  His  Ser  Arg  Lys  Arg  Trp  Glu>
         ___i___i___i___i___i___i__CKIIA___i___i___i___i___i___i___>

4420         4430         4440         4450         4460
               *            *            *            *            *     *    *    *    *
         CGC  TTT  GTC  CAC  AGT  GAA  AAT  CAG  CAC  CTT  GTC  AGC  CCT  GAG  GCC
         GCG  AAA  CAG  GTG  TCA  CTT  TTA  GTC  GTG  GAA  CAG  TCG  GGA  CTC  CGG
         Arg  Phe  Val  His  Ser  Glu  Asn  Gln  His  Leu  Val  Ser  Pro  Glu  Ala>
         ___i___i___i___i___i___i__CKIIA___i___i___i___i___i___i___>

4470         4480         4490         4500
                    *            *            *            *     *    *    *    *    *
         TTG  GAT  TTC  CTG  GAC  AAA  CTG  CTG  CGA  TAT  GAC  CAC  CAG  TCA  TGG
         AAC  CTA  AAG  GAC  CTG  TTT  GAC  GAC  GCT  ATA  CTG  GTG  GTC  AGT  GCC
         Leu  Asp  Phe  Leu  Asp  Lys  Leu  Leu  Arg  Tyr  Asp  His  Gln  Ser  Trp>
         ___i___i___i___i___i___i__CKIIA___i___i___i___i___i___i___>

4510         4520         4530         4540         4550
               *            *            *            *            *     *    *    *    *
         CTT  ACT  GCA  AGA  GAG  GCA  ATG  GAG  CAC  CCC  TAT  TTC  TAC  ACT  GTT
         GAA  TGA  CGT  TCT  CTC  CGT  TAC  CTC  GTG  GGG  ATA  AAG  ATG  TGA  CAA
         Leu  Thr  Ala  Arg  Glu  Ala  Met  Glu  His  Pro  Tyr  Phe  Tyr  Thr  Val>
         ___i___i___i___i___i___i__CKIIA___i___i___i___i___i___i___>
```

FIG. 70

```
          4560      4570      4580      4590
           *    *    *    *    *    *    *    *    *
         GTG AAG GAC CAG GCT CGA ATG GGT TCA TCT AGC ATG CCA GGG GGC
         CAC TTC CTG GTC CGA GCT TAC CCA AGT AGA TCG TAC GGT CCC CCG
         Val Lys Asp Gln Ala Arg Met Gly Ser Ser Ser Met Pro Gly Gly>
         __i___i___i___i___i___i_CKIIA___i___i___i___i___i___i__>

4600      4610      4620      4630      4640
           *    *    *    *    *    *    *    *    *
         AGT ACG CCC GTC AGC AGC GCC AAT ATG ATG TCA GGG ATT TCT TCA
         TCA TGC GGG CAG TCG TCG CGG TTA TAC TAC AGT CCC TAA AGA AGT
         Ser Thr Pro Val Ser Ser Ala Asn Met Met Ser Gly Ile Ser Ser>
         __i___i___i___i___i___i_CKIIA___i___i___i___i___i___i__>

4650      4660      4670      4680
            *    *    *    *    *    *    *    *    *
         GTG CCA ACC CCT TCA CCC CTT GGA CCT CTG GCA GGC TCA CCA GTG
         CAC GGT TGG GGA AGT GGG GAA CCT GGA GAC CGT CCG AGT GGT CAC
         Val Pro Thr Pro Ser Pro Leu Gly Pro Leu Ala Gly Ser Pro Val>
         __i___i___i___i___i___i_CKIIA___i___i___i___i___i___i__>

4690      4700      4710      4720      4730
           *    *    *    *    *    *    *    *    *
         ATT GCT GCT GCC AAC CCC CTT GGG ATG CCT GTT CCA GCT GCC GCT
         TAA CGA CGA CGG TTG GGG GAA CCC TAC GGA CAA GGT CGA CGG CGA
         Ile Ala Ala Ala Asn Pro Leu Gly Met Pro Val Pro Ala Ala Ala>
         __i___i___i___i___i___i_CKIIA___i___i___i___i___i___i__>

4740      4750      4760      4770      4780
            *    *    *    *    *    *    *    *    *    *
         GGC GCT CAG CAG TAA GCTA GCGTCGACGG ATCCGGCTGC TAACAAAGCC
         CCG CGA GTC GTC ATT CGAT CGCAGCTGCC TAGGCCGACG ATTGTTTCGG
         Gly Ala Gln Gln ***>
         __i_CKIIA___i__>

4790       4800       4810       4820       4830
            *    *    *    *    *    *    *    *    *    *
         CGAAAGGAAG CTGAGTTGGC TGCTGCCACC GCTGAGCAAT AACTAGCATA
         GCTTTCCTTC GACTCAACCG ACGACGGTGG CGACTCGTTA TTGATCGTAT
                                                            _____>

4840       4850       4860       4870       4880
            *    *    *    *    *    *    *    *    *    *
         ACCCCTTGGG GCCTCTAAAC GGGTCTTGAG GGGTTTTTTG CTGAAAGGAG
         TGGGGAACCC CGGAGATTTG CCCAGAACTC CCCAAAAAAC GACTTCCTC
         _10_____j_2_T7 TERMINATOR____j_40_____>
```

FIG. 7P

```
          4890       4900       4910       4920       4930
           *  *       *  *       *  *       *  *       *  *
      GAACTATATC CGGATATCCC GCAAGAGGCC CGGCAGTACC GGCATAACCA
      CTTGATATAG GCCTATAGGG CGTTCTCCGG GCCGTCATGG CCGTATTGGT 4940       4950       4960       4970       4980
           *  *       *  *       *  *       *  *       *  *
      AGCCTATGCC TACAGCATCC AGGGTGACGG TGCCGAGGAT GACGATGAGC
      TCGGATACGG ATGTCGTAGG TCCCACTGCC ACGGCTCCTA CTGCTACTCG 4990       5000       5010       5020       5030
           *  *       *  *       *  *       *  *       *  *
      GCATTGTTAG ATTTCATACA CGGTGCCTGA CTGCGTTAGC AATTTAACTG
      CGTAACAATC TAAAGTATGT GCCACGGACT GACGCAATCG TTAAATTGAC 5040       5050       5060       5070       5080
           *  *       *  *       *  *       *  *       *  *
      TGATAAACTA CCGCATTAAA GCTTACTGGC TTAACTATGC GGCATCAGAG
      ACTATTTGAT GGCGTAATTT CGAATGACCG AATTGATACG CCGTAGTCTC 5090       5100       5110       5120       5130
           *  *       *  *       *  *       *  *       *  *
      CAGATTGTAC TGAGAGTGCA CCATATATGC GGTGTGAAAT ACCGCACAGA
      GTCTAACATG ACTCTCACGT GGTATATACG CCACACTTTA TGGCGTGTCT 5140       5150       5160       5170       5180
           *  *       *  *       *  *       *  *       *  *
      TGCGTAAGGA GAAAATACCG CATCAGGCGC TCTTCCGCTT CCTCGCTCAC
      ACGCATTCCT CTTTTATGGC GTAGTCCGCG AGAAGGCGAA GGAGCGAGTG 5190       5200       5210       5220       5230
           *  *       *  *       *  *       *  *       *  *
      TGACTCGCTG CGCTCGGTCG TTCGGCTGCG GCGAGCGGTA TCAGCTCACT
      ACTGAGCGAC GCGAGCCAGC AAGCCGACGC CGCTCGCCAT AGTCGAGTGA 5240       5250       5260       5270       5280
           *  *       *  *       *  *       *  *       *  *
      CAAAGGCGGT AATACGGTTA TCCACAGAAT CAGGGGATAA CGCAGGAAAG
      GTTTCCGCCA TTATGCCAAT AGGTGTCTTA GTCCCCTATT GCGTCCTTTC 5290       5300       5310       5320       5330
           *  *       *  *       *  *       *  *       *  *
      AACATGTGAG CAAAAGGCCA GCAAAAGGCC AGGAACCGTA AAAAGGCCGC
      TTGTACACTC GTTTTCCGGT CGTTTTCCGG TCCTTGGCAT TTTTCCGGCG
```

FIG. 7Q

```
        5340       5350       5360       5370       5380
          *    *     *    *     *    *     *    *     *    *
       GTTGCTGGCG TTTTTCCATA GGCTCCGCCC CCCTGACGAG CATCACAAAA
       CAACGACCGC AAAAAGGTAT CCGAGGCGGG GGGACTGCTC GTAGTGTTTT
                <_____c_____ORI_____c_____

5390       5400       5410       5420       5430
          *    *     *    *     *    *     *    *     *    *
       ATCGACGCTC AAGTCAGAGG TGGCGAAACC CGACAGGACT ATAAAGATAC
       TAGCTGCGAG TTCAGTCTCC ACCGCTTTGG GCTGTCCTGA TATTTCTATG 5440       5450       5460       5470       5480
          *    *     *    *     *    *     *    *     *    *
       CAGGCGTTTC CCCCTGGAAG CTCCCTCGTG CGCTCTCCTG TTCCGACCCT
       GTCCGCAAAG GGGGACCTTC GAGGGAGCAC GCGAGAGGAC AAGGCTGGGA 5490       5500       5510       5520       5530
          *    *     *    *     *    *     *    *     *    *
       GCCGCTTACC GGATACCTGT CCGCCTTTCT CCCTTCGGGA AGCGTGGCGC
       CGGCGAATGG CCTATGGACA GGCGGAAAGA GGGAAGCCCT TCGCACCGCG 5540       5550       5560       5570       5580
          *    *     *    *     *    *     *    *     *    *
       TTTCTCATAG CTCACGCTGT AGGTATCTCA GTTCGGTGTA GGTCGTTCGC
       AAAGAGTATC GAGTGCGACA TCCATAGAGT CAAGCCACAT CCAGCAAGCG 5590       5600       5610       5620       5630
          *    *     *    *     *    *     *    *     *    *
       TCCAAGCTGG GCTGTGTGCA CGAACCCCCC GTTCAGCCCG ACCGCTGCGC
       AGGTTCGACC CGACACACGT GCTTGGGGGG CAAGTCGGGC TGGCGACGCG 5640       5650       5660       5670       5680
          *    *     *    *     *    *     *    *     *    *
       CTTATCCGGT AACTATCGTC TTGAGTCCAA CCCGGTAAGA CACGACTTAT
       GAATAGGCCA TTGATAGCAG AACTCAGGTT GGGCCATTCT GTGCTGAATA 5690       5700       5710       5720       5730
          *    *     *    *     *    *     *    *     *    *
       CGCCACTGGC AGCAGCCACT GGTAACAGGA TTAGCAGAGC GAGGTATGTA
       GCGGTGACCG TCGTCGGTGA CCATTGTCCT AATCGTCTCG CTCCATACAT 5740       5750       5760       5770       5780
          *    *     *    *     *    *     *    *     *    *
       GGCGGTGCTA CAGAGTTCTT GAAGTGGTGG CCTAACTACG GCTACACTAG
       CCGCCACGAT GTCTCAAGAA CTTCACCACC GGATTGATGC CGATGTGATC
```

FIG. 7R

```
          5790        5800        5810        5820        5830
            *  *        *  *        *  *        *  *        *  *
       AAGGACAGTA  TTTGGTATCT  GCGCTCTGCT  GAAGCCAGTT  ACCTTCGGAA
       TTCCTGTCAT  AAACCATAGA  CGCGAGACGA  CTTCGGTCAA  TGGAAGCCTT 5840        5850        5860        5870        5880
            *  *        *  *        *  *        *  *        *  *
       AAAGAGTTGG  TAGCTCTTGA  TCCGGCAAAC  AAACCACCGC  TGGTAGCGGT
       TTTCTCAACC  ATCGAGAACT  AGGCCGTTTG  TTTGGTGGCG  ACCATCGCCA 5890        5900        5910        5920        5930
            *  *        *  *        *  *        *  *        *  *
       GGTTTTTTTG  TTTGCAAGCA  GCAGATTACG  CGCAGAAAAA  AAGGATCTCA
       CCAAAAAAAC  AAACGTTCGT  CGTCTAATGC  GCGTCTTTTT  TTCCTAGAGT 5940        5950        5960        5970        5980
            *  *        *  *        *  *        *  *        *  *
       AGAAGATCCT  TTGATCTTTT  CTACGGGGTC  TGACGCTCAG  TGGAACGAAA
       TCTTCTAGGA  AACTAGAAAA  GATGCCCCAG  ACTGCGAGTC  ACCTTGCTTT 5990        6000        6010        6020        6030
            *  *        *  *        *  *        *  *        *  *
       ACTCACGTTA  AGGGATTTTG  GTCATGAACA  ATAAAACTGT  CTGCTTACAT
       TGAGTGCAAT  TCCCTAAAAC  CAGTACTTGT  TATTTTGACA  GACGAATGTA 6040        6050        6060        6070
            *  *        *  *        *  *        *  *        *
       AAACAGTAAT  ACAAGGGGTG  TT ATG AGC CAT ATT CAA CGG GAA ACG TCT
       TTTGTCATTA  TGTTCCCCAC  AA TAC TCG GTA TAA GTT GCC CTT TGC AGA
                               Met Ser His Ile Gln Trp Glu Thr Ser>
                               ___d___d___d___KANR___d___d___d___>

6080        6090        6100        6110        6120
       *  *        *  *        *  *        *  *        *  *
   TGC TCT AGG CCG CGA TTA AAT TCC AAC ATG GAT GCT GAT TTA TAT
   ACG AGA TCC GGC GCT AAT TTA AGG TTG TAC CTA CGA CTA AAT ATA
   Cys Ser Arg Pro Arg Leu Asn Ser Asn Met Asp Ala Asp Leu Tyr>
   ___d___d___d___d___d___d___KANR___d___d___d___d___d___d___>

6130        6140        6150        6160
            *  *        *  *        *  *        *  *        *
       GGG TAT AAA TGG GCT CGC GAT AAT GTC GGG CAA TCA GGT GCG ACA
       CCC ATA TTT ACC CGA GCG CTA TTA CAG CCC GTT AGT CCA CGC TGT
       Gly Tyr Lys Trp Ala Arg Asp Asn Val Gly Gln Ser Gly Ala Thr>
       ___d___d___d___d___d___d___KANR___d___d___d___d___d___d___>
```

FIG. 7S

```
       6170       6180       6190       6200       6210
  *    *    *    *    *    *    *    *    *
  ATC  TAT  CGA  TTG  TAT  GGG  AAG  CCC  GAT  GCG  CCA  GAG  TTG  TTT  CTG
  TAG  ATA  GCT  AAC  ATA  CCC  TTC  GGG  CTA  CGC  GGT  CTC  AAC  AAA  GAC
  Ile  Tyr  Arg  Leu  Tyr  Gly  Lys  Pro  Asp  Ala  Pro  Glu  Leu  Phe  Leu>
  __d__d__d__d__d__d__KANR____d__d__d__d__d__d__>

6220       6230       6240       6250
       *    *    *    *    *    *    *    *    *
  AAA  CAT  GGC  AAA  GGT  AGC  GTT  GCC  AAT  GAT  GTT  ACA  GAT  GAG  ATG
  TTT  GTA  CCG  TTT  CCA  TCG  CAA  CGG  TTA  CTA  CAA  TGT  CTA  CTC  TAC
  Lys  His  Gly  Lys  Gly  Ser  Val  Ala  Asn  Asp  Val  Thr  Asp  Glu  Met>
  __d__d__d__d__d__d__KANR____d__d__d__d__d__d__>

6260       6270       6280       6290       6300
  *    *    *    *    *    *    *    *    *
  GTC  AGA  CTA  AAC  TGG  CTG  ACG  GAA  TTT  ATG  CCT  CTT  CCG  ACC  ATC
  CAG  TCT  GAT  TTG  ACC  GAC  TGC  CTT  AAA  TAC  GGA  GAA  GGC  TGG  TAG
  Val  Arg  Leu  Asn  Trp  Leu  Thr  Glu  Phe  Met  Pro  Leu  Pro  Thr  Ile>
  __d__d__d__d__d__d__KANR____d__d__d__d__d__d__>

6310       6320       6330       6340
       *    *    *    *    *    *    *    *    *
  AAG  CAT  TTT  ATC  CGT  ACT  CCT  GAT  GAT  GCA  TGG  TTA  CTC  ACC  ACT
  TTC  GTA  AAA  TAG  GCA  TGA  GGA  CTA  CTA  CGT  ACC  AAT  GAG  TGG  TGA
  Lys  His  Phe  Ile  Arg  Thr  Pro  Asp  Asp  Ala  Trp  Leu  Leu  Thr  Thr>
  __d__d__d__d__d__d__KANR____d__d__d__d__d__d__>

6350       6360       6370       6380       6390
  *    *    *    *    *    *    *    *    *
  GCG  ATC  CCC  GGG  AAA  ACA  GCA  TTC  CAG  GTA  TTA  GAA  GAA  TAT  CCT
  CGC  TAG  GGG  CCC  TTT  TGT  CGT  AAG  GTC  CAT  AAT  CTT  CTT  ATA  GGA
  Ala  Ile  Pro  Gly  Lys  Thr  Ala  Phe  Gln  Val  Leu  Glu  Glu  Tyr  Pro>
  __d__d__d__d__d__d__KANR____d__d__d__d__d__d__>

6400       6410       6420       6430
       *    *    *    *    *    *    *    *    *
  GAT  TCA  GGT  GAA  AAT  ATT  GTT  GAT  GCG  CTG  GCA  GTG  TTC  CTG  CGC
  CTA  AGT  CCA  CTT  TTA  TAA  CAA  CTA  CGC  GAC  CGT  CAC  AAG  GAC  GCG
  Asp  Ser  Gly  Glu  Asn  Ile  Val  Asp  Ala  Leu  Ala  Val  Phe  Leu  Arg>
  __d__d__d__d__d__d__KANR____d__d__d__d__d__d__>
```

FIG. 7T

```
     6440        6450        6460        6470        6480
       *    *    *    *    *    *    *    *    *
     CGG TTG CAT TCG ATT CCT GTT TGT AAT TGT CCT TTT AAC AGC GAT
     GCC AAC GTA AGC TAA GGA CAA ACA TTA ACA GGA AAA TTG TCG CTA
     Trp Leu His Ser Ile Pro Val Cys Asn Cys Pro Phe Asn Ser Asp>
     ___d___d___d___d___d___d___KANR___d___d___d___d___d___d___>

6490        6500        6510        6520
            *    *    *    *    *    *    *    *    *
          CGC GTA TTT CGT CTC GCT CAG GCG CAA TCA CGA ATG AAT AAC GGT
          GCG CAT AAA GCA GAG CGA GTC CGC GTT AGT GCT TAC TTA TTG CCA
          Arg Val Phe Arg Leu Ala Gln Ala Gln Ser Arg Met Asn Asn Gly>
          ___d___d___d___d___d___d___KANR___d___d___d___d___d___d___>

6530        6540        6550        6560        6570
  *    *    *    *    *    *    *    *    *
TTG GTT GAT GCG AGT GAT TTT GAT GAC GAG CGT AAT GGC TGG CCT
AAC CAA CTA CGC TCA CTA AAA CTA CTG CTC GCA TTA CCG ACC GGA
Leu Val Asp Ala Ser Asp Phe Asp Asp Glu Arg Asn Gly Trp Pro>
___d___d___d___d___d___d___KANR___d___d___d___d___d___d___>

6580        6590        6600        6610
       *    *    *    *    *    *    *    *    *
     GTT GAA CAA GTC TGG AAA GAA ATG CAT AAA CTT TTG CCA TTC TCA
     CAA CTT GTT CAG ACC TTT CTT TAC GTA TTT GAA AAC GGT AAG AGT
     Val Glu Gln Val Trp Lys Glu Met His Lys Leu Leu Pro Phe Ser>
     ___d___d___d___d___d___d___KANR___d___d___d___d___d___d___>

6620        6630        6640        6650        6660
  *    *    *    *    *    *    *    *    *
CCG GAT TCA GTC GTC ACT CAT GGT GAT TTC TCA CTT GAT AAC CTT
GGC CTA AGT CAG CAG TGA GTA CCA CTA AAG AGT GAA CTA TTG GAA
Pro Asp Ser Val Val Thr His Gly Asp Phe Ser Leu Asp Asn Leu>
___d___d___d___d___d___d___KANR___d___d___d___d___d___d___>

6670        6680        6690        6700
            *    *    *    *    *    *    *    *    *
          ATT TTT GAC GAG GGG AAA TTA ATA GGT TGT ATT GAT GTT GGA CGA
          TAA AAA CTG CTC CCC TTT AAT TAT CCA ACA TAA CTA CAA CCT GCT
          Ile Phe Asp Glu Gly Lys Leu Ile Gly Cys Ile Asp Val Gly Arg>
          ___d___d___d___d___d___d___KANR___d___d___d___d___d___d___>
```

FIG. 7U

```
      6710         6720         6730         6740         6750
   *    *    *    *    *    *    *    *    *
   GTC GGA ATC GCA GAC CGA TAC CAG GAT CTT GCC ATC CTA TGG AAC
   CAG CCT TAG CGT CTG GCT ATG GTC CTA GAA CGG TAG GAT ACC TTG
   Val Gly Ile Ala Asp Arg Tyr Gln Asp Leu Ala Ile Leu Trp Asn>
   __d__d__d__d__d__d__KANR___d__d__d__d__d__d__>

6760         6770         6780         6790
     *    *    *    *    *    *    *    *    *
   TGC CTC GGT GAG TTT TCT CCT TCA TTA CAG AAA CGG CTT TTT CAA
   ACG GAG CCA CTC AAA AGA GGA AGT AAT GTC TTT GCC GAA AAA GTT
   Cys Leu Gly Glu Phe Ser Pro Ser Leu Gln Lys Trp Leu Phe Gln>
   __d__d__d__d__d__

6850         6860         6870

*    *    *    *    *    *

TTG ATG CTC GAT GAG TTT TTC TAA GA ATT

AAC TAC GAG CTA CTC AAA AAG ATT CT TAA

Leu Met Leu Asp Glu Phe Phe ***>
   __d__d__d_KANR__d__d__d__>
```

FIG. 7V

```
          10         20         30         40         50
          *  *       *  *       *  *       *  *       *  *
    TTCTCATGTT TGACAGCTTA TCATCGATAA GCTTTAATGC GGTAGTTTAT
    AAGAGTACAA ACTGTCGAAT AGTAGCTATT CGAAATTACG CCATCAAATA 60         70         80         90         100
          *  *       *  *       *  *       *  *       *  *
    CACAGTTAAA TTGCTAACGC AGTCAGGCAC CGTGTATGAA ATCTAACAAT
    GTGTCAATTT AACGATTGCG TCAGTCCGTG GCACATACTT TAGATTGTTA 110        120        130        140        150
          *  *       *  *       *  *       *  *       *  *
    GCGCTCATCG TCATCCTCGG CACCGTCACC CTGGATGCTG TAGGCATAGG
    CGCGAGTAGC AGTAGGAGCC GTGGCAGTGG GACCTACGAC ATCCGTATCC 160        170        180        190        200
          *  *       *  *       *  *       *  *       *  *
    CTTGGTTATG CCGGTACTGC CGGGCCTCTT GCGGGATCGA TAAGCTTTAA
    GAACCAATAC GGCCATGACG GCCCGGAGAA CGCCCTAGCT ATTCGAAATT 210        220        230        240        250
          *  *       *  *       *  *       *  *       *  *
    TGCGGTAGTT TATCACAGTT AAATTGCTAA CGCAGTCAGG CACCGTGTAT
    ACGCCATCAA ATAGTGTCAA TTTAACGATT GCGTCAGTCC GTGGCACATA 260        270        280        290        300
          *  *       *  *       *  *       *  *       *  *
    GAAATCTAAC AATGCGCTCA TCGTCATCCT CGGCACCGTC ACCCTGGATG
    CTTTAGATTG TTACGCGAGT AGCAGTAGGA GCCGTGGCAG TGGGACCTAC 310        320        330        340        350
          *  *       *  *       *  *       *  *       *  *
    CTGTAGGCAT AGGCTTGGTT ATGCCGGTAC TGCCGGGCCT CTTGCGGGAT
    GACATCCGTA TCCGAACCAA TACGGCCATG ACGGCCCGGA GAACGCCCTA 360        370        380        390        400
          *  *       *  *       *  *       *  *       *  *
    ATCCGGATAT AGTTCCTCCT TTCAGCAAAA AACCCCTCAA GACCCGTTTA
    TAGGCCTATA TCAAGGAGGA AAGTCGTTTT TTGGGGAGTT CTGGGCAAAT
                                        <_____T7 TERMINATOR_____

410        420        430        440        450
          *  *       *  *       *  *       *  *       *  *
    GAGGCCCCAA GGGGTTATGC TAGTTATTGC TCAGCGGTGG CAGCAGCCAA
    CTCCGGGGTT CCCCAATACG ATCAATAACG AGTCGCCACC GTCGTCGGTT
    <_20__T7 TERMINATOR___f_
```

FIG. 8A

```
              460        470        480        490        500
               *    *    *    *    *    *    *    *    *    *
             CTCAGCTTCC TTTCGGGCTT TGTTAGCAGC CGGATCCGTC GACGCTAGC TTA
             GAGTCGAAGG AAAGCCCGAA ACAATCGTCG GCCTAGGCAG CTGCGATCG AAT
                                                                    <***
                                                                    <__

510            520            530            540
             *    *    *    *    *    *    *    *    *
           CTG CTG AGC GCC AGC GGC AGC TGG AAC AGG CAT CCC AAG GGG GTT
           GAC GAC TCG CGG TCG CCG TCG ACC TTG TCC GTA GGG TTC CCC CAA
          <Gln Gln Ala Gly Ala Ala Ala Pro Val Pro Met Gly Leu Pro Asn
          <__e__e__e__e__e__e_CKIIA__e__e__e__e__e__e__

550            560            570            580            590
             *    *    *    *    *    *    *    *    *
           GGC AGC AGC AAT CAC TGG TGA GCC TGC CAG AGG TCC AAG GGG TGA
           CCG TCG TCG TTA GTG ACC ACT CGG ACG GTC TCC AGG TTC CCC ACT
          <Ala Ala Ala Ile Val Pro Ser Gly Ala Leu Pro Gly Leu Pro Ser
          <__e__e__e__e__e__e_CKIIA__e__e__e__e__e__e__

600            610            620            630
             *    *    *    *    *    *    *    *    *
           AGG GGT TGG CAC TGA AGA AAT CCC TGA CAT CAT ATT GGC GCT GCT
           TCC CCA ACC GTG ACT TCT TTA GGG ACT GTA GTA TAA CCG CGA CGA
          <Pro Thr Pro Val Ser Ser Ile Gly Ser Met Met Asn Ala Ser Ser
          <__e__e__e__e__e__e_CKIIA__e__e__e__e__e__e__

640            650            660            670            680
             *    *    *    *    *    *    *    *    *
           GAC GGG CGT ACT GCC CCC TGG CAT GCT AGA TGA ACC CAT TCG AGC
           CTG CCC GCA TGA CGG GGG ACC GTA CGA TCT ACT TGG GTA AGC TCG
          <Val Pro Thr Ser Gly Gly Pro Met Ser Ser Ser Gly Met Arg Ala
          <__e__e__e__e__e__e_CKIIA__e__e__e__e__e__e__

690            700            710            720
             *    *    *    *    *    *    *    *    *
           CTG GTC CTT CAC AAC AGT GTA GAA ATA GGG GTG CTC CAT TGC CTC
           GAC CAG GAA GTG TTG TCA CAT CTT TAT CCC CAC GAG GTA ACG GAG
          <Gln Asp Lys Val Val Thr Tyr Phe Tyr Pro His Glu Met Ala Glu
          <__e__e__e__e__e__e_CKIIA__e__e__e__e__e__e__
```

FIG. 8B

```
      730         740         750         760         770
       *     *     *     *     *     *     *     *     *
     TCT TGC AGT AAG CCG TGA CTG GTG GTC ATA TCG CAG CAG TTT GTC
     AGA ACG TCA TTC GGC ACT GAC CAC CAG TAT AGC GTC GTC AAA CAG
     <Arg Ala Thr Leu Trp Ser Gln His Asp Tyr Arg Leu Leu Lys Asp
     <___e___e___e___e___e___e_CKIIA___e___e___e___e___e___e__

780         790         800         810
       *     *     *     *     *     *     *     *     *
     CAG GAA ATC CAA GGC CTC AGG GCT GAC AAG GTG CTG ATT TTC ACT
     GTC CTT TAG GTT CCG GAG TCC CGA CTG TTC CAC GAC TAA AAG TGA
     <Leu Phe Asp Leu Ala Glu Pro Ser Val Leu His Gln Asn Glu Ser
     <___e___e___e___e___e___e_CKIIA___e___e___e___e___e___e__

820         830         840         850         860
       *     *     *     *     *     *     *     *     *
     GTG GAC AAA GCG TTC CCA TCG CTT TCG AGA GTG TCT GCC CAA GAT
     CAC CTG TTT CGC AAG GGT AGC GAA AGC TCT CAC AGA CGG GTT CTA
     <His Val Phe Arg Glu Trp Arg Lys Arg Ser His Arg Gly Leu Ile
     <___e___e___e___e___e___e_CKIIA___e___e___e___e___e___e__

870         880         890         900
       *     *     *     *     *     *     *     *     *
     ATC ATT GAA ACG TGG ATC TAA TTC AAT GTT GTA TTT GTC AAT ATA
     TAG TAA CTT TGC ACC TAG ATT AAG TTA CAA CAT AAA CAG TTA TAT
     <Asp Asn Phe Arg Pro Asp Leu Glu Ile Asn Tyr Lys Asp Ile Tyr
     <___e___e___e___e___e___e_CKIIA___e___e___e___e___e___e__

910         920         930         940         950
       *     *     *     *     *     *     *     *     *
     GTC ATA TAA ATC TTC TGT CCC CAG AAC CTT GGC TAT CCT CAC CAA
     CAG TAT ATT TAG AAG ACA GGG GTC TTG GAA CCG ATA GGA GTG GTT
     <Asp Tyr Leu Asp Glu Thr Gly Leu Val Lys Ala Ile Arg Val Leu
     <___e___e___e___e___e___e_CKIIA___e___e___e___e___e___e__

960         970         980         990
       *     *     *     *     *     *     *     *     *
     CTG ATC ATA ATT GTC ATG TCC ATG GAA AAA TGG CTC CTT CCG AAA
     GAC TAG TAT TAA CAG TAC AGG TAC CTT TTT ACC GAG GAA GGC TTT
     <Gln Asp Tyr Asn Asp His Gly His Phe Phe Pro Glu Lys Trp Phe
     <___e___e___e___e___e___e_CKIIA___e___e___e___e___e___e__
```

FIG. 8C

```
         1000           1010           1020           1030           1040
           *      *      *      *      *      *      *      *      *
         GAT CAT ACT TGC CAG CAT ACA ACC CAA ACT CCA CAT ATC CAA ACT
         CTA GTA TGA ACG GTC GTA TGT TGG GTT TGA GGT GTA TAG GTT TGA
         <Ile Met Ser Ala Leu Met Cys Gly Leu Ser Trp Met Asp Leu Ser
         <___e___e___e___e___e___e_CKIIA___e___e___e___e___e___e__

1050           1060           1070           1080
           *      *      *      *      *      *      *      *      *
         ATA ATC GTA CAT CTG ATA GTC TAC AAG TAG CTC AGG ACC TTT GAA
         TAT TAG CAT GTA GAC TAT CAG ATG TTC ATC GAG TCC TGG AAA CTT
         <Tyr Asp Tyr Met Gln Tyr Asp Val Leu Leu Glu Pro Gly Lys Phe
         <___e___e___e___e___e___e_CKIIA___e___e___e___e___e___e__

1090           1100           1110           1120           1130
           *      *      *      *      *      *      *      *      *
         GTA TCG GGA AGC AAC TCG GAC ATT ATA TTC TTG GCC AGG ATG ATA
         CAT AGC CCT TCG TTG AGC CTG TAA TAT AAG AAC CGG TCC TAC TAT
         <Tyr Arg Ser Ala Val Arg Val Asn Tyr Glu Gln Gly Pro His Tyr
         <___e___e___e___e___e___e_CKIIA___e___e___e___e___e___e__

1140           1150           1160           1170
           *      *      *      *      *      *      *      *      *
         AAA CTC AGC CAA ACC CCA GTC TAT TAG TCG TAG CTT TCT GTG CTC
         TTT GAG TCG GTT TGG GGT CAG ATA ATC AGC ATC GAA AGA CAC GAG
         <Phe Glu Ala Leu Gly Trp Asp Ile Leu Arg Leu Lys Arg His Glu
         <___e___e___e___e___e___e_CKIIA___e___e___e___e___e___e__

1180           1190           1200           1210           1220
           *      *      *      *      *      *      *      *      *
         ATG ATC AAT CAT GAC ATT ATG GGG CTT GAC ATC TCT GTG CAT AAT
         TAC TAG TTA GTA CTG TAA TAC CCC GAA CTG TAG AGA CAC GTA TTA
         <His Asp Ile Met Val Asn His Pro Lys Val Asp Arg His Met Ile
         <___e___e___e___e___e___e_CKIIA___e___e___e___e___e___e__

1230           1240           1250           1260
           *      *      *      *      *      *      *      *      *
         TCC CAT GCT GTG ACA ATA ATC CAG GGC CTT CAG AAT CTC ATA CAT
         AGG GTA CGA CAC TGT TAT TAG GTC CCG GAA GTC TTA GAG TAT GTA
         <Gly Met Ser His Cys Tyr Asp Leu Ala Lys Leu Ile Glu Tyr Met
         <___e___e___e___e___e___e_CKIIA___e___e___e___e___e___e__
```

FIG. 8D

```
       1270         1280         1290          1300         1310
  *      *     *      *      *     *      *      *     *
GTA AAA TCG AAT ATC ATA GTC TGT TAA CGT CTG GTA CAA TTG CTT
CAT TTT AGC TTA TAG TAT CAG ACA ATT GCA GAC CAT GTT AAC GAA
<Tyr Phe Arg Ile Asp Tyr Asp Thr Leu Thr Gln Tyr Leu Gln Lys
<__e__e__e__e__e__e_CKIIA__e__e__e__e__e__e__

1320         1330          1340         1350
  *     *      *      *     *      *      *      *
GAA GTC TGT GTT GTT TAC GTG TTC AAA AAC CAA GGC GGG GGT TCG
CTT CAG ACA CAA CAA ATG CAC AAG TTT TTG GTT CCG CCC CCA AGC
<Phe Asp Thr Asn Asn Val His Glu Phe Val Leu Ala Pro Thr Arg
<__e__e__e__e__e__e_CKIIA__e__e__e__e__e__e__

1360         1370          1380         1390         1400
  *      *     *      *      *     *      *      *     *
TGA CAC AGG GTC TTT TAC AAT GTC TGC CAG TGT GAT GAT GTT GGG
ACT GTG TCC CAG AAA ATG TTA CAG ACG GTC ACA CTA CTA CAA CCC
<Ser Val Pro Asp Lys Val Ile Asp Ala Leu Thr Ile Ile Asn Pro
<__e__e__e__e__e__e_CKIIA__e__e__e__e__e__e__

1410         1420          1430         1440
  *     *      *      *     *      *      *      *
ACC TCC TCT CAA ATT CTC CAA AAT CTT TAT TTC ACG CTT AAT TTT
TGG AGG AGA GTT TAA GAG GTT TTA GAA ATA AAG TGC GAA TTA AAA
<Gly Gly Arg Leu Asn Glu Leu Ile Lys Ile Glu Arg Lys Ile Lys
<__e__e__e__e__e__e_CKIIA__e__e__e__e__e__e__

1450         1460          1470         1480         1490
  *      *     *      *      *     *      *      *     *
CTT CTT TTT TAC TGG CTT GAG AAT TTT AAC AAC AAC TTT TTC ATT
GAA GAA AAA ATG ACC GAA CTC TTA AAA TTG TTG TTG AAA AAG TAA
<Lys Lys Lys Val Pro Lys Leu Ile Lys Val Val Val Lys Glu Asn
<__e__e__e__e__e__e_CKIIA__e__e__e__e__e__e__

1500         1510          1520         1530
  *     *      *      *     *      *      *      *
ATT TGT GAT GTT GAT GGC TTC AAA TAC TTC ACT GTA TTT ACC TCG
TAA ACA CTA CAA CTA CCG AAG TTT ATG AAG TGA CAT AAA TGG AGC
<Asn Thr Ile Asn Ile Ala Glu Phe Val Glu Ser Tyr Lys Gly Arg
<__e__e__e__e__e__e_CKIIA__e__e__e__e__e__e__
```

FIG. 8E

```
         1540       1550       1560       1570       1580
           *    *    *    *    *    *    *    *    *
          GCC  TAA  TTT  TCG  AAC  CAG  CTG  GTA  GTC  ATC  TTG  ATT  TCC  CCA  TTC
          CGG  ATT  AAA  AGC  TTG  GTC  GAC  CAT  CAG  TAG  AAC  TAA  AGG  GGT  AAG
         <Gly  Leu  Lys  Arg  Val  Leu  Gln  Tyr  Asp  Asp  Gln  Asn  Gly  Trp  Glu
         <__e__e__e__e__e__e_CKIIA__e__e__e__e__e__e__

1590       1600       1610       1620
                *    *    *    *    *    *    *    *    *
               CAC  CAC  ATG  TGA  CTC  GTA  ATC  CCA  GTA  TTC  TCG  AGG  TCT  GTG  TGT
               GTG  GTG  TAC  ACT  GAG  CAT  TAG  GGT  CAT  AAG  AGC  TCC  AGA  CAC  ACA
              <Val  Val  His  Ser  Glu  Tyr  Asp  Trp  Tyr  Glu  Arg  Pro  Arg  His  Thr
              <__e__e__e__e__e__e_CKIIA__e__e__e__e__e__e__

1630       1640       1650       1660       1670
           *    *    *    *    *    *    *    *    *
          ATT  AAC  ATC  TGT  GTA  AAC  TCT  GGC  CCT  GCT  TGG  CAC  GGG  TCC  CGA
          TAA  TTG  TAG  ACA  CAT  TTG  AGA  CCG  GGA  CGA  ACC  GTG  CCC  AGG  GCT
         <Asn  Val  Asp  Thr  Tyr  Val  Arg  Ala  Arg  Ser  Pro  Val  Pro  Gly  Ser
         <__e__e__e__e__e__e_CKIIA__e__e__e__e__e__e__

1680        1690       1700       1710
                     *    *    *    *    *    *    *    *    *
                    CAT  ATGTA  TATCTCCTTC  TTGTCGAC  TTA  GCG  AAT  CGT  CTT  GAC  TGG
                    GTA  TACAT  ATAGAGGAAG  AACAGCTG  AAT  CGC  TTA  GCA  GAA  CTG  ACC
                                                    <***  Arg  Ile  Thr  Lys  Val  Pro
                                                    <__d__d_CKIIB__d__d__
         <Met
         <__

1720       1730       1740       1750       1760
           *    *    *    *    *    *    *    *    *
          GCT  CTT  GAA  GTT  GCT  GGC  GGC  TTG  GAG  CTG  CAG  CTG  GTA  GGC  CAT
          CGA  GAA  CTT  CAA  CGA  CCG  CCG  AAC  CTC  GAC  GTC  GAC  CAT  CCG  GTA
         <Ser  Lys  Phe  Asn  Ser  Ala  Ala  Gln  Leu  Gln  Leu  Gln  Tyr  Ala  Met
         <__d__d__d__d__d__d_CKIIB__d__d__d__d__d__d__

1770       1780       1790       1800
           *    *    *    *    *    *    *    *    *
          CGC  ATG  GAT  CTT  GAA  ACC  GTA  GAG  CCT  GGG  CAC  AAA  CTG  GTT  GGC
          GCG  TAC  CTA  GAA  CTT  TGG  CAT  CTC  GGA  CCC  GTG  TTT  GAC  CAA  CCG
         <Ala  His  Ile  Lys  Phe  Gly  Tyr  Leu  Arg  Pro  Val  Phe  Gln  Asn  Ala
         <__d__d__d__d__d__d_CKIIB__d__d__d__d__d__d__
```

FIG. 8F

```
       1810        1820        1830        1840        1850
         *           *           *           *           *
       AGG TCT CTT GGG CCG GTA CTC GGG ATG CAC CAT GAA GAG CAT GTG
       TCC AGA GAA CCC GGC CAT GAG CCC TAC GTG GTA CTT CTC GTA CAC
      <Pro Arg Lys Pro Trp Tyr Glu Pro His Val Met Phe Leu Met His
      <___d___d___d___d___d___d__CKIIB___d___d___d___d___d___d__

1860        1870        1880        1890
                *           *           *           *
       AGG GAA ACC AGT GCC GAA GTA GGC GCC ATC CGT GTG ATG GTG TCT
       TCC CTT TGG TCA CGG CTT CAT CCG CGG TAG GCA CAC TAC CAC AGA
      <Pro Phe Gly Thr Gly Phe Tyr Ala Gly Asp Thr His His His Arg
      <___d___d___d___d___d___d__CKIIB___d___d___d___d___d___d__

1900        1910        1920        1930        1940
         *           *           *           *           *
       TGA TGA CTT GGG TGT GTA CAC ATC CAT GCA CTT GGG GCA GTA GAG
       ACT ACT GAA CCC ACA CAT GTG TAG GTA CGT GAA CCC CGT CAT CTC
      <Ser Ser Lys Pro Thr Tyr Val Asp Met Cys Lys Pro Cys Tyr Leu
      <___d___d___d___d___d___d__CKIIB___d___d___d___d___d___d__

1950        1960        1970        1980
                *           *           *           *
       CTT CAC CAT GGC TTC ACC TGG GAT GTC TGA AAG GCC AAT GGG AAG
       GAA GTG GTA CCG AAG TGG ACC CTA CAG ACT TTC CGG TTA CCC TTC
      <Lys Val Met Ala Glu Gly Pro Ile Asp Ser Leu Gly Ile Pro Leu
      <___d___d___d___d___d___d__CKIIB___d___d___d___d___d___d__

1990        2000        2010        2020        2030
         *           *           *           *           *
       CAT TGG CTG GTT CTC ACA GTA CAC ACG AGG ACA GTA ACC AAA GTC
       GTA ACC GAC CAA GAG TGT CAT GTG TGC TCC TGT CAT TGG TTT CAG
      <Met Pro Gln Asn Glu Cys Tyr Val Arg Pro Cys Tyr Gly Phe Asp
      <___d___d___d___d___d___d__CKIIB___d___d___d___d___d___d__

2040        2050        2060        2070
                *           *           *           *
       TCC TTG CTG GTA CTT TTC CAA CAT CTG GGC GAT GCC ACG GTT GGT
       AGG AAC GAC CAT GAA AAG GTT GTA GAC CCG CTA CGG TGC CAA CCA
      <Gly Gln Gln Tyr Lys Glu Leu Met Gln Ala Ile Gly Arg Asn Thr
      <___d___d___d___d___d___d__CKIIB___d___d___d___d___d___d__
```

FIG. 8G

```
       2080        2090        2100        2110        2120
         *           *           *           *           *
       AAG GAT GTA GCG GGC GTG GAT CAA TCC ATA AAG CAT CTC GGC TGC
       TTC CTA CAT CGC CCG CAC CTA GTT AGG TAT TTC GTA GAG CCG ACG
      <Leu Ile Tyr Arg Ala His Ile Leu Gly Tyr Leu Met Glu Ala Ala
      <__d__d__d__d__d__d_CKIIB___d__d__d__d__d__d__

2130        2140        2150        2160
                *           *           *           *
            CTG CTC AAT CAG GTC ACT CTG GTT GGG GTT GTC TTC CAG TTC TTC
            GAC GAG TTA GTC CAG TGA GAC CAA CCC CAA CAG AAG GTC AAG AAG
           <Gln Glu Ile Leu Asp Ser Gln Asn Pro Asn Asp Glu Leu Glu Glu
           <__d__d__d__d__d__d_CKIIB___d__d__d__d__d__d__

2170        2180        2190        2200        2210
         *           *           *           *           *
       ATC AGG CTC CAG GTC CAA GAT CAT GTC TAG AGC TTG TCG GTA GTG
       TAG TCC GAG GTC CAG GTT CTA GTA CAG ATC TCG AAC AGC CAT CAC
      <Asp Pro Glu Leu Asp Leu Ile Met Asp Leu Ala Gln Arg Tyr His
      <__d__d__d__d__d__d_CKIIB___d__d__d__d__d__d__

2220        2230        2240        2250
                *           *           *           *
            AGG GAC CTG CTC ATT GAG TCC AGT AAG ATT AAA TTT GTC CTG GAT
            TCC CTG GAC GAG TAA CTC AGG TCA TTC TAA TTT AAA CAG GAC CTA
           <Pro Val Gln Glu Asn Leu Gly Thr Leu Asn Phe Lys Asp Gln Ile
           <__d__d__d__d__d__d_CKIIB___d__d__d__d__d__d__

2260        2270        2280        2290        2300
         *           *           *           *           *
       GTA GTC TTC ATC CAC TTC ACA GAA GAA TTC ATT GCC ACG GAG CCC
       CAT CAG AAG TAG GTG AAG TGT CTT CTT AAG TAA CGG TGC CTC GGG
      <Tyr Asp Glu Asp Val Glu Cys Phe Phe Glu Asn Gly Arg Leu Gly
      <__d__d__d__d__d__d_CKIIB___d__d__d__d__d__d__

2310        2320        2330        2340        2350
                *           *           *           *           *
            ACA GAA CCA GGA AAT CCA GGA CAC CTC CTC TGA GCT GCT CAT ATGT
            TGT CTT GGT CCT TTA GGT CCT GTG GAG GAG ACT CGA CGA GTA TACA
           <Cys Phe Trp Ser Ile Trp Ser Val Glu Glu Ser Ser Ser Met
           <__d__d__d__d__d_____CKIIB_d__d__d__d__d__d__
```

FIG. 8H

```
           2360       2370       2380       2390       2400
            *   *      *   *      *   *      *   *      *   *
        TATTCCTCCT TATTTAATCG ATCCGGATAT AGTTCCTCCT TTCAGCAAAA
        ATAAGGAGGA ATAAATTAGC TAGGCCTATA TCAAGGAGGA AAGTCGTTTT
                                                    <____

2410       2420       2430       2440       2450
            *   *      *   *      *   *      *   *      *   *
        AACCCCTCAA GACCCGTTTA GAGGCCCCAA GGGGTTATGC TAGTTATTGC
        TTGGGGAGTT CTGGGCAAAT CTCCGGGGTT CCCCAATACG ATCAATAACG
        <_____h_____T7 TERMINATOR___h_____h__

2460       2470       2480       2490       2500
            *   *      *   *      *   *      *   *      *   *
        TCAGCGGTGG CAGCAGCCAA CTCAGCTTCC TTTCGGGCTT TGTTAGCAGC
        AGTCGCCACC GTCGTCGGTT GAGTCGAAGG AAAGCCCGAA ACAATCGTCG 2510        2520        2530        2540
            *   *   *    *    *    *    *    *    *
        CGGATCC TTA TTA GAC ACT AAT GGG GTT ATG AAC TGG GGC AAG TGG
        GCCTAGG AAT AAT CTG TGA TTA CCC CAA TAC TTG ACC CCG TTC ACC
                <*** *** Val Ser Ile Pro Asn His Val Pro Ala Leu Pro
                    <__k__k__k__k__k__HBCN ___k__k__k__k__k___

2550        2560        2570        2580        2590
            *     *      *     *     *     *     *     *     *
        CTG AGT CAC AGG GTA GAT CTG GTG GGT GGG GTT AAG TAG AAG TTC
        GAC TCA GTG TCC CAT CTA GAC CAC CCA CCC CAA TTC ATC TTC AAG
        <Gln Thr Val Pro Tyr Ile Gln His Thr Pro Asn Leu Leu Leu Glu
        <__k__k__k__k__k__k__HBCN ___k__k__k__k__k__k__

2600        2610        2620        2630
            *     *     *     *     *     *     *     *
        TTG GTT GAG CAG AAG GGC TTG AAC AGG CAC AGC TCT CTG AGG GTA
        AAC CAA CTC GTC TTC CCG AAC TTG TCC GTG TCG AGA GAC TCC CAT
        <Gln Asn Leu Leu Leu Ala Gln Val Pro Val Ala Arg Gln Pro Tyr
        <__k__k__k__k__k__k__HBCN ___k__k__k__k__k__k__

2640        2650        2660        2670        2680
            *     *     *     *     *     *     *     *     *
        GGG CAC CAC TTG CTG GGG GAT AGG CAG GAC TTT GGG CTG AGG AAC
        CCC GTG GTG AAC GAC CCC CTA TCC GTC CTG AAA CCC GAC TCC TTG
        <Pro Val Val Gln Gln Pro Ile Pro Leu Val Lys Pro Gln Pro Val
        <__k__k__k__k__k__k__HBCN ___k__k__k__k__k__k__
```

FIG. 81

```
              2690          2700          2710          2720
               *     *     *     *     *     *     *     *     *
         AGA CCA CAG GGG CTG AGG GGG AAG TGC AAG AGT CTG AGG AAT AGG
         TCT GGT GTC CCC GAC TCC CCC TTC ACG TTC TCA GAC TCC TTA TCC
        <Ser Trp Leu Pro Gln Pro Pro Leu Ala Leu Thr Gln Pro Ile Pro
        <___k___k___k___k___k___k_HBCN ____k___k___k___k___k___k___

2730          2740          2750          2760          2770
               *     *     *     *     *     *     *     *     *     *
         CTG AGG GAC CTG CTG CAT CAA GGG CTG GAG CAG AGG CAG AGG AAG
         GAC TCC CTG GAC GAC GTA GTT CCC GAC CTC GTC TCC GTC TCC TTC
        <Gln Pro Val Gln Gln Met Leu Pro Gln Leu Leu Pro Leu Pro Leu
        <___k___k___k___k___k___k_HBCN ____k___k___k___k___k___k___

2780          2790          2800          2810
                     *     *     *     *     *     *     *     *     *
         ATG CAG ATT TTC AAG ATC AGT GAG TTT TGG GAT TTG AGG GTC AAA
         TAC GTC TAA AAG TTC TAG TCA CTC AAA ACC CTA AAC TCC CAG TTT
        <His Leu Asn Glu Leu Asp Thr Leu Lys Pro Ile Gln Pro Asp Phe
        <___k___k___k___k___k___k_HBCN ____k___k___k___k___k___k___

2820          2830          2840          2850          2860
               *     *     *     *     *     *     *     *     *
         AAA GGG TAT CGT TGG AGA TTT AAG GAC AGG CAT CAC TCT GCC CTT
         TTT CCC ATA GCA ACC TCT AAA TTC CTG TCC GTA GTG AGA CGG GAA
        <Phe Pro Ile Thr Pro Ser Lys Leu Val Pro Met Val Arg Gly Lys
        <___k___k___k___k___k___k_HBCN ____k___k___k___k___k___k___

2870          2880          2890          2900
                     *     *     *     *     *     *     *     *     *
         AGT GTA GAC AGT GTC TTT AGC TTT AGG GAC TTC CAT TAT TTC AGG
         TCA CAT CTG TCA CAG AAA TCG AAA TCC CTG AAG GTA ATA AAG TCC
        <Thr Tyr Val Thr Asp Lys Ala Lys Pro Val Glu Met Ile Glu Pro
        <___k___k___k___k___k___k_HBCN ____k___k___k___k___k___k___

2910          2920          2930          2940          2950
               *     *     *     *     *     *     *     *     *
         CTG AGG GAC AGG CAG CAC CAC AGC AGG CTG AGC AAG AGG CAG AAT
         GAC TCC CTG TCC GTC GTG GTG TCG TCC GAC TCG TTC TCC GTC TTA
        <Gln Pro Val Pro Leu Val Val Ala Pro Gln Ala Leu Pro Leu Ile
        <___k___k___k___k___k___k_HBCN ____k___k___k___k___k___k___
```

FIG. 8J

```
            2960        2970        2980        2990
              *     *     *     *     *     *     *     *     *
            GTT   TTG   TGG   AAG   AAA   ACC   ATA   GGG   GAT   AGG   TTC   AAC   GAA   TGG   ATA
            CAA   AAC   ACC   TTC   TTT   TGG   TAT   CCC   CTA   TCC   AAG   TTG   CTT   ACC   TAT
           <Asn   Gln   Pro   Leu   Phe   Gly   Tyr   Pro   Ile   Pro   Glu   Val   Phe   Pro   Tyr
           <___k___k___k___k___k___k_HBCN ___k___k___k___k___k___k___

3000        3010        3020        3030        3040
              *     *     *     *     *     *     *     *     *
            GAT   CAG   AGG   CTG   TGG   CTG   GAA   AGA   GGG   GTA   GAT   TTT   ATC   CTG   GTG
            CTA   GTC   TCC   GAC   ACC   GAC   CTT   TCT   CCC   CAT   CTA   AAA   TAG   GAC   CAC
           <Ile   Leu   Pro   Gln   Pro   Gln   Phe   Ser   Pro   Tyr   Ile   Lys   Asp   Gln   His
           <___k___k___k___k___k___k_HBCN ___k___k___k___k___k___k___

3050        3060        3070        3080
              *     *     *     *     *     *     *     *     *
            TTC   ATC   CTC   TCC   TTG   CTG   CTG   GTC   CTC   GTG   TTT   AAC   TTT   TTC   AAC
            AAG   TAG   GAG   AGG   AAC   GAC   GAC   CAG   GAG   CAC   AAA   TTG   AAA   AAG   TTG
           <Glu   Asp   Glu   Gly   Gln   Gln   Gln   Asp   Glu   His   Lys   Val   Lys   Glu   Val
           <___k___k___k___k___k___k_HBCN ___k___k___k___k___k___k___

3090        3100        3110        3120        3130
              *     *     *     *     *     *     *     *     *
            TTT   CTG   TTT   GTA   TTC   GGT   GAT   CGA   TTC   TTC   GCT   CGA   GCT   CAG   GGA
            AAA   GAC   AAA   CAT   AAG   CCA   CTA   GCT   AAG   AAG   CGA   GCT   CGA   GTC   CCT
           <Lys   Gln   Lys   Tyr   Glu   Thr   Ile   Ser   Glu   Glu   Ser   Ser   Ser   Leu   Ser
           <___k___k___k___k___k___k_HBCN ___k___k___k___k___k___k___

3140        3150        3160        3170        3180
              *     *     *     *     *     *     *     *     *     *
            TTC   GAT   GGT   TTC   ACG   TGG   CAT   ATGTATAT   CTCCTTCTTA   AAGTTAAACA
            AAG   CTA   CCA   AAG   TGC   ACC   GTA   TACATATA   GAGGAAGAAT   TTCAATTTGT
           <Glu   Ile   Thr   Glu   Arg   Pro   Met
           <___k___k_HBCN ___k___k___

3190        3200        3210        3220        3230
              *     *     *     *     *     *     *     *     *     *
            AAATTATTTC   TAGAGGGAAA   CCGTTGTGGT   CTCCCTATAG   TGAGTCGTAT
            TTTAATAAAG   ATCTCCCTTT   GGCAACACCA   GAGGGATATC   ACTCAGCATA
                                                             <___T7 PROMOT___

3240        3250        3260        3270        3280
              *     *     *     *     *     *     *     *     *     *
            TAATTTCGCG   GGATCGAGAT   CTCGATCCTC   TACGCCGGAC   GCATCGTGGC
            ATTAAAGCGC   CCTAGCTCTA   GAGCTAGGAG   ATGCGGCCTG   CGTAGCACCG
           <__
```

FIG. 8K

```
         3290       3300       3310       3320       3330
          *  *       *  *       *  *       *  *       *  *
     CGGCATCACC GGCGCCACAG GTGCGGTTGC TGGCGCCTAT ATCGCCGACA
     GCCGTAGTGG CCGCGGTGTC CACGCCAACG ACCGCGGATA TAGCGGCTGT 3340       3350       3360       3370       3380
          *  *       *  *       *  *       *  *       *  *
     TCACCGATGG GGAAGATCGG GCTCGCCACT TCGGGCTCAT GAGCGCTTGT
     AGTGGCTACC CCTTCTAGCC CGAGCGGTGA AGCCCGAGTA CTCGCGAACA 3390       3400       3410       3420       3430
          *  *       *  *       *  *       *  *       *  *
     TTCGGCGTGG GTATGGTGGC AGGCCCCGTG GCCGGGGGAC TGTTGGGCGC
     AAGCCGCACC CATACCACCG TCCGGGGCAC CGGCCCCCTG ACAACCCGCG 3440       3450       3460       3470       3480
          *  *       *  *       *  *       *  *       *  *
     CATCTCCTTG CATGCACCAT TCCTTGCGGC GGCGGTGCTC AACGGCCTCA
     GTAGAGGAAC GTACGTGGTA AGGAACGCCG CCGCCACGAG TTGCCGGAGT 3490       3500       3510       3520       3530
          *  *       *  *       *  *       *  *       *  *
     ACCTACTACT GGGCTGCTTC CTAATGCAGG AGTCGCATAA GGGAGAGCGT
     TGGATGATGA CCCGACGAAG GATTACGTCC TCAGCGTATT CCCTCTCGCA 3540       3550       3560       3570       3580
          *  *       *  *       *  *       *  *       *  *
     CGACCGATGC CCTTGAGAGC CTTCAACCCA GTCAGCTCCT TCCGGTGGGC
     GCTGGCTACG GGAACTCTCG GAAGTTGGGT CAGTCGAGGA AGGCCACCCG 3590       3600       3610       3620       3630
          *  *       *  *       *  *       *  *       *  *
     GCGGGGCATG ACTATCGTCG CCGCACTTAT GACTGTCTTC TTTATCATGC
     CGCCCCGTAC TGATAGCAGC GGCGTGAATA CTGACAGAAG AAATAGTACG 3640       3650       3660       3670       3680
          *  *       *  *       *  *       *  *       *  *
     AACTCGTAGG ACAGGTGCCG GCAGCGCTCT GGGTCATTTT CGGCGAGGAC
     TTGAGCATCC TGTCCACGGC CGTCGCGAGA CCCAGTAAAA GCCGCTCCTG 3690       3700       3710       3720       3730
          *  *       *  *       *  *       *  *       *  *
     CGCTTTCGCT GGAGCGCGAC GATGATCGGC CTGTCGCTTG CGGTATTCGG
     GCGAAAGCGA CCTCGCGCTG CTACTAGCCG GACAGCGAAC GCCATAAGCC
```

FIG. 8L

```
      3740       3750       3760       3770       3780
        *          *          *          *          *
   AATCTTGCAC GCCCTCGCTC AAGCCTTCGT CACTGGTCCC GCCACCAAAC
   TTAGAACGTG CGGGAGCGAG TTCGGAAGCA GTGACCAGGG CGGTGGTTTG 3790       3800       3810       3820       3830
        *          *          *          *          *
   GTTTCGGCGA GAAGCAGGCC ATTATCGCCG GCATGGCGGC CGACGCGCTG
   CAAAGCCGCT CTTCGTCCGG TAATAGCGGC CGTACCGCCG GCTGCGCGAC 3840       3850       3860       3870       3880
        *          *          *          *          *
   GGCTACGTCT TGCTGGCGTT CGCGACGCGA GGCTGGATGG CCTTCCCCAT
   CCGATGCAGA ACGACCGCAA GCGCTGCGCT CCGACCTACC GGAAGGGGTA 3890       3900       3910       3920       3930
        *          *          *          *          *
   TATGATTCTT CTCGCTTCCG GCGGCATCGG GATGCCCGCG TTGCAGGCCA
   ATACTAAGAA GAGCGAAGGC CGCCGTAGCC CTACGGGCGC AACGTCCGGT 3940       3950       3960       3970       3980
        *          *          *          *          *
   TGCTGTCCAG GCAGGTAGAT GACGACCATC AGGGACAGCT TCAAGGATCG
   ACGACAGGTC CGTCCATCTA CTGCTGGTAG TCCCTGTCGA AGTTCCTAGC 3990       4000       4010       4020       4030
        *          *          *          *          *
   CTCGCGGCTC TTACCAGCCT AACTTCGATC ACTGGACCGC TGATCGTCAC
   GAGCGCCGAG AATGGTCGGA TTGAAGCTAG TGACCTGGCG ACTAGCAGTG 4040       4050       4060       4070       4080
        *          *          *          *          *
   GGCGATTTAT GCCGCCTCGG CGAGCACATG GAACGGGTTG GCATGGATTG
   CCGCTAAATA CGGCGGAGCC GCTCGTGTAC CTTGCCCAAC CGTACCTAAC 4090       4100       4110       4120       4130
        *          *          *          *          *
   TAGGCGCCGC CCTATACCTT GTCTGCCTCC CCGCGTTGCG TCGCGGTGCA
   ATCCGCGGCG GGATATGGAA CAGACGGAGG GGCGCAACGC AGCGCCACGT 4140       4150       4160       4170       4180
        *          *          *          *          *
   TGGAGCCGGG CCACCTCGAC CTGAATGGAA GCCGGCGGCA CCTCGCTAAC
   ACCTCGGCCC GGTGGAGCTG GACTTACCTT CGGCCGCCGT GGAGCGATTG
```

FIG. 8M

```
        4190       4200       4210       4220       4230
          *  *       *  *       *  *       *  *       *  *
       GGATTCACCA CTCCAAGAAT TGGAGCCAAT CAATTCTTGC GGAGAACTGT
       CCTAAGTGGT GAGGTTCTTA ACCTCGGTTA GTTAAGAACG CCTCTTGACA 4240       4250       4260       4270       4280
          *  *       *  *       *  *       *  *       *  *
       GAATGCGCAA ACCAACCCTT GGCAGAACAT ATCCATCGCG TCCGCCATCT
       CTTACGCGTT TGGTTGGGAA CCGTCTTGTA TAGGTAGCGC AGGCGGTAGA 4290       4300       4310       4320       4330
          *  *       *  *       *  *       *  *       *  *
       CCAGCAGCCG CACGCGGCGC ATCTCGGGCA GCGTTGGGTC CTGGCCACGG
       GGTCGTCGGC GTGCGCCGCG TAGAGCCCGT CGCAACCCAG GACCGGTGCC 4340       4350       4360       4370       4380
          *  *       *  *       *  *       *  *       *  *
       GTGCGCATGA TCGTGCTCCT GTCGTTGAGG ACCCGGCTAG GCTGGCGGGG
       CACGCGTACT AGCACGAGGA CAGCAACTCC TGGGCCGATC CGACCGCCCC 4390       4400       4410       4420       4430
          *  *       *  *       *  *       *  *       *  *
       TTGCCTTACT GGTTAGCAGA ATGAATCACC GATACGCGAG CGAACGTGAA
       AACGGAATGA CCAATCGTCT TACTTAGTGG CTATGCGCTC GCTTGCACTT 4440       4450       4460       4470       4480
          *  *       *  *       *  *       *  *       *  *
       GCGACTGCTG CTGCAAAACG TCTGCGACCT GAGCAACAAC ATGAATGGTC
       CGCTGACGAC GACGTTTTGC AGACGCTGGA CTCGTTGTTG TACTTACCAG 4490       4500       4510       4520       4530
          *  *       *  *       *  *       *  *       *  *
       TTCGGTTTCC GTGTTTCGTA AAGTCTGGAA ACGCGGAAGT CAGCGCCCTG
       AAGCCAAAGG CACAAAGCAT TTCAGACCTT TGCGCCTTCA GTCGCGGGAC 4540       4550       4560       4570       4580
          *  *       *  *       *  *       *  *       *  *
       CACCATTATG TTCCGGATCT GCATCGCAGG ATGCTGCTGG CTACCCTGTG
       GTGGTAATAC AAGGCCTAGA CGTAGCGTCC TACGACGACC GATGGGACAC 4590       4600       4610       4620       4630
          *  *       *  *       *  *       *  *       *  *
       GAACACCTAC ATCTGTATTA ACGAAGCGCT GGCATTGACC CTGAGTGATT
       CTTGTGGATG TAGACATAAT TGCTTCGCGA CCGTAACTGG GACTCACTAA
```

FIG. 8N

```
           4640       4650       4660       4670       4680
            *  *       *  *       *  *       *  *       *  *
        TTTCTCTGGT CCCGCCGCAT CCATACCGCC AGTTGTTTAC CCTCACAACG
        AAAGAGACCA GGGCGGCGTA GGTATGGCGG TCAACAAATG GGAGTGTTGC 4690       4700       4710       4720       4730
            *  *       *  *       *  *       *  *       *  *
        TTCCAGTAAC CGGGCATGTT CATCATCAGT AACCCGTATC GTGAGCATCC
        AAGGTCATTG GCCCGTACAA GTAGTAGTCA TTGGGCATAG CACTCGTAGG 4740       4750       4760       4770       4780
            *  *       *  *       *  *       *  *       *  *
        TCTCTCGTTT CATCGGTATC ATTACCCCCA TGAACAGAAA TCCCCCTTAC
        AGAGAGCAAA GTAGCCATAG TAATGGGGGT ACTTGTCTTT AGGGGGAATG 4790       4800       4810       4820       4830
            *  *       *  *       *  *       *  *       *  *
        ACGGAGGCAT CAGTGACCAA ACAGGAAAAA ACCGCCCTTA ACATGGCCCG
        TGCCTCCGTA GTCACTGGTT TGTCCTTTTT TGGCGGGAAT TGTACCGGGC 4840       4850       4860       4870       4880
            *  *       *  *       *  *       *  *       *  *
        CTTTATCAGA AGCCAGACAT TAACGCTTCT GGAGAAACTC AACGAGCTGG
        GAAATAGTCT TCGGTCTGTA ATTGCGAAGA CCTCTTTGAG TTGCTCGACC 4890       4900       4910       4920       4930
            *  *       *  *       *  *       *  *       *  *
        ACGCGGATGA ACAGGCAGAC ATCTGTGAAT CGCTTCACGA CCACGCTGAT
        TGCGCCTACT TGTCCGTCTG TAGACACTTA GCGAAGTGCT GGTGCGACTA 4940       4950       4960       4970       4980
            *  *       *  *       *  *       *  *       *  *
        GAGCTTTACC GCAGCTGCCT CGCGCGTTTC GGTGATGACG GTGAAAACCT
        CTCGAAATGG CGTCGACGGA GCGCGCAAAG CCACTACTGC CACTTTTGGA 4990       5000       5010       5020       5030
            *  *       *  *       *  *       *  *       *  *
        CTGACACATG CAGCTCCCGG AGACGGTCAC AGCTTGTCTG TAAGCGGATG
        GACTGTGTAC GTCGAGGGCC TCTGCCAGTG TCGAACAGAC ATTCGCCTAC 5040       5050       5060       5070       5080
            *  *       *  *       *  *       *  *       *  *
        CCGGGAGCAG ACAAGCCCGT CAGGGCGCGT CAGCGGGTGT TGGCGGGTGT
        GGCCCTCGTC TGTTCGGGCA GTCCCGCGCA GTCGCCCACA ACCGCCCACA
```

FIG. 80

```
          5090       5100       5110       5120       5130
            *          *          *          *          *
       CGGGGCCCAG CCATGACCCA GTCACGTAGC GATAGCGGAG TGTATACTGG
       GCCCCGCGTC GGTACTGGGT CAGTGCATCG CTATCGCCTC ACATATGACC 5140       5150       5160       5170       5180
            *          *          *          *          *
       CTTAACTATG CGGCATCAGA GCAGATTGTA CTGAGAGTGC ACCATATATG
       GAATTGATAC GCCGTAGTCT CGTCTAACAT GACTCTCACG TGGTATATAC 5190       5200       5210       5220       5230
            *          *          *          *          *
       CGGTGTGAAA TACCGCACAG ATGCGTAAGG AGAAAATACC GCATCAGGCG
       GCCACACTTT ATGGCGTGTC TACGCATTCC TCTTTTATGG CGTAGTCCGC 5240       5250       5260       5270       5280
            *          *          *          *          *
       CTCTTCCGCT TCCTCGCTCA CTGACTCGCT GCGCTCGGTC GTTCGGCTGC
       GAGAAGGCGA AGGAGCGAGT GACTGAGCGA CGCGAGCCAG CAAGCCGACG 5290       5300       5310       5320       5330
            *          *          *          *          *
       GGCGAGCGGT ATCAGCTCAC TCAAAGGCGG TAATACGGTT ATCCACAGAA
       CCGCTCGCCA TAGTCGAGTG AGTTTCCGCC ATTATGCCAA TAGGTGTCTT 5340       5350       5360       5370       5380
            *          *          *          *          *
       TCAGGGGATA ACGCAGGAAA GAACATGTGA GCAAAAGGCC AGCAAAAGGC
       AGTCCCCTAT TGCGTCCTTT CTTGTACACT CGTTTTCCGG TCGTTTTCCG 5390       5400       5410       5420       5430
            *          *          *          *          *
       CAGGAACCGT AAAAAGGCCG CGTTGCTGGC GTTTTTCCAT AGGCTCCGCC
       GTCCTTGGCA TTTTTCCGGC GCAACGACCG CAAAAAGGTA TCCGAGGCGG
                                                  <_____ORI_____

5440       5450       5460       5470       5480
            *          *          *          *          *
       CCCCTGACGA GCATCACAAA AATCGACGCT CAAGTCAGAG GTGGCGAAAC
       GGGGACTGCT CGTAGTGTTT TTAGCTGCGA GTTCAGTCTC CACCGCTTTG
       <_____ORI_____i_

5490       5500       5510       5520       5530
            *          *          *          *          *
       CCGACAGGAC TATAAAGATA CCAGGCGTTT CCCCCTGGAA GCTCCCTCGT
       GGCTGTCCTG ATATTTCTAT GGTCCGCAAA GGGGGACCTT CGAGGGAGCA
```

FIG. 8P

```
          5540       5550       5560       5570       5580
           *  *       *  *       *  *       *  *       *  *
     GCGCTCTCCT GTTCCGACCC TGCCGCTTAC CGGATACCTG TCCGCCTTTC
     CGCGAGAGGA CAAGGCTGGG ACGGCGAATG GCCTATGGAC AGGCGGAAAG 5590       5600       5610       5620       5630
           *  *       *  *       *  *       *  *       *  *
     TCCCTTCGGG AAGCGTGGCG CTTTCTCATA GCTCACGCTG TAGGTATCTC
     AGGGAAGCCC TTCGCACCGC GAAAGAGTAT CGAGTGCGAC ATCCATAGAG 5640       5650       5660       5670       5680
           *  *       *  *       *  *       *  *       *  *
     AGTTCGGTGT AGGTCGTTCG CTCCAAGCTG GGCTGTGTGC ACGAACCCCC
     TCAAGCCACA TCCAGCAAGC GAGGTTCGAC CCGACACACG TGCTTGGGGG 5690       5700       5710       5720       5730
           *  *       *  *       *  *       *  *       *  *
     CGTTCAGCCC GACCGCTGCG CCTTATCCGG TAACTATCGT CTTGAGTCCA
     GCAAGTCGGG CTGGCGACGC GGAATAGGCC ATTGATAGCA GAACTCAGGT 5740       5750       5760       5770       5780
           *  *       *  *       *  *       *  *       *  *
     ACCCGGTAAG ACACGACTTA TCGCCACTGG CAGCAGCCAC TGGTAACAGG
     TGGGCCATTC TGTGCTGAAT AGCGGTGACC GTCGTCGGTG ACCATTGTCC 5790       5800       5810       5820       5830
           *  *       *  *       *  *       *  *       *  *
     ATTAGCAGAG CGAGGTATGT AGGCGGTGCT ACAGAGTTCT TGAAGTGGTG
     TAATCGTCTC GCTCCATACA TCCGCCACGA TGTCTCAAGA ACTTCACCAC 5840       5850       5860       5870       5880
           *  *       *  *       *  *       *  *       *  *
     GCCTAACTAC GGCTACACTA GAAGGACAGT ATTTGGTATC TGCGCTCTGC
     CGGATTGATG CCGATGTGAT CTTCCTGTCA TAAACCATAG ACGCGAGACG 5890       5900       5910       5920       5930
           *  *       *  *       *  *       *  *       *  *
     TGAAGCCAGT TACCTTCGGA AAAAGAGTTG GTAGCTCTTG ATCCGGCAAA
     ACTTCGGTCA ATGGAAGCCT TTTTCTCAAC CATCGAGAAC TAGGCCGTTT 5940       5950       5960       5970       5980
           *  *       *  *       *  *       *  *       *  *
     CAAACCACCG CTGGTAGCGG TGGTTTTTTT GTTTGCAAGC AGCAGATTAC
     GTTTGGTGGC GACCATCGCC ACCAAAAAAA CAAACGTTCG TCGTCTAATG
```

FIG. 8Q

```
              5990       6000       6010       6020       6030
                *    *    *    *    *    *    *    *    *    *
           GCGCAGAAAA AAAGGATCTC AAGAAGATCC TTTGATCTTT TCTACGGGGT
           CGCGTCTTTT TTTCCTAGAG TTCTTCTAGG AAACTAGAAA AGATGCCCCA 6040       6050       6060       6070       6080
                *    *    *    *    *    *    *    *    *    *
           CTGACGCTCA GTGGAACGAA AACTCACGTT AAGGGATTTT GGTCATGAAC
           GACTGCGAGT CACCTTGCTT TTGAGTGCAA TTCCCTAAAA CCAGTACTTG 6090       6100       6110       6120       6130
                *    *    *    *    *    *    *    *    *    *
           AATAAAACTG TCTGCTTACA TAAACAGTAA TACAAGGGGT GTT ATG AGC CAT
           TTATTTTGAC AGACGAATGT ATTTGTCATT ATGTTCCCCA CAA TAC TCG GTA
                                                       Met Ser His>
                                                         __j__j__>

6140       6150       6160       6170
                *    *    *    *    *    *    *    *    *
           ATT CAA CGG GAA ACG TCT TGC TCG AGG CCG CGA TTA AAT TCC AAC
           TAA GTT GCC CTT TGC AGA ACG AGC TCC GGC GCT AAT TTA AGG TTG
           Ile Gln Trp Glu Thr Ser Cys Ser Arg Pro Arg Leu Asn Ser Asn>
           __j__j__j__j__j__j__KANR__j__j__j__j__j__j__>

6180       6190       6200       6210       6220
             *    *    *    *    *    *    *    *    *    *
           ATG GAT GCT GAT TTA TAT GGG TAT AAA TGG GCT CGC GAT AAT GTC
           TAC CTA CGA CTA AAT ATA CCC ATA TTT ACC CGA GCG CTA TTA CAG
           Met Asp Ala Asp Leu Tyr Gly Tyr Lys Trp Ala Arg Asp Asn Val>
           __j__j__j__j__j__j__KANR__j__j__j__j__j__j__>

6230       6240       6250       6260
             *    *    *    *    *    *    *    *    *
           GGG CAA TCA GGT GCG ACA ATC TAT CGA TTG TAT GGG AAG CCC GAT
           CCC GTT AGT CCA CGC TGT TAG ATA GCT AAC ATA CCC TTC GGG CTA
           Gly Gln Ser Gly Ala Thr Ile Tyr Arg Leu Tyr Gly Lys Pro Asp>
           __j__j__j__j__j__j__KANR__j__j__j__j__j__j__>

6270       6280       6290       6300       6310
             *    *    *    *    *    *    *    *    *    *
           GCG CCA GAG TTG TTT CTG AAA CAT GGC AAA GGT AGC GTT GCC AAT
           CGC GGT CTC AAC AAA GAC TTT GTA CCG TTT CCA TCG CAA CGG TTA
           Ala Pro Glu Leu Phe Leu Lys His Gly Lys Gly Ser Val Ala Asn>
           __j__j__j__j__j__j__KANR__j__j__j__j__j__j__>
```

FIG. 8R

```
              6320        6330        6340        6350
               *     *     *     *     *     *     *     *     *
              GAT GTT ACA GAT GAG ATG GTC AGA CTA AAC TGG CTG ACG GAA TTT
              CTA CAA TGT CTA CTC TAC CAG TCT GAT TTG ACC GAC TGC CTT AAA
              Asp Val Thr Asp Glu Met Val Arg Leu Asn Trp Leu Thr Glu Phe>
              ___j___j___j___j___j___j___KANR___j___j___j___j___j___j___>

6360        6370        6380        6390        6400
            *     *     *     *     *     *     *     *     *     *
           ATG CCT CTT CCG ACC ATC AAG CAT TTT ATC CGT ACT CCT GAT GAT
           TAC GGA GAA GGC TGG TAG TTC GTA AAA TAG GCA TGA GGA CTA CTA
           Met Pro Leu Pro Thr Ile Lys His Phe Ile Arg Thr Pro Asp Asp>
           ___j___j___j___j___j___j___KANR___j___j___j___j___j___j___>

6410        6420        6430        6440
            *     *     *     *     *     *     *     *     *
           GCA TGG TTA CTC ACC ACT GCG ATC CCC GGG AAA ACA GCA TTC CAG
           CGT ACC AAT GAG TGG TGA CGC TAG GGG CCC TTT TGT CGT AAG GTC
           Ala Trp Leu Leu Thr Thr Ala Ile Pro Gly Lys Thr Ala Phe Gln>
           ___j___j___j___j___j___j___KANR___j___j___j___j___j___j___>

6450        6460        6470        6480        6490
            *     *     *     *     *     *     *     *     *
           GTA TTA GAA GAA TAT CCT GAT TCA GGT GAA AAT ATT GTT GAT GCG
           CAT AAT CTT CTT ATA GGA CTA AGT CCA CTT TTA TAA CAA CTA CGC
           Val Leu Glu Glu Tyr Pro Asp Ser Gly Glu Asn Ile Val Asp Ala>
           ___j___j___j___j___j___j___KANR___j___j___j___j___j___j___>

6500        6510        6520        6530
            *     *     *     *     *     *     *     *     *
           CTG GCA GTG TTC CTG CGC CGG TTG CAT TCG ATT CCT GTT TGT AAT
           GAC CGT CAC AAG GAC GCG GCC AAC GTA AGC TAA GGA CAA ACA TTA
           Leu Ala Val Phe Leu Arg Trp Leu His Ser Ile Pro Val Cys Asn>
           ___j___j___j___j___j___j___KANR___j___j___j___j___j___j___>

6540        6550        6560        6570        6580
            *     *     *     *     *     *     *     *     *
           TGT CCT TTT AAC AGC GAT CGC GTA TTT CGT CTC GCT CAG GCG CAA
           ACA GGA AAA TTG TCG CTA GCG CAT AAA GCA GAG CGA GTC CGC GTT
           Cys Pro Phe Asn Ser Asp Arg Val Phe Arg Leu Ala Gln Ala Gln>
           ___j___j___j___j___j___j___KANR___j___j___j___j___j___j___>
```

FIG. 8S

```
             6590        6600        6610        6620
              *     *     *     *     *     *     *     *
             TCA CGA ATG AAT AAC GGT TTG GTT GAT GCG AGT GAT TTT GAT GAC
             AGT GCT TAC TTA TTG CCA AAC CAA CTA CGC TCA CTA AAA CTA CTG
             Ser Arg Met Asn Asn Gly Leu Val Asp Ala Ser Asp Phe Asp Asp>
             ___j___j___j___j___j___j___KANR___j___j___j___j___j___j___>

6630        6640        6650        6660        6670
         *     *     *     *     *     *     *     *     *
        GAG CGT AAT GGC TGG CCT GTT GAA CAA GTC TGG AAA GAA ATG CAT
        CTC GCA TTA CCG ACC GGA CAA CTT GTT CAG ACC TTT CTT TAC GTA
        Glu Arg Asn Gly Trp Pro Val Glu Gln Val Trp Lys Glu Met His>
        ___j___j___j___j___j___j___KANR___j___j___j___j___j___j___>

6680        6690        6700        6710
              *     *     *     *     *     *     *     *     *
             AAG CTT TTG CCA TTC TCA CCG GAT TCA GTC GTC ACT CAT GGT GAT
             TTC GAA AAC GGT AAG AGT GGC CTA AGT CAG CAG TGA GTA CCA CTA
             Lys Leu Leu Pro Phe Ser Pro Asp Ser Val Val Thr His Gly Asp>
             ___j___j___j___j___j___j___KANR___j___j___j___j___j___j___>

6720        6730        6740        6750        6760
         *     *     *     *     *     *     *     *     *
        TTC TCA CTT GAT AAC CTT ATT TTT GAC GAG GGG AAA TTA ATA GGT
        AAG AGT GAA CTA TTG GAA TAA AAA CTG CTC CCC TTT AAT TAT CCA
        Phe Ser Leu Asp Asn Leu Ile Phe Asp Glu Gly Lys Leu Ile Gly>
        ___j___j___j___j___j___j___KANR___j___j___j___j___j___j___>

6770        6780        6790        6800
              *     *     *     *     *     *     *     *
             TGT ATT GAT GTT GGA CGA GTC GGA ATC GCA GAC CGA TAC CAG GAT
             ACA TAA CTA CAA CCT GCT CAG CCT TAG CGT CTG GCT ATG GTC CTA
             Cys Ile Asp Val Gly Arg Val Gly Ile Ala Asp Arg Tyr Gln Asp>
             ___j___j___j___j___j___j___KANR___j___j___j___j___j___j___>

6810        6820        6830        6840        6850
         *     *     *     *     *     *     *     *     *
        CTT GCC ATC CTA TGG AAC TGC CTC GGT GAG TTT TCT CCT TCA TTA
        GAA CGG TAG GAT ACC TTG ACG GAG CCA CTC AAA AGA GGA AGT AAT
        Leu Ala Ile Leu Trp Asn Cys Leu Gly Glu Phe Ser Pro Ser Leu>
        ___j___j___j___j___j___j___KANR___j___j___j___j___j___j___>
```

FIG. 8T

```
              6860        6870        6880        6890
               *     *     *     *     *     *     *     *     *
              CAG   AAA   CGG   CTT   TTT   CAA   AAA   TAT   GGT   ATT   GAT   AAT   CCT   GAT   ATG
              GTC   TTT   GCC   GAA   AAA   GTT   TTT   ATA   CCA   TAA   CTA   TTA   GGA   CTA   TAC
              Gln   Lys   Trp   Leu   Phe   Gln   Lys   Tyr   Gly   Ile   Asp   Asn   Pro   Asp   Met>
              ___j___j___j___j___j___j___KANR___j___j___j___j___j___j___>

6900        6910        6920        6930        6940
          *     *     *     *     *     *     *     *     *     *
         AAT   AAA   TTG   CAG   TTT   CAT   TTG   ATG   CTC   GAT   GAG   TTT   TTC   TAA   G
         TTA   TTT   AAC   GTC   AAA   GTA   AAC   TAC   GAG   CTA   CTC   AAA   AAG   ATT   C
         Asn   Lys   Leu   Gln   Phe   His   Leu   Met   Leu   Asp   Glu   Phe   Phe   ***>
         ___j___j___j___j___j___j_KANR_j___j___j___j___j___j___>
```

```
          6950       6960       6970       6980       6990
           *     *    *     *    *     *    *     *    *     *
          AATTACTGTC TCATGAGCGG ATACATATTT GAATGTATTT AGAAAAATAA
          TTAATGACAG AGTACTCGCC TATGTATAAA CTTACATAAA TCTTTTTATT
          <_____b_____RRNBT1T2TERM_____b_____

7000       7010       7020       7030       7040
           *     *    *     *    *     *    *     *    *     *
          ACAAAAGAGT TTGTAGAAAC GCAAAAAGGC CATCCGTCAG GATGGCCTTC
          TGTTTTCTCA AACATCTTTG CGTTTTTCCG GTAGGCAGTC CTACCGGAAG
          <_____b_____RRNBT1T2TERM_____b_____

7050       7060       7070       7080       7090
           *     *    *     *    *     *    *     *    *     *
          TGCTTAATTT GATGCCTGGC AGTTTATGGC GGGCGTCCTG CCCGCCACCC
          ACGAATTAAA CTACGGACCG TCAAATACCG CCCGCAGGAC GGGCGGTGGG
          <_____b_____RRNBT1T2TERM_____b_____

7100       7110       7120       7130       7140
           *     *    *     *    *     *    *     *    *     *
          TCCGGGCCGT TGCTTCGCAA CGTTCAAATC CGCTCCCGGC GGATTTGTCC
          AGGCCCGGCA ACGAAGCGTT GCAAGTTTAG GCGAGGGCCG CCTAAACAGG
          <_____b_____RRNBT1T2TERM_____b_____

7150       7160       7170       7180       7190
           *     *    *     *    *     *    *     *    *     *
          TACTCAGGAG AGCGTTCACC GACAAACAAC AGATAAAACC AAAGCCCCAG
          ATGAGTCCTC TCGCAAGTGG CTGTTTGTTG TCTATTTTGC TTTCCGGGTC
          <_____b_____RRNBT1T2TERM_____b_____
```

FIG. 8U

```
           7200        7210        7220        7230        7240
             *    *      *    *      *    *      *    *      *    *
         TCTTTCGACT  GAGCCTTTCG  TTTTATTTGA  TGCCTGGCAG  TTCCCTACTC
         AGAAAGCTGA  CTCGGAAAGC  AAAATAAACT  ACGGACCGTC  AAGGGATGAG
         <_____b_____RRNBT1T2TERM_____b_____

7250        7260        7270        7280        7290
             *    *      *    *      *    *      *    *      *    *
         TCGCATGGGG  AGACCCCACA  CTACCATCGG  CGCTACGGCG  TTTCACTTCT
         AGCGTACCCC  TCTGGGGTGT  GATGGTAGCC  GCGATGCCGC  AAAGTGAAGA
         <_____b_____RRNBT1T2TERM_____b_____

7300        7310        7320        7330        7340
             *    *      *    *      *    *      *    *      *    *
         GAGTTCGGCA  TGGGGTCAGG  TGGGACCACC  GCGCTACTGC  CGCCAGGCAA
         CTCAAGCCGT  ACCCCAGTCC  ACCCTGGTGG  CGCGATGACG  GCGGTCCGTT
         <_____b_____RRNBT1T2TERM_____b_____

7350        7360        7370        7380        7390
             *    *      *    *      *    *      *    *      *    *
         ATTCTGTTTT  ATCAGACCGC  TTCTGCGTTC  TGATTTAATC  TGTATCAGGC
         TAAGACAAAA  TAGTCTGGCG  AAGACGCAAG  ACTAAATTAG  ACATAGTCCG
         <_____b_____RRNBT1T2TERM_____b_____

7400        7410        7420        7430          7440
             *    *      *    *      *    *      *    *       *   *
         TGAAAATCTT  CTCTCATCCG  CCAAAACAGC  CAAGCTTGGC  TCGAC CTA GTC
         ACTTTTAGAA  GAGAGTAGGC  GGTTTTGTCG  GTTCGAACCG  AGCTG GAT CAG
                                                             <*** Asp
                                                             <___g___
         <_____b___RRNBT1T2TERM____b_____

7450            7460            7470            7480
                *       *        *       *       *       *       *       *       *
            CTG GCT GAT TAA CCA GTC AGA CAA CAG CTC TTG ATA CTT GGC ATT
            GAC CGA CTA ATT GGT CAG TCT GTT GTC GAG AAC TAT GAA CCG TAA
            <Gln Ser Ile Leu Trp Asp Ser Leu Leu Glu Gln Tyr Lys Ala Asn
            <__g__g__g__g__g__g__PEPI__g__g__g__g__g__g__

7490            7500            7510            7520           7530
                *       *        *       *       *       *       *       *       *
            TTC CTG GAC AAA AGG CAT GTG GCC GCA GCC GGC AAA GAG CTC CCA
            AAG GAC CTG TTT TCC GTA CAC CGG CGT CGG CCG TTT CTC GAG GGT
            <Glu Gln Val Phe Pro Met His Gly Cys Gly Ala Phe Leu Glu Trp
            <__g__g__g__g__g__g__PEPI__g__g__g__g__g__g__
```

FIG. 8V

```
                7540          7550          7560          7570
         *    *    *    *    *    *    *    *    *
        GCG  GGC  ATT  TGG  CAA  GTG  ATC  GTA  CAT  GCT  TTT  AGC  CAC  TAG  GGG
        CGC  CCG  TAA  ACC  GTT  CAC  TAG  CAT  GTA  CGA  AAA  TCG  GTG  ATC  CCC
        <Arg  Ala  Asn  Pro  Leu  His  Asp  Tyr  Met  Ser  Lys  Ala  Val  Leu  Pro
        <___g___g___g___g___g___g___PEPI___g___g___g___g___g___g___

7580          7590          7600          7610          7620
         *    *    *    *    *    *    *    *    *
        AGT  GCA  CAA  GTC  GTC  AGT  GCC  GCT  GGT  AAT  CAA  GGC  CGG  CAA  GTC
        TCA  CGT  GTT  CAG  CAG  TCA  CGG  CGA  CCA  TTA  GTT  CCG  GCC  GTT  CAG
        <Thr  Cys  Leu  Asp  Asp  Thr  Gly  Ser  Thr  Ile  Leu  Ala  Pro  Leu  Asp
        <___g___g___g___g___g___g___PEPI___g___g___g___g___g___g___

7630          7640          7650          7660
         *    *    *    *    *    *    *    *    *
        CAG  GTC  CTT  TAA  GCG  GTC  AGT  GTA  CTC  ATA  GCC  GTG  CAG  GTT  GCC
        GTC  CAG  GAA  ATT  CGC  CAG  TCA  CAT  GAG  TAT  CGG  CAC  GTC  CAA  CGG
        <Leu  Asp  Lys  Leu  Arg  Asp  Thr  Tyr  Glu  Tyr  Gly  His  Leu  Asn  Gly
        <___g___g___g___g___g___g___PEPI___g___g___g___g___g___g___

7670          7680          7690          7700          7710
         *    *    *    *    *    *    *    *    *
        AAT  CGG  CGT  ATA  TTC  ATT  AGG  GCC  CCA  GCC  TGT  CAA  GTA  GGC  CAG
        TTA  GCC  GCA  TAT  AAG  TAA  TCC  CGG  GGT  CGG  ACA  GTT  CAT  CCG  GTC
        <Ile  Pro  Thr  Tyr  Glu  Asn  Pro  Gly  Trp  Gly  Thr  Leu  Tyr  Ala  Leu
        <___g___g___g___g___g___g___PEPI___g___g___g___g___g___g___

7720          7730          7740          7750
         *    *    *    *    *    *    *    *    *
        GTT  GCC  GCC  CTT  TTT  TTT  GCG  CAA  AAC  TGG  CTC  CGG  CAG  GTC  CGG
        CAA  CGG  CGG  GAA  AAA  AAA  CGC  GTT  TTG  ACC  GAG  GCC  GTC  CAG  GCC
        <Asn  Gly  Gly  Lys  Lys  Lys  Arg  Leu  Val  Pro  Glu  Pro  Leu  Asp  Pro
        <___g___g___g___g___g___g___PEPI___g___g___g___g___g___g___

7760          7770          7780          7790          7800
         *    *    *    *    *    *    *    *    *
        CGT  AAG  CTT  GAT  GGC  GTG  CTG  GTC  CAT  GAA  GTG  GGC  ATT  GGC  CGC
        GCA  TTC  GAA  CTA  CCG  CAC  GAC  CAG  GTA  CTT  CAC  CCG  TAA  CCG  GCG
        <Thr  Leu  Lys  Ile  Ala  His  Gln  Asp  Met  Phe  His  Ala  Asn  Ala  Ala
        <___g___g___g___g___g___g___PEPI___g___g___g___g___g___g___
```

FIG. 8W

```
                7810         7820         7830         7840
                  *     *     *     *     *     *     *     *     *
            CTG GTA GGC CGG GGA GTC GTA GTT GCC AGT TGT TTC AGC TTC CTT
            GAC CAT CCG GCC CCT CAG CAT CAA CGG TCA ACA AAG TCG AAG GAA
           <Gln Tyr Ala Pro Ser Asp Tyr Asn Gly Thr Thr Glu Ala Glu Lys
           <___g___g___g___g___g___g__PEPI___g___g___g___g___g___g__

7850         7860         7870         7880         7890
                  *     *     *     *     *     *     *     *     *
            GAT AGC GGC CTG CTC GCC CTT GGG CAG GTA CTT GAT CAA GCG GTG
            CTA TCG CCG GAC GAG CGG GAA CCC GTC CAT GAA CTA GTT CGC CAC
           <Ile Ala Ala Gln Glu Gly Lys Pro Leu Tyr Lys Ile Leu Arg His
           <___g___g___g___g___g___g__PEPI___g___g___g___g___g___g__

7900         7910         7920         7930
                  *     *     *     *     *     *     *     *     *
            CAG TTC CTG GCT CCA AAG CTT GGC GGA GGC TAA AGT GGA GGA GAG
            GTC AAG GAC CGA GGT TTC GAA CCG CCT CCG ATT TCA CCT CCT CTC
           <Leu Glu Gln Ser Trp Leu Lys Ala Ser Ala Leu Thr Ser Ser Leu
           <___g___g___g___g___g___g__PEPI___g___g___g___g___g___g__

7940         7950         7960         7970         7980
                  *     *     *     *     *     *     *     *     *
            GAT CAG GCT CTT GAC CCC TTT AGG CTG GTA GTC GCA CAG GTA GAT
            CTA GTC CGA GAA CTG GGG AAA TCC GAC CAT CAG CGT GTC CAT CTA
           <Ile Leu Ser Lys Val Gly Lys Pro Gln Tyr Asp Cys Leu Tyr Ile
           <___g___g___g___g___g___g__PEPI___g___g___g___g___g___g__

7990         8000         8010         8020
                  *     *     *     *     *     *     *     *     *
            CAA AGC CAG CAT CCC GCC CCA GCT TTG CCC CAA AAG GTG GAT CTG
            GTT TCG GTC GTA GGG CGG GGT CGA AAC GGG GTT TTC CAC CTA GAC
           <Leu Ala Leu Met Gly Gly Trp Ser Gln Gly Leu Leu His Ile Gln
           <___g___g___g___g___g___g__PEPI___g___g___g___g___g___g__

8030         8040         8050         8060         8070
                  *     *     *     *     *     *     *     *     *
            GTC AAG GCC CAG CTG CTC TCT GAC ATT TTC CAG CTC CTT GAC CCA
            CAG TTC CGG GTC GAC GAG AGA CTG TAA AAG GTC GAG GAA CTG GGT
           <Asp Leu Gly Leu Gln Glu Arg Val Asn Glu Leu Glu Lys Val Trp
           <___g___g___g___g___g___g__PEPI___g___g___g___g___g___g__
```

FIG. 8X

```
                8080          8090          8100          8110
                 *    *    *    *    *    *    *    *    *
           GGT TTG GGC CGT GTA GGC TGT TTC CGC CTG GTC GTC GGG GAT GCT
           CCA AAC CCG GCA CAT CCG ACA AAG GCG GAC CAG CAG CCC CTA CGA
           <Thr Gln Ala Thr Tyr Ala Thr Glu Ala Gln Asp Asp Pro Ile Ser
           <___g___g___g___g___g___g___PEPI____g___g___g___g___g___g___

8120          8130          8140          8150          8160
                 *    *    *    *    *    *    *    *    *
           GGA GTT GCC GCA GCC TAA TTG GTC ATA CAT GAT GAC CTG GCG GCC
           CCT CAA CGG CGT CGG ATT AAC CAG TAT GTA CTA CTG GAC CGC CGG
           <Ser Asn Gly Cys Gly Leu Gln Asp Tyr Met Ile Val Gln Arg Gly
           <___g___g___g___g___g___g___PEPI____g___g___g___g___g___g___

8170          8180          8190          8200
                 *    *    *    *    *    *    *    *    *
           GCT TTT TTC AGC GAC TTG GTC GAG GAC TTC AAA ATA GTT GTG ACT
           CGA AAA AAG TCG CTG AAC CAG CTC CTG AAG TTT TAT CAA CAC TGA
           <Ser Lys Glu Ala Val Gln Asp Leu Val Glu Phe Tyr Asn His Ser
           <___g___g___g___g___g___g___PEPI____g___g___g___g___g___g___

8210          8220          8230          8240          8250
                 *    *    *    *    *    *    *    *    *
           GCT GCC GGG CCC GCC GTG GAG AAG GAG GAG CGG GGC GCG GTC AGT
           CGA CGG CCC GGG CGG CAC CTC TTC CTC CTC GCC CCG CGC CAG TCA
           <Ser Gly Pro Gly Gly His Leu Leu Leu Leu Pro Ala Arg Asp Thr
           <___g___g___g___g___g___g___PEPI____g___g___g___g___g___g___

8260          8270          8280          8290
                 *    *    *    *    *    *    *    *    *
           AGC CTC GCC CAC GAT CCG GCA GTA GGT TTG CCA ATT TCC AAA TGG
           TCG GAG CGG GTG CTA GGC CGT CAT CCA AAC GGT TAA AGG TTT ACC
           <Ala Glu Gly Val Ile Trp Cys Tyr Thr Gln Trp Asn Gly Phe Pro
           <___g___g___g___g___g___g___PEPI____g___g___g___g___g___g___

8300          8310          8320          8330          8340
                 *    *    *    *    *    *    *    *    *
           AAG ATA TTT TTC TGT GAT TTG CAT CTTGAATTAA TTCTGTTTCC
           TTC TAT AAA AAG ACA CTA AAC GTA GAACTTAATT AAGACAAAGG
           <Leu Tyr Lys Glu Thr Ile Gln Met
           <___g___g___g_PEPI___g___g___g___
                                              <__c_____
```

FIG. 8Y

```
         8350        8360        8370        8380        8390
          *   *       *   *       *   *       *   *       *   *
        TGTGTGAAAT TGTTATCCGC TCACAATTCC ACACATTATA CGAGCCGATG
        ACACACTTTA ACAATAGGCG AGTGTTAAGG TGTGTAATAT GCTCGGCTAC
        <_____c_____c__PTAC____c_____c_____

8400        8410        8420        8430
          *   *       *   *       *   *       *   *
        ATTAATTGTC AACAGCTCAT TTCAGAATAT TTGCCAGTAA
        TAATTAACAG TTGTCGAGTA AAGTCTTATA AACGGTCATT
        <_____c_____PTAC_____c_____
```

FIG. 8Z

β-CASEIN EXPRESSING CONSTRUCTS

The subject application is a Continuation-In-Part of pending U.S. patent application Ser. No. 09/064,440 filed on Apr. 22, 1998 now abandoned, which is a divisional of U.S. patent application Ser. No. 08/757,177, filed on Nov. 27, 1996, now U.S. Pat. No. 6,071,718, which are herein incorporated in their entirety by reference.

BACKGROUND OF THE INVENTION

1. Technical Field

The subject invention relates to β-casein expressing constructs which have significant stability when introduced into host cells. These constructs, for purposes of the present invention, have been designated as pRAB-84-69 and pRSB-14.

2. Background Information

Stability of a plasmid in an induced cell culture is influenced by the external physical culture conditions as well as the internal environment of the cell. There are several external factors that may have an effect on plasmid stability. For example, it has been shown that a lack of carbon, nitrogen, phosphate and minerals can negatively affect plasmid stability (Godwin et al., *J. Gen. Microbiol.* 111:201–10 (1979)). Use of a richer media may therefore alleviate plasmid loss in some cases.

The physiology of the host strain is another factor which has an important effect on plasmid stability, as the same plasmid can show different rates of loss depending on the host (Caulcott et al., *J. Gen. Microbiology* 133:1881–89 (1987)). Some plasmids are inherently unstable due to improper replication and segregation. Unstable segregation in the earlier stages of the culture gives a growth disadvantage to the cells harboring the plasmid, consequently leading to an increased proportion of cells without the plasmid. Maintenance of the plasmid in the culture also requires optimum levels of selective pressure on the culture to ensure that only cells harboring the plasmid with the selectable marker survive.

In addition to the above mentioned factors, the absence or presence of specific sequences may also affect plasmid stability. Chiang and Bremmer studied the stability of plasmid pBR322 and its tet, bla and rom derivatives (Chiang et al., *Plasmid* 20:207–220 (1988)). They reported that transcription of tet sequences present on pBR322 affects cell viability and may reduce plasmid stability. In other instances, the presence of certain sequences such as the par stability locus has been shown to stabilize plasmids with segregational instability (Austin et al., *Plasmid* 20:1–9 (1988)). Furthermore, the size of the inserted DNA and the "act of introducing" foreign DNA are also known to effect plasmid stability. Stability is negatively affected by inserts over 8 kb in size and has been attributed to replication fidelity, segregation or low copy number (Warnes et al., *Plasmid* 16:116–23 (1986)).

Such instability prevents large-scale or efficient production of the protein encoded by the nucleotide sequences present in the plasmid. Thus, such instability may have quite a large impact on the production level of the protein as well as on the development of diagnostic and therapeutic products. Additionally, genetic instability of the plasmid is important with respect to the receipt of regulatory approval for a commercial process.

The present constructs, derived from pRJB36, are quite stable and therefore permit the expression of large quantities of the desired end product. For example, the constructs may be used in the expression of a protein such as recombinant human β-casein. Thus, the present constructs overcome many of the disadvantages associated with known constructs such as pRJB36.

All U.S. patents and publications referred to herein are hereby incorporated in their entirety by reference.

SUMMARY OF THE INVENTION

The present invention includes an isolated DNA sequence comprising a nucleotide sequence encoding a protein, wherein the nucleotide sequence is operably linked to a promoter, a nucleotide sequence encoding a first subunit of a kinase, a nucleotide sequence encoding a second subunit of the kinase, a nucleotide sequence encoding a peptidase and a nucleotide sequence encoding a bacterial resistance marker. The protein may be, for example, a human milk protein such as recombinant human β-casein, a protein from an edible plant, an antibody and an antigen. The promoter may be selected from the group consisting of Ptac, Pgal, T7, $\lambda P_L$, $\lambda P_R$, bla and spa. The kinase may be, for example, casein kinaseIIβα, and the peptidase may be, for example, aminopeptidase and iminopeptidase. The bacterial resistance marker may be selected from the group consisting of ampicillin resistance, kanamycin resistance, chloramphenicol resistance, and tetracycline resistance. The isolated DNA sequence may further comprise a transcriptional terminator such as rrnBT1T2.

Additionally, the present invention also encompasses a vector containing the isolated DNA sequence described above as well as a host cell containing this vector. The host cell may be prokaryotic, for example, a bacterial cell, such as *Escherichia* spp. (e.g., *E. coli*) or eukaryotic.

Furthermore, the present invention also includes a method of producing a protein comprising introducing a vector into a host cell under time and conditions sufficient for expression of the protein. The vector may comprise an isolated DNA sequence comprising i) a nucleotide sequence encoding a protein, wherein the nucleotide sequence is operably linked to a promoter, ii) a nucleotide sequence encoding a first subunit of a kinase, iii) a nucleotide sequence encoding a second subunit of a kinase, iv) a nucleotide sequence encoding a peptidase and v) a nucleotide sequence encoding a bacterial resistance marker. The isolated DNA sequence may also comprise a transcription terminator such as rrnBT1T2. The protein, kinase, peptidase, promoter and bacterial resistance marker may be as described above.

Additionally, the present invention includes a pharmaceutical or nutritional composition comprising a protein produced according to the method described above.

The present invention also includes a vaccine which comprises a protein produced in accordance with the method described above.

Moreover, the present invention also encompasses a method of improving the genetic stability of a plasmid-containing cell during fermentation. This method comprises the step of transforming a cell with the above described vector, prior to fermentation, growing the cell in a culture utilized for inoculating a fermentor, growing the cell in the fermentor, inducing at least one of the nucleotide sequences present in the vector, and completing fermentation under for a time and under conditions suitable for optimal expression of the induced nucleotide sequence or sequences.

BRIEF DESCRIPTION OF THE DRAWINGS

FIG. 7 represents the nucleotide (SEQ ID NO:1) and amino acid (SEQ ID NOS:2–5) sequences of pRAB-84-69. (see also SEQ ID NO:8 and SEQ ID NO:9.)

FIG. 8 represents the nucleotide (SEQ ID NO:6) and amino acid (SEQ ID NO:7) (sequences of pRAB-14. (see also SEQ ID NO:10, SEQ ID NO:11, SEQ ID NO:12, SEQ ID NO:13 and SEQ ID NO:14.)

All U.S. patents and publications referred to herein are hereby incorporated in their entirety by reference.

DETAILED DESCRIPTION OF THE INVENTION

The present invention relates to two unique constructs, pRAB-84-69 and pRSB-14, and to the uses of these constructs. For example, the constructs may be used in the expression of recombinant proteins such as, for example, recombinant human β-casein.

Figure 1A:
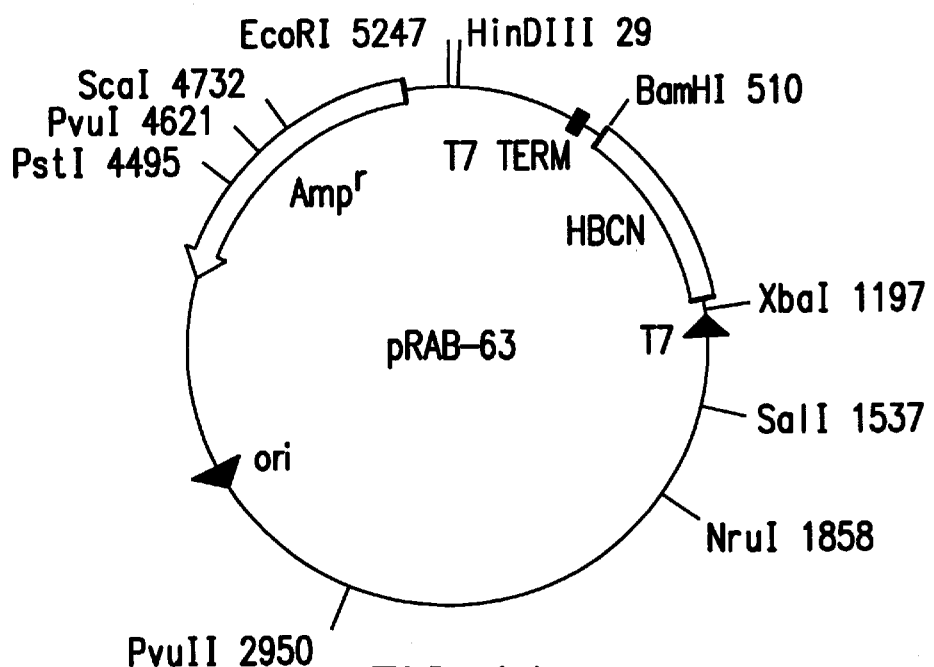
FIG. 1 represents a genetic map of A) plasmid pRAB-63 and B) plasmid pRAB-84-69.
Figure 1B:
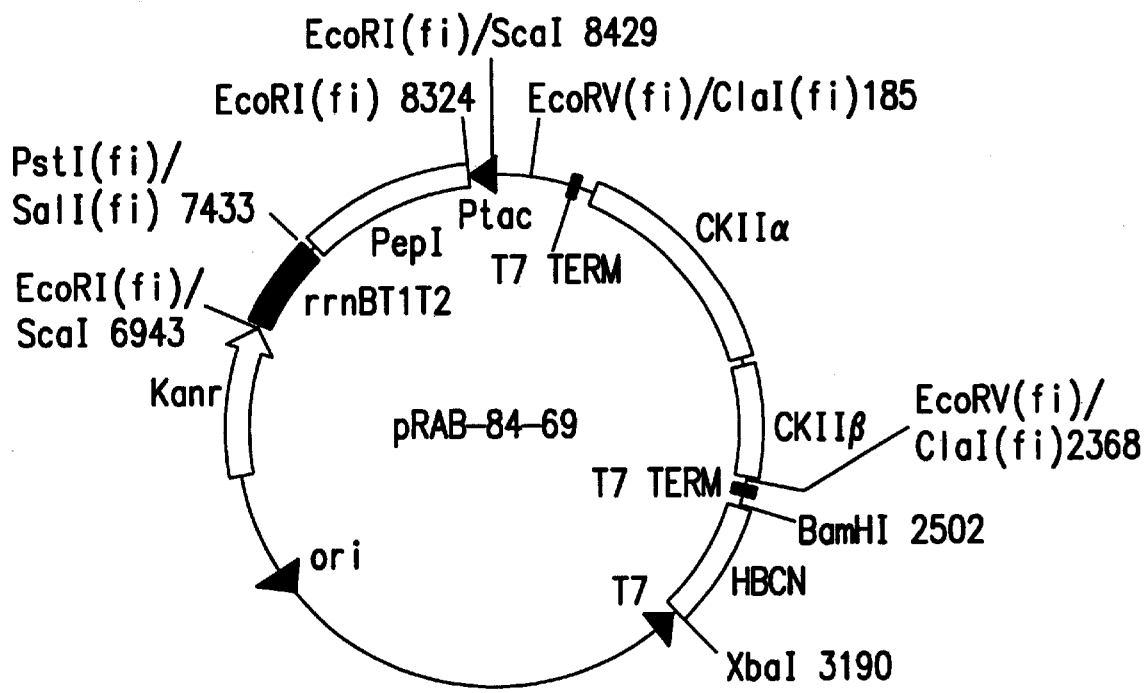
Figure 2A:
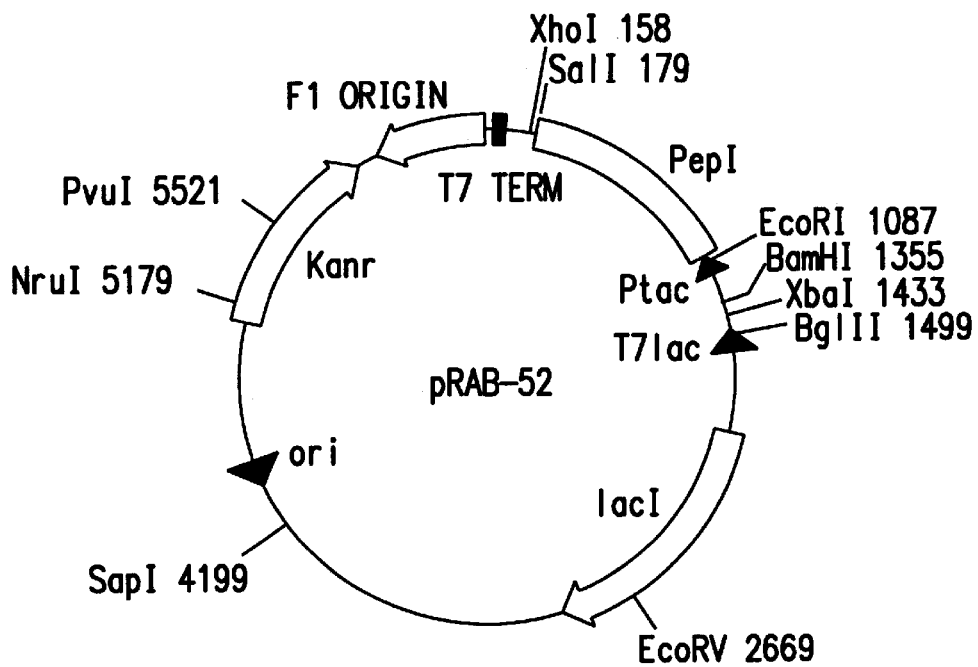
FIG. 2 represents a genetic map of A) plasmid pRAB-52 and B) plasmid pRSB-14.
Figure 2B:
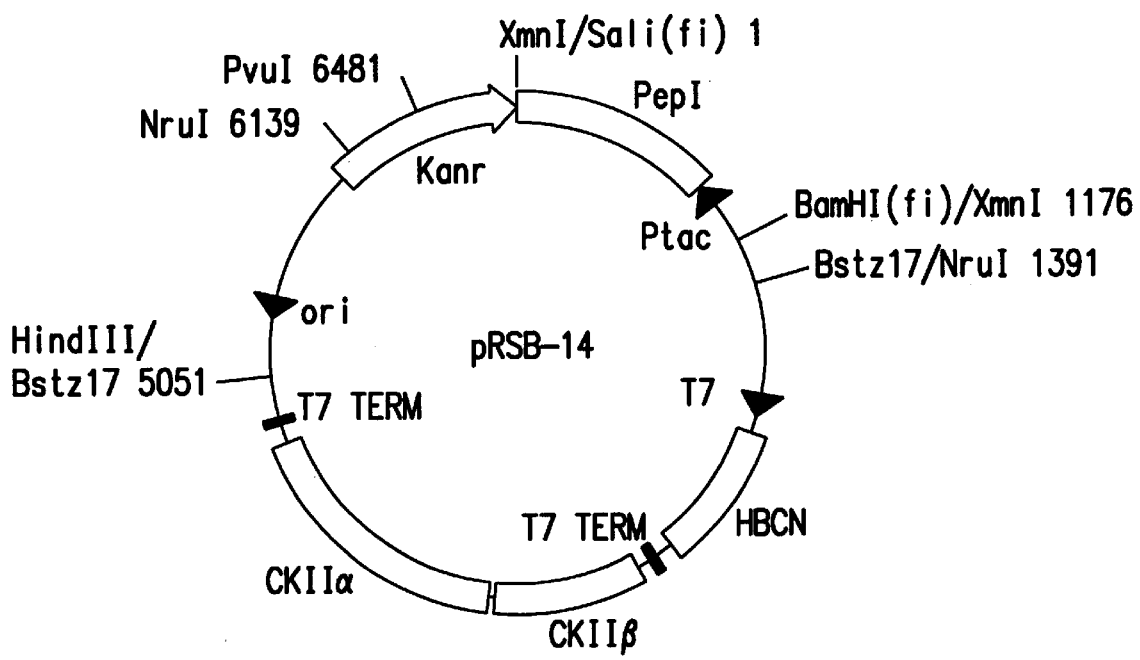
Figure 3:
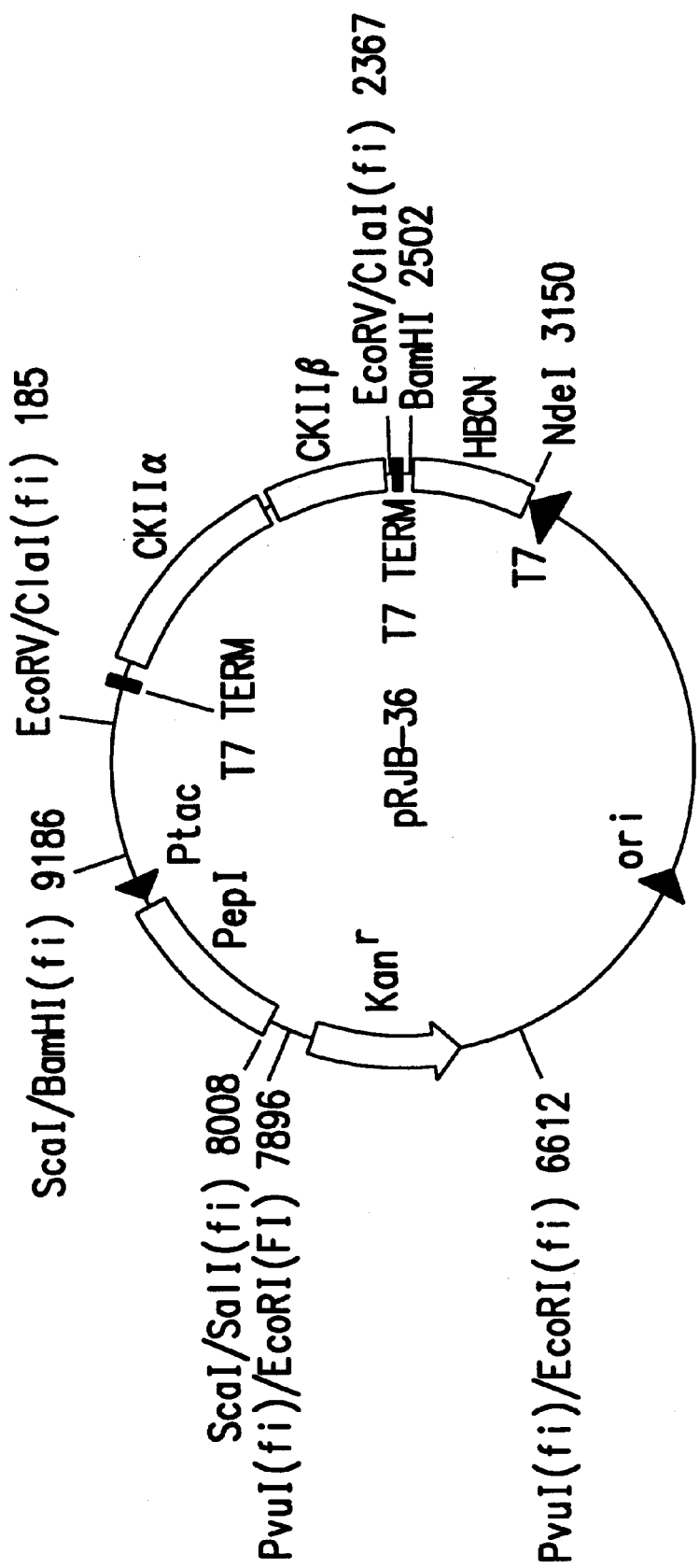
FIG. 3 represents a genetic map of plasmid pRJB-36.

The genetic map of pRAB-84-69 is shown in FIG. 1, and the map of pRSB-14 is shown in FIG. 2. Construct pRAB-84-69 comprises a first gene encoding the protein of interest, a second gene encoding the beta subunit of casein kinaseIIβα, a third gene encoding the alpha subunit of casein kinaseIIβα, a fourth gene encoding a peptidase, and a fifth gene encoding antibiotic resistance. One promoter, operably linked to the first gene, controls the expression of the first, second and third genes. An additional promoter, operably linked to the fourth gene, and another promoter, operably linked to the fifth gene, control or regulate the expression of the fourth and fifth genes, respectively.

More specifically, the first gene may encode, for example, any protein including, but not limited to, a milk protein, a protein from an edible plant, an antibody, an antigen, a hormone or an enzyme. Preferably, the first gene encodes recombinant human β-casein. The fourth gene may encode, for example, either iminopeptidase or aminopeptidase, depending upon the protein one wishes to produce. Preferably, the fourth gene encodes iminopeptidase if one wishes to produce recombinant human β-casein. The fifth gene encodes antibiotic resistance, for example, kanamycin resistance, chloramphenicol resistance, ampicillin resistance or tetracycline resistance. The fifth gene preferably encodes kanamycin resistance in a situation where recombinant human β-casein is being produced. It should also be noted that the second and third genes may be replaced by a single gene encoding an enzyme. For example, a gene encoding tyrosine kinase may replace the genes encoding, for example, casein kinaseIIβα.

The promoter utilized for expression of the genes may be any promoter which is functional in the host cell and is able to elicit expression of the product encoded by the gene. Suitable promoters include, for example, T7, Ptac, Pgal, λPL, λPR, bla and spa. Preferably, T7 is utilized.

Construct pRSB-14 comprises a first gene encoding the protein of interest, a second gene encoding the beta subunit of casein kinaseIIβα, a third gene encoding the alpha subunit of casein kinaseIIβα, a fourth gene encoding a peptidase, and a fifth gene encoding antibiotic resistance. One promoter, operably linked to the first gene, controls the expression of the first, second and third genes. An additional promoter, operably linked to the fourth gene, and another promoter, operably linked to the fifth gene, control or regulate the expression of the fourth and fifth genes, respectively.

More specifically, the first gene may encode, for example, any protein, including but not limited to, a milk protein, a protein from an edible plant, an antibody, an antigen, a hormone or an enzyme. Preferably, the first gene encodes recombinant human β-casein. The fourth gene may encode, for example, either iminopeptidase or aminopeptidase, depending upon the protein one wishes to produce. Preferably, the fourth gene encodes iminopeptidase if one wishes to produce recombinant human β-casein. The fifth gene encodes antibiotic resistance, for example, kanamycin resistance, chloramphenicol resistance, ampicillin resistance or tetracycline resistance. The fifth gene preferably encodes kanamycin resistance in a situation where recombinant human β-casein is being produced. It should also be noted that the second and third genes may be replaced by a single gene encoding an enzyme. For example, a gene encoding tyrosine kinase may replace the genes encoding, for example, casein kinaseIIβα.

The promoter utilized for expression of the genes may be any promoter which is functional in the host cell and is able to elicit expression of the product encoded by the gene. Suitable promoters include, for example, T7, Ptac, Pgal, λPL, λPR, bla and spa. Preferably, T7 is utilized.

The nucleotide sequence of pRAB-84-69 (SEQ ID NO:1) and the amino acid sequence of pRAB-84-69 (SEQ ID NOS:2–5) are shown in FIG. 7. The nucleotide sequence of pRSB-14 (SEQ ID NO:6) and the amino acid sequence of pRSB-14 (SEQ ID NO:7) are shown in FIG. 8.

The plasmids pRAB84-69 and pRSB-14 were deposited with the American Type Culture Collection (ATCC), 10801 University Boulevard, Manassas, Va. 20110-2209 on Apr. 1, 1998 under the terms of the Budapest Treaty. The plasmid pRAB84-69 was accorded ATCC deposit number 209723, and the plasmid pRSB-14 was accorded ATCC deposit number 209724.

It should be noted that the vectors or constructs of the present invention are substantially pure polynucleotides. An "isolated" or "substantially pure" polynucleotide is a polynucleotide (e.g., an RNA, DNA, or a mixed polymer) which is substantially separated from other polynucleotide sequences which naturally accompany a native sequence. The term embraces a polynucleotide sequence which has been removed from its naturally occurring environment, and includes recombinant or cloned DNA isolates and chemically synthesized analogues or analogues biologically synthesized by heterologous systems.

A polynucleotide is said to "encode" a polypeptide if, in its native state or when manipulated by methods known in the art, the polynucleotide can be transcribed and/or translated to produce the polypeptide of a fragment thereof.

Polynucleotide sequences are "operably linked" when they are placed into a functional relationship with another polynucleotide sequence. For instance, a promoter is operably linked to a coding sequence if the promoter affects transcription or expression of the coding sequence. Generally, operably linked means that the linked sequences are contiguous and, where necessary to join two protein coding regions, both contiguous and in the same reading frame. However, it is well known that certain genetic elements, such as enhancers, may be operably linked even at a distance, i.e., even if not contiguous.

The term "recombinant" polynucleotide refers to a polynucleotide which is made by the combination of two otherwise separated segments of sequence accomplished by the artificial manipulation of isolated segments of polynucleotides by genetic engineering techniques or by chemical synthesis. In so doing, one may join together polynucleotide segments of desired functions to generate a desired combination of functions.

Briefly, the constructs or plasmids of the present invention are created by digesting a vector of choice with restriction enzymes of choice, modifying the digested sites with enzymes such as, for example, polymerase, kinases or exonucleases, and ligating the desired prepared genes or DNA sequences to the modified sites. A detailed description of the creation of the constructs is presented in the examples set forth below.

The constructs may be introduced into a prokaryotic or eukaryotic host cells. Examples of suitable prokaryotic host cells include, for example, bacterial cells. Preferably, Escherichia spp. cells are utilized as host cells and, more preferably, E. coli cells are utilized. Examples of suitable eukaryotic host cells include, for example, yeast cells, preferably Saccharomyces cerevisiae cells, mammalian cells and plant cells.

The construct may be introduced into the host cell of choice by methods known to those of ordinary skill in the art including, for example, transfection, and transformation and electroporation (see *Molecular Cloning: A Laboratory Manual*, 2nd ed., Vol. 1–3, ed. Sambrook et al., Cold Spring Harbor Laboratory Press (1989)). The host cell is then cultured under suitable condition permitting production of the protein, which is then recovered.

The present invention also includes products, containing the protein of interest, wherein the protein is produced by using the above-described constructs. This is achieved by introducing either pRAB-84-69 or pRSB-14 into the host cells, and then treating the host cells to remove the protein. The protein can then be subjected to further purification if required and introduced into, for example, a therapeutic or nutritional composition. Thus, the present constructs allow for the production of high yields of the protein of interest, a protein which may then be used for many commercial and non-commercial purposes.

In particular, pharmaceutical compositions may be prepared which contain effective amounts of the protein and a pharmaceutically acceptable carrier, adjuvant or vehicle such as, for example, phosphate buffered saline, water, wetting agents, and emulsions such as oil/water or water/oil. The pharmaceutical may then be administered to a mammal such as a human or an animal. Thus, the composition has human as well as veterinary applications.

The dosage of the composition to be administered may be readily determined by one of ordinary skill in art and depends upon various factors such as the weight, age, and immune status of the patient.

With respect to nutritional compositions, such compositions may contain one or more nucleotides, oligosaccharides and proteins, in combination, in addition to one or more recombinant proteins produced in accordance with the present invention. Such a nutritional composition may be, for example, a human or animal dietary supplement or an infant formula. The composition may be either in liquid or solid form.

Additionally, the expressed protein may be used in the formulation of a vaccine. The protein may be utilized as an antigen which, in turn, elicits a protective antibody response (i.e., active immunization). The vaccine may contain not only the protein, but other entities having antigenic properties, as well as, for example, a carrier or adjuvant known to one of ordinary skill in the art. Alternatively, an antibody produced using the present constructs may also be utilized in a vaccine for purposes of passive immunization.

Furthermore, the present invention includes a method of producing the protein of interest using a plasmid or construct of the invention. This method comprises preparing the plasmid of interest, inserting the plasmid into an appropriate host cell, culturing the host cell for a suitable time and under suitable conditions such that the protein of interest is expressed, and then purifying the protein.

Additionally, the present invention includes a method of improving the genetic stability of a plasmid-containing cell during fermentation. The method comprises the steps of transforming a host cell with one or more plasmids, as described above, growing the host cell in culture media to be used for inoculating a fermentor, inducing at least one gene (e.g., a gene which encodes human β-casein, a gene which encodes the alpha-subunit of casein kinaseII, a gene which encodes the beta-subunit of casein kinaseII, and/or a gene which encodes iminopeptidase) present in the plasmid (by, for example, addition of an oligosaccharide such as lactose) after appropriate incubation of the transformed host cell in the fermentor, and continuing fermentation of the host cell in the induced state in order to obtain optimal gene expression (of the induced gene or genes present in the plasmid).

The present invention may be illustrated by the use of the following non-limiting examples:

EXAMPLE I

Construction of Plasmid pRAB84-69 pS637 is identical to pS26 (Hansson, et al., *Protein Expression and Purification* 4:373–381 (1993)), except that it contains three extra bases, CAG, which encode the amino acid glutamine at site 20. Both forms of beta-casein exist in nature. The human beta-casein gene was PCR amplified from construct pS637 using the primer RO190 (5' GGA GAT ATA CT ATG (CCH CGT GAA ACC ATC GAA TCC CTG AGC 3')(SEQ ID NO:15)) and RO74 (5' GCT AGT TAT TGC TCA GCG G 3')(SEQ ID NO:16). The PCR generated fragment was cloned into NdeI/BamHI (Boehringer Mannheim, Indianapolis, Ind.) digested pET-3a+ (Novagen, Inc., Madison, Wis.) to create the construct pRAB-63. The vector pET-9a (Novagen, Inc., Madison, Wis.) and the construct pRAB-63 were cut sequentially with restriction enzymes BamHI and XbaI, then desphosphorylated using the shrimp alkaline phosphatase (Boehringer Mannheim, Indianapolis, Ind.). The BamHI/XbaI cut and dephosphorylated pET-9a vector and the gel purified human beta-casein gene fragment from pRAB-63 were ligated to create the construct pRAB-72. The Ptac promoter with the multicloning site and the rrnBT1T2 terminator (Brosius et al., *Proc. Natl. Acad. Sci. USA* 81:6929 (1984), Amann et al., Gene 25:167 (1983) and Frost et al., *Biochemistry* 23:4470 (1984)) was PCR amplified from the pKK223-3 plasmid (Pharmacia, Piscataway, N.J.) using primers RO204 (5' GCA TTT ATC AGG AGT ACT GTC TCA TGA GCG G 3')(SEQ ID NO:17) and RO221 (5' CGA CAT CAT AAC AGT ACT GGC 3')(SEQ ID NO:18). The PCR amplified cassette was cut with ScaI and gel purified. pRAB-72 was cut with EcoRI, filled-in using $T_4$ DNA polymerase (Boehringer Mannheim, Indianapolis, Ind.), and dephosphorylated. The construct pRAB-81 was created by ligating the pRAB-72 (EcoRI digested) vector with the Ptac/term cassette. pET-24a+ (Novagen, Inc., Madison, Wis.) was digested with EcoRI and SalI. The iminopeptidase gene (pepI) was PCR amplified from Lactobacillus delbrueckii subsp. lactis (ATCC 4797) (ATCC, Rockville, Md.) using primers RO117 (5' TCA GAG GAA TTC AAG ATG CAA ATC ACA GAA AAA TA 3' (SEQ ID NO:19)) & RO118 (5' GTG TCC GTC GAC CTA GTC CTG GCT GAT TAA CCA GT 3' (SEQ ID NO:20)). pRJB-31 was created by ligating the PCR amplified pepI gene into the EcoRI/SalI digested pET-24a+(Novagen, Inc., Madison, Wis.). pRAB-81 was cut with EcoRI and PstI, filled-in and dephosphorylated. pRJB-31 was cut with EcoRI and SalI, and the fragment containing the pepI gene was gel purified and filled-in. The construct pRAB-82 was created by ligating the vector pRAB-81 (EcoRI/PstI digested) with the pepI gene fragment from pRJB-31. pRAB-82 was cut with EcoRV, filled-in, and dephosphorylated. pET-11d-CKIIβα (Symbicom, Umea, Sweden) was cut with ClaI, and the casein kinaseIIβα (CKIIβα) was gel purified. The final construct pRAB-84 was created by ligating the vector pRAB-82 (EcoRV digested) with the CKIIβα from pET-11d-CKIIβα.

EXAMPLE II

Construction of Plasmid pRSB-14

The BamHI digested and filled-in Ptac promoter from pKK223-3 was cloned in at the EcoRI digested and filled-in pRJB-31 to create the construct pRAB-52. The construct PRSB-13a was created by ligating XmnI digested pET-24a+ (Novagen, Inc., Madison, Wis.) with BamHI/SalI digested and filled-in pepI gene fragment from pRAB-52. PRJB-36 was digested with HindIII/NruI, and the fragment containing the human β-casein gene and the CKIIβα genes was filed in. pRSB-13a was digested with BstZ17 and filled-in. The final construct pRSB-14 was created by ligating the vector pRSB-13a (BstZ17 digested) with the prepared pRJB-36 fragment.

EXAMPLE III

Construction of Plasmid pRJB-36 pS637 was digested with EcoRV and religated to removed the sequence between the two EcoRV sites. The new plasmid was named pRJB-6. The linker RO77/78 (5'TATGCCGCGTGAACCATCGAATCCCTGAGCT 3') (SEQ ID NO:21) (3'ACGGCGCACTTTGGTAGCTTAGGGAC 5')(SEQ ID NO:22) was cloned in at the NdeI/SacI sites of pS637 to create pRAB-28. This added the bases comprising a codon for a proline residue next to the ATG, the codon for methionine at the start of a protein. ClaI digested CKIIβα gene from pET11-d-CKIIβα was cloned into the EcoRV site of pRJB-6 to create pRJB-9 (Thurmond et al., *Protein Expression and Purification* 10:202–208). BglII digested human beta-casein fragment from pRAB-28 was cloned in at the BglII site of pRJB-9 to create pRAB-30. EcoRI cut and filled-in Kanamycin resistance Genblock (Pharmacia, Piscataway, N.J.) was cloned in at the PvuI cut filled-in pRAB-30 to create pRJB-18. The BamHI/SalI digested and filled-in Ptac/PepI fragment of pRAB-52 containing the Ptac promoter and pepI gene was cloned in at the ScaI digested pRJB-18 to create pRJB-36.

EXAMPLE IV

Comparative Stability Assay of pRJB36, pRSB14 and pRAB84-69

Stability assays on the above constructs were carried out as follows:
Shake flask: 5 ml of Luria Broth (LB) broth containing 30 μg/ml kanamycin were inoculated for overnight growth in a 37° C. shaker incubator with a colony picked from a fresh plate of *E. coli* HMS174(DE3) containing the desired construct. 50 ml of LB containing 30 μg/ml kanamycin was inoculated with 1 ml of this overnight culture. The large culture was allowed to grow until the OD600 reached approximately 0.6–1.0, at which point the culture was induced with 2% lactose.
Preparation of 5 Liter Fermentation Culture: The reagents were prepared as follows:

I) Make-up for 10× Trace Minerals

| Ingredient | Formula | Amount to Weigh/Liter |
|---|---|---|
| Sodium molybdate | $Na_2MoO_4\text{-}2H_2O$ | 49.6 mg |
| Cobalt chloride | $CaCl_2\text{-}7H_2O$ | 49.6 mg |
| Ferrous sulfate | $FeSO_4\text{-}7H_2O$ | 1359 mg |
| Manganese sulfate | $MnSO_4\text{-}H_2O$ | 225 mg |
| Zinc sulfate | $ZnSO_4\text{-}7H_2O$ | 130 mg |
| Boric acid | $H_3BO_3$ | 60.6 mg |
| Cupric sulfate | $CuSO_4\text{-}5H_2O$ | 44.0 mg |
| Calcium chloride | $CaCl_2\text{-}2H_2O$ | 2000 mg |

II) Make-up for Fermentor Medium

| Ingredient | g/l (4.2 liter) basis | Weight out (4.2 Liter final volume) |
|---|---|---|
| NZ Amine K | 1.0 g | 4.2 g |
| Hy Yeast 412 | 1.0 g | 4.2 g |
| Mono potassium phosphate ($KH_2PO_4$) | 3.4 g | 14.3 g |
| Magnesium sulfate ($MgSO_4\text{-}7H_2O$) | 1,1 g | 4.6 g |
| Citric acid | 1.5 g | 6.3 g |
| Sterile 50% (w/v) dextrose solution | | 110 ml |
| 10X trace minerals | | 105 ml |
| Sterile 30 mg/ml kanamycin solution | | 2.8 ml |
| Mazu DF204 (antifoam) | 0.2 g | 0.85 ml |

The fermentor was batched at 2.8 liters prior to sterilization. The dextrose and kanamycin solutions were added aseptically just prior to inoculation of the fermentor.

III) Make-up for Inoculum Medium

| Ingredient | g/l |
|---|---|
| NZ Amine K | 2.0 |
| Hy Yeast 412 | 2.0 |
| Mono potassium phosphate ($KH_2PO_4$) | 6.7 |
| Magnesium sulfate ($MgSO_4\text{-}7H_2O$) | 2.2 |
| Citric acid | 3.0 |
| Sterile 50% (w/v) dextrose solution | 20 ml |
| 10X trace minerals | 50 ml |
| Sterile 30 mg/ml kanamycin solution | 1 ml |

The pH of the medium was adjusted to 7.4 with ammonium hydroxide prior to sterilization. Two hundred ml of medium were distributed into a 1 liter triple baffled shake flask, which was closed with a silicon sponge closure.

IV) Lactose Feed

| Ingredient | g/l |
|---|---|
| Lactose (monohydrate) | 227 |
| Magnesium sulfate ($MgSO_4\text{-}7H_2O$) | 6.8 |
| Citric acid | 3.4 |
| 10X trace minerals | 57 ml |
| Sterile 30 mg/ml kanamycin solution | 1 ml |

Kanamycin was aseptically added to the feed once the medium had cooled.

V) Inoculum Preparation

A 1.5 ml frozen glycerol vial of *E. coli* was aseptically dispensed into 200 ml of inoculum medium. The inoculum flask was then incubated 22–24 hours at 30° C. with 300 rpm agitation. The contents were used to inoculate 2.9 liters of fermentor medium.

VI) Fermentation Protocol

The fermentor was batched with medium and sterilized 40 minutes at 121° C. Once cool, 100 ml of 50% sterile dextrose and 2.9 ml of kanamycin were added aseptically. The pH was 7.0, temperature was 30° C., and the initial aeration and agitation settings were 600 rpm and 3.5 liters/minute aeration, respectively.

The fermentor was inoculated with 200 ml of seed, and the fermentation was allowed to proceed with routine sampling and monitoring of the optical density and dextrose concentration.

Cell density was measured at 600 nm using the Turner spectrophotometer (Barnstead, Dubuque, Iowa).

Lactose feed was started when the OD was 10–12 and the dextrose concentration was 4–6 g/l. The lactose was fed at a constant rate of 105 ml/h. At this time, the aeration rate was increased to 5 lpm. The agitation was programmed to maintain a dissolved oxygen tension of 25%.

Stability Assay: Aliquots of cultures of HMS174(DE3), harboring a given plasmid, were removed at different time points. Several dilutions of the aliquots were made in LB media and spread on LB agar plates. The plates were incubated at 37° C., overnight. Single colonies were picked up from the LB plates and replica-plated on LB agar plates containing 30 μg/ml kanamycin (LB+Kan) plates. Number of colonies that grew on LB agar plates and on LB+Kan plates were used to determine the stability of that plasmid. % Stability=Number of colonies that grew on LB+Kan plates/Total Number of colonies streaked from LB plates.

Figure 4:
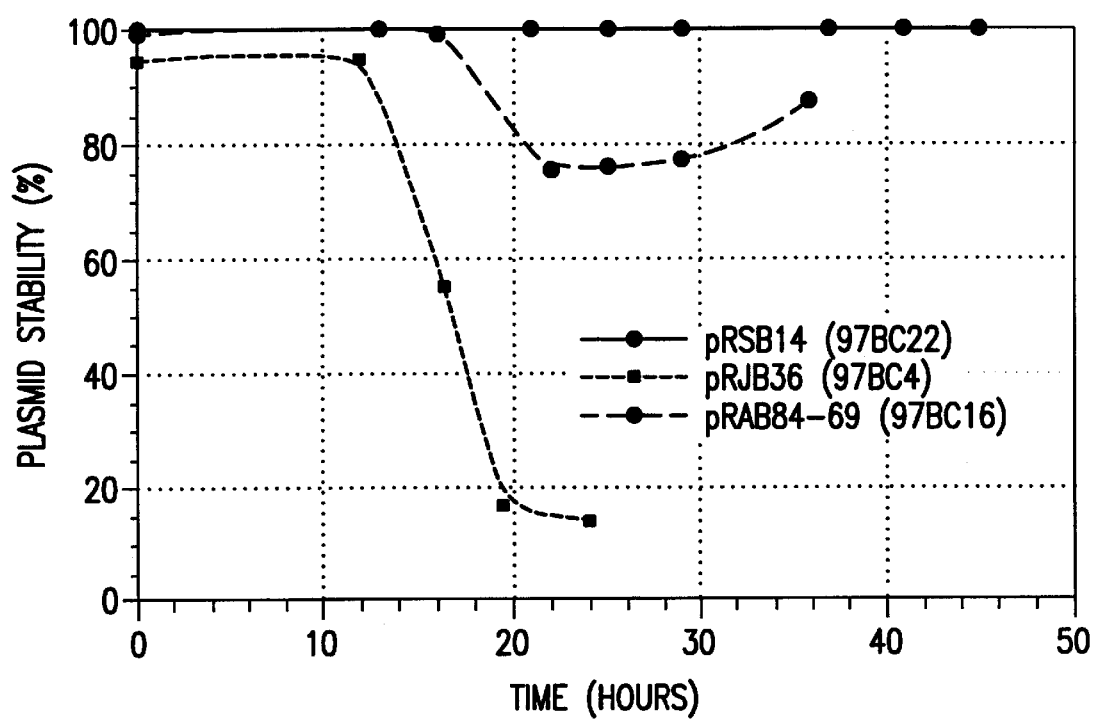
FIG. 4 illustrates the plasmid stability of pRSB-14, pRJB-36 and pRAB-84-69 over time.

It was determined that pRSB14 and pRAB84-69 were more stable than pRJB36 after 12–20 hours of induction. In particular, the pRSB14 construct was 100% stable while pRAB84-69 was 80% stable, as compared to pRJB36, which ranged from 5–20% under the same conditions. (See FIG. 4.)

EXAMPLE V

Comparison of β-casein Levels Using pRJB-36, pRSB14 and pRAB84-69

The constructs were introduced into *E. coli* cells as follows:

Twenty microliter aliquots of thawed competent HMS174 (DE3) cells from Novagene (Madison, Wis.) were placed, in tubes, on ice. One μl of construct DNA was added directly to the cells in each of the tubes. Each mixture was gently stirred and placed on ice for 30 minutes. The tubes were heated for exactly 40 seconds in a 42° C. water bath. Eighty microliters of SOC medium (Sambrook et al., supra) was added to each tube. The tubes were then shaken at 200–250 rpm at 37° C. for 1 hour. Twenty microliters of each transformation was spread onto LB+Kan agar plates. The plates were then allowed to sit for several minutes, on the bench, to allow excess liquid to be absorbed. They were then inverted and incubated overnight at 37° C. The colonies were then grown in liquid cultures and induced for β-casein expression as described previously (Thurmond et al., *Protein Expression and Purification* 10:202–208).

The level of beta-casein from the constructs was determined by comparing the intensities of the protein bands to those of reference protein bands containing known quantities of human beta-casein on a Western blot.

Figure 5A:
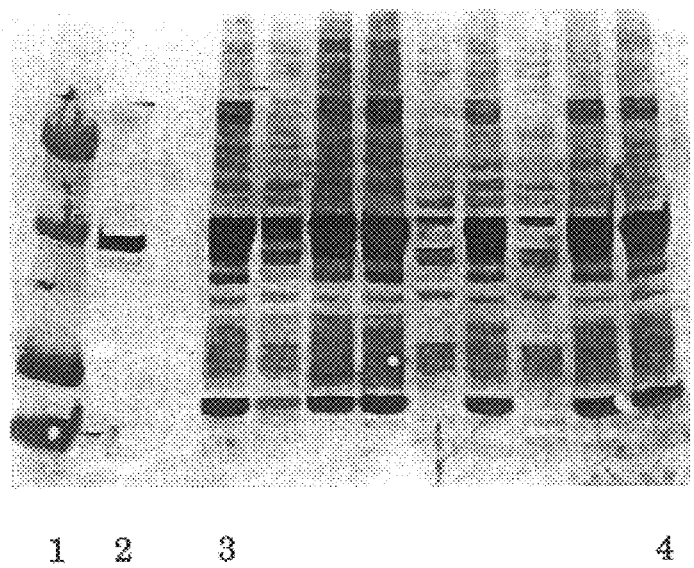
FIG. 5 illustrates the level of β-casein produced by pRAB-84-69 compared to that produced by pRJB36 (Panel A) and the level of β-casein produced by pRSB-14 compared to that produced by pRJB36 (Panel B).
Figure 5B:
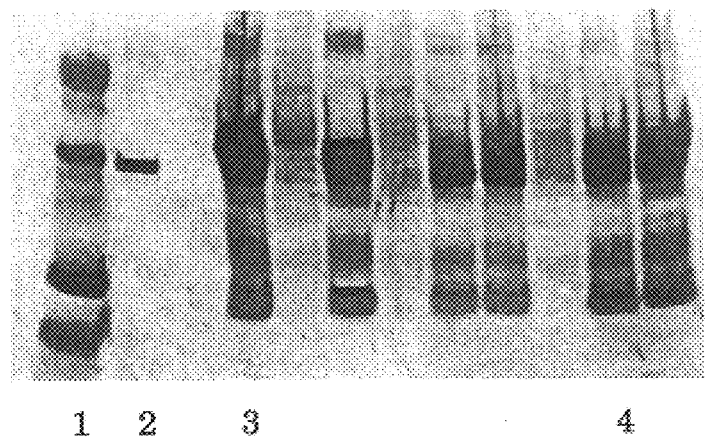

As illustrated in panels A and B of FIG. 5, pRAB-84-69 and PRSB-14, respectively, produced at least the same level of β-casein as that produced by pRJB36.

In particular, the same volume (10 μl) of cultures were loaded per lane. In panel A of FIG. 5, the intensity of the human beta-casein band from pRJB-36 in lane 3 is comparable to that from pRAB-84-69 in lane 4, indicating that at least as much protein is produced in the new constructs. In panel B of FIG. 5, the protein band from pRSB14 in lanes 4 and 5 is as intense as the band from pRJB36 in lane 3.

EXAMPLE VI

Determination of the Levels of β-casein Produced in Fermintation Using pRJB36 and pRAB84-69

A 2× sample buffer of 20 mM Tris-Cl, 2 mM EDTA, pH 8, containing 5% sodium dodecyl sulfate (SDS) and 10% β-mercaptoethanol and 0.01 (w/v) bromophenol blue was prepared. Whole broth samples from fermented cultures were diluted in the 2× sample buffer to give either ½, ¼, or ⅛ dilutions. The dilutions were mixed and heated at 100° C. for 5 minutes. The heated preparations were centrifuged at approximately 500×g for 30 seconds and 1 to 5 micrograms of beta-casein protein were loaded per lane via sample loading combs. Sample volumes of 0.3, 1.0 or 4.0 microliters/lane can be loaded on the gel. Twenty percent Phast Gels and Phast Gel SDS Buffer Strips were used. Gels were run on a Pharmacia PhastSystem (Pharmacia, Piscataway, N.J.). The separation parameters were:

| step 1: | 250 V | 10 mA | 3 watts | 15° C. | 1 volt hrs. |
|---|---|---|---|---|---|
| step 2: | 250 V | 1 mA | 3 watts | 15° C. | 1 volt hrs. |
| step 3: | 250 V | 10 mA | 3 watts | 15° C. | 95 volt hrs. |

The sample loading comb was put down at step 2 and brought back up at step 3.

Gels were stained with Pharmacia's PhastGel Blue R (Coomassie R 350) which was prepared by dissolving one tablet of PhastGel Blue R (Product #12-0518-01) in 80 ml of distilled water. The mixture was stirred for 10 minutes and then 120 ml of methanol and 200 ml of 20% (v/v) acetic acid were added. Stirring continued for 30 minutes and then the staining solution was filtered through a 0.45 micron membrane. Also prepared was the destaining solution [30% (v/v) methanol, 10% (v/v) acetic acid] and the storage solution [10% (v/v) glycerol, 10% (v/v) acetic acid]. After transferring the gel(s) to the staining unit, the following staining/destaining protocol was used:

| step 1: | staining solution | 8 minutes | 50° C. |
|---|---|---|---|
| step 2: | destaining solution | 7.4 minutes | 50° C. |
| step 3: | destaining solution | 11.4 minutes | 50° C. |
| step 4: | destaining solution | 13.4 minutes | 50° C. |
| step 5: | storage solution | 5 minutes | 50° C. |

To quantitate bands stained in gels, a Pharmacia UltroScan XL densitometer was used in conjunction with a GelScan XL software package. The densitometer uses a laser with a wavelength of 633 nm. The standard procedure involves the generation of a standard curve (either purified native or recombinant beta-casein) and comparison of the beta-casein bands of the various samples to this standard curve.

The following results were obtained from single experiments with HMS174(DE3)/pRJB36 and HMS174 (DE3)/pRSB-14 in five liter New Brunswick Scientific fermentors using the control protocol as well as from 5 experiments that cultured *E. coli* HMS174 (DE3)/pRAB84-69 in five liter New Brunswick Scientific fermentors using the control protocol. The results presented represent peak results rather than the final OD's and beta casein concentrations.

TABLE I

| Plasmid | Exp # | Run Time (hours) | Beta-Casein Conc. (g/l) | OD | Vol. (liters) |
|---|---|---|---|---|---|
| pRAB-84-69 | 97BC16 | 29.0 | 7.4 | 55.7 | 4.5 |
| pRAB-84-69 | 97BC17 | 28.0 | 8.8 | 52.4 | 4.5 |
| pRAB-84-69 | 97BC20 | 29.0 | 10.0 | 52.3 | 3.9 |
| pRAB-84-69 | 97BC23 | 36.0 | 8.6 | 53.0 | 4.4 |
| pRAB-84-69 | 97BC30 | 37.0 | 7.6 | 55.9 | 4.4 |
| pRSB-14 | 97BC22 | 45.0 | 1.8 | 60.1 | 4.3 |
| pRJB-36 | 97BC4 | 24.0 | 6.2 | 53.7 | 4.2 |

The above results illustrate that beta-casein was produced in HMS 174 (DE3)/pRAB-84-69 at a much higher level than in HMS 174 (DE3)/pRJB36. HMS 174 (DE3)/pRSB14, however, produced a much lower level of recombinant human β-casein than pRJB36. These results indicated that an improvement of the stability of the plasmid does not necessarily improve expression in the cultures.

EXAMPLE VII

Determination of Phosphorylation Pattern of Beta-casein

Figure 6:
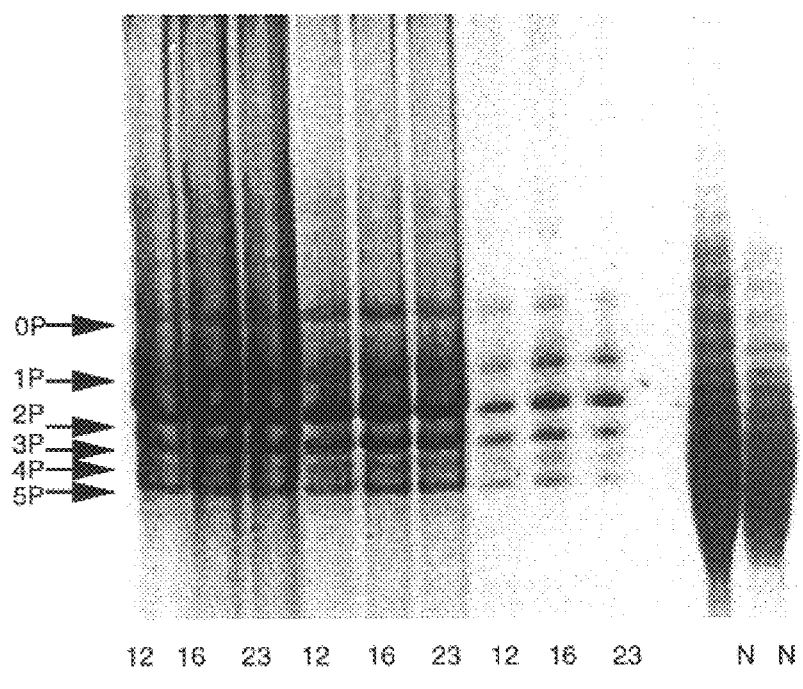
FIG. 6 represents the phosphorylation pattern of pRAB-84-69.

As can be observed from FIG. 6, the phosphorylation pattern of pRAB-84-69 was similar to that of native human β-casein.

EXAMPLE VIII

Determination of Processing at the Amino-terminus of Beta-casein

It was determined by N-terminal amino acid sequencing that the β-casein produced by the pRAB84-69 construct was correctly processed with arginine at the —NH2 terminus (see Table II below). Thus, active iminopeptidase produces recombinant human beta-casein with a properly processed N-terminus.

TABLE II

| Residue # | Protein Sequence Residue ID | PMOL |
|---|---|---|
| 1 | R | 73.3 |
| 2 | E | 52.1 |
| 3 | T | 35.8 |
| 4 | I | 48 |
| 5 | E | 34.4 |

EXAMPLE IX

Determination of Iminopeptidase Activity

The pellet was harvested from induced cultures by centrifugation at 10,000×g for 5 minutes at 4° C. The pellet was then French pressed in 50 mM Tris, pH 8.0, 1 mM EDTA, and 0.2 mM PMSF. The iminopeptidase substrate L-propyl-p-nitroanilide (pro-pNA; Bachem Bioscience, Inc.) was prepared at 6 mM in deionized water with the assistance of sonication. Forty microliters of the substrate solution was added to a cuvette containing 920 μl of 50 mM Tris, pH 8.0 and the contents mixed by inversion. Following a 5 minute incubation of the cuvette at 30° C. in a temperature regulated spectrophotometer, 40 μl of cell extract was added to the cuvette and the contents again mixed by inversion. The reaction at 30° C. was monitored for two minutes by following the increase in the absorbance at 410 nm. Rates of reaction were calculated by using an extinction coefficient of 9600 (Zevaco et al., *J. Appl. Bacteriol.* 68:357–366).

| Time (sec) | pRJB-36 410.0 nm | pRAB-84-69 410.0 nm |
|---|---|---|
| 0.0 | 0.5777 | 1.1469 |
| 30.0 | 1.2459 | 1.1925 |
| 60.0 | 1.3572 | 1.2007 |
| 90.0 | 1.3097 | 1.2305 |
| 120.00 | 1.3795 | 1.1936 |

Furthermore it was determined that the pep I enzyme activity was equivalent to that from pRAB-84-69.

What is claimed is:

1. A method of improving the genetic stability of a plasmid-containing cell during fermentation comprising the steps of: 1) transforming a cell with a vector comprising an isolated DNA sequence comprising a nucleotide sequence encoding human β-casein, wherein said nucleotide sequence is operably linked to a promoter, a nucleotide sequence encoding a first subunit of a kinase, a nucleotide sequence encoding a second subunit of said kinase, a nucleotide sequence encoding a peptidase and a nucleotide sequence encoding a bacterial resistance marker, 2) prior to fermentation, growing said cell in a culture utilized for inoculating a fermentor, 3) growing said cell in said fermentor, 4) inducing at least one of said nucleotide sequences present in said vector, and 5) completing fermentation for a time and under conditions suitable for optimal expression of said at least one nucleotide sequence, said method resulting in a cell having improved genetic stability during fermentation.

* * * * *

UNITED STATES PATENT AND TRADEMARK OFFICE
CERTIFICATE OF CORRECTION

PATENT NO. : 6,287,866 B1
DATED : September 11, 2001
INVENTOR(S) : Pradip Mukerji et al.

It is certified that error appears in the above-identified patent and that said Letters Patent is hereby corrected as shown below:

<u>Title page,</u>
Item [75], Inventors, replace "Amanda Eun-Yeong Leonard, Gahannna" with
-- Amanda Eun-Yeong Leonard, Gahanna --.

Signed and Sealed this

Fourth Day of June, 2002

*Attest:*

JAMES E. ROGAN
*Attesting Officer*     *Director of the United States Patent and Trademark Office*

SEQUENCE LISTING

```
<160> NUMBER OF SEQ ID NOS: 22

<210> SEQ ID NO 1
<211> LENGTH: 6873
<212> TYPE: DNA
<213> ORGANISM: Homo sapiens
<220> FEATURE:
<221> NAME/KEY: CDS
<222> LOCATION: (2094)...(2732)
<223> OTHER INFORMATION: HBNC in forward orientation
<221> NAME/KEY: CDS
<222> LOCATION: (2900)...(3544)
<223> OTHER INFORMATION: CKIIb in forward orientation
<221> NAME/KEY: CDS
<222> LOCATION: (3571)...(4743)
<223> OTHER INFORMATION: CKIIa in forward orientation
<221> NAME/KEY: CDS
<222> LOCATION: (6053)...(6868)
```

```
<223> OTHER INFORMATION: KANR - kanamycin resistance in forward
      orientation
<221> NAME/KEY: promoter
<222> LOCATION: (2014)...(2031)
<223> OTHER INFORMATION: T7 Promoter in forward orientation
<221> NAME/KEY: terminator
<222> LOCATION: (2803)...(2850)
<223> OTHER INFORMATION: T7 Terminator in forward orientation
<221> NAME/KEY: terminator
<222> LOCATION: (4824)...(4870)
<223> OTHER INFORMATION: T7 Terminator in forward orientation

<400> SEQUENCE: 1
tcgacctagt cctggctgat taaccagtca gacaacagct cttgatactt ggcattttcc      60
tggacaaaag gcatgtggcc gcagccggca aagagctccc agcgggcatt tggcaagtga     120
tcgtacatgc ttttagccac tagggagtg cacaagtcgt cagtgccgct ggtaatcaag      180
gccggcaagt ccaggtcctt taagcggtca gtgtactcat agccgtgcag gttgccaatc     240
ggcgtatatt cattagggcc ccagcctgtc aagtaggcca ggttgccgcc cttttttttg     300
cgcaaaactg gctccggcag gtccggcgta agcttgatgg cgtgctggtc catgaagtgg     360
gcattggccg cctggtaggc cggggagtcg tagttgccag ttgtttcagc ttccttgata     420
gcggcctgct cgcccttggg caggtacttg atcaagcggt gcagttcctg gctccaaagc     480
ttggcggagg ctaaagtgga ggagaggatc aggctcttga ccccttttagg ctggtagtcg     540 cacaggtaga tcaaagccag catcccgccc cagctttgcc ccaaaaggtg gatctggtca     600
aggcccagct gctctctgac attttccagc tccttgaccc aggtttgggc cgtgtaggct     660
gtttccgcct ggtcgtcggg gatgctggag ttgccgcagc ctaattggtc atacatgatg     720
acctggcggc cgcttttttc agcgacttgg tcgaggactt caaaatagtt gtgactgctg     780
ccgggcccgc cgtggagaag gaggagcggg cgcggtcag tagcctcgcc cacgatccgg      840
cagtaggttt gccaatttcc aaatggaaga tattttctg tgatttgcat cttgaattga      900
tccccgggaa ttctgtttcc tgtgtgaaat tgttatccgc tcacaattcc acacattata     960
cgagccgatg attaattgtc aacagctcat ttcagaatat tgccagaac cgttatgatg     1020 tcggcgcaaa aaacattatc cagaacggga gtgcgccttg agcgacacga attatgcagt     1080
gatttacgac ctgcacagcc ataccacagc ttccgatggc tgcctgacgc cagaagcatt     1140
ggtgcaccgt gcagtcgata agcccggatc aattcggatc gcttcacgac cacgctgatg     1200
agctttaccg cagctgcctc gcgcgtttcg gtgatgacgg tgaaaacctc tgacacatgc     1260
agctcccgga gacggtcaca gcttgtctgt aagcggatgc cgggagcaga caagcccgtc     1320
agggcgcgtc agcgggtgtt ggcgggtgtc ggggcgcagc catgacccag tcacgtagcg     1380
atagcggagt gtacgaacgc cagcaagacg tagcccagcg cgtcggccgc catgccggcg     1440
ataatggcct gcttctcgcc gaaacgtttg gtggcgggac cagtgacgaa ggcttgagcg     1500
agggcgtgca agattccgaa taccgcaagc gacaggccga tcatcgtcgc gctccagcga     1560
aagcggtcct cgccgaaaat gacccagagc gctgccggca cctgtcctac gagttgcatg     1620
ataaagaaga cagtcataag tgcggcgacg atagtcatgc cccgcgccca ccggaaggag     1680
ctgactgggt tgaaggctct caagggcatc ggtcgacgct ctcccttatg cgactcctgc     1740
attaggaagc agcccagtag taggttgagg ccgttgagca ccgccgccgc aaggaatggt     1800
gcatgcaagg agatggcgcc caacagtccc cggccacgg ggcctgccac catacccacg      1860
ccgaaacaag cgctcatgag cccgaagtgg cgagcccgat cttccccatc ggtgatgtcg     1920
gcgatatagg cgccagcaac cgcacctgtg gcgccggtga tgccggccac gatgcgtccg     1980
```

-continued

```
gcgtagagga tcgagatctc gatcccgcga aattaatacg actcactata gggagaccac    2040
aacggtttcc ctctagaaat aattttgttt aactttaaga aggagatata cat atg      2096
                                                          Met
                                                            1 ccg cgt gaa acc atc gaa tcc ctg agc tcg agc gaa gaa tcg atc acc    2144
Pro Arg Glu Thr Ile Glu Ser Leu Ser Ser Ser Glu Glu Ser Ile Thr
          5                  10                  15 gaa tac aaa cag aaa gtt gaa aaa gtt aaa cac gag gac cag cag caa    2192
Glu Tyr Lys Gln Lys Val Glu Lys Val Lys His Glu Asp Gln Gln Gln
         20                  25                  30 gga gag gat gaa cac cag gat aaa atc tac ccc tct ttc cag cca cag    2240
Gly Glu Asp Glu His Gln Asp Lys Ile Tyr Pro Ser Phe Gln Pro Gln
     35                  40                  45 cct ctg atc tat cca ttc gtt gaa cct atc ccc tat ggt ttt ctt cca    2288
Pro Leu Ile Tyr Pro Phe Val Glu Pro Ile Pro Tyr Gly Phe Leu Pro
 50                  55                  60                  65 caa aac att ctg cct ctt gct cag cct gct gtg gtg ctg cct gtc cct    2336
Gln Asn Ile Leu Pro Leu Ala Gln Pro Ala Val Val Leu Pro Val Pro
                 70                  75                  80 cag cct gaa ata atg gaa gtc cct aaa gct aaa gac act gtc tac act    2384
Gln Pro Glu Ile Met Glu Val Pro Lys Ala Lys Asp Thr Val Tyr Thr
             85                  90                  95 aag ggc aga gtg atg cct gtc ctt aaa tct cca acg ata ccc ttt ttt    2432
Lys Gly Arg Val Met Pro Val Leu Lys Ser Pro Thr Ile Pro Phe Phe
        100                 105                 110 gac cct caa atc cca aaa ctc act gat ctt gaa aat ctg cat ctt cct    2480
Asp Pro Gln Ile Pro Lys Leu Thr Asp Leu Glu Asn Leu His Leu Pro
    115                 120                 125 ctg cct ctg ctc cag ccc ttg atg cag cag gtc cct cag cct att cct    2528
Leu Pro Leu Leu Gln Pro Leu Met Gln Gln Val Pro Gln Pro Ile Pro
130                 135                 140                 145 cag act ctt gca ctt ccc cct cag ccc ctg tgg tct gtt cct cag ccc    2576
Gln Thr Leu Ala Leu Pro Pro Gln Pro Leu Trp Ser Val Pro Gln Pro
                150                 155                 160 aaa gtc ctg cct atc ccc cag caa gtg gtg ccc tac cct cag aga gct    2624
Lys Val Leu Pro Ile Pro Gln Gln Val Val Pro Tyr Pro Gln Arg Ala
            165                 170                 175 gtg cct gtt caa gcc ctt ctg ctc aac caa gaa ctt cta ctt aac ccc    2672
Val Pro Val Gln Ala Leu Leu Leu Asn Gln Glu Leu Leu Leu Asn Pro
        180                 185                 190 acc cac cag atc tac cct gtg act cag cca ctt gcc cca gtt cat aac    2720
Thr His Gln Ile Tyr Pro Val Thr Gln Pro Leu Ala Pro Val His Asn
    195                 200                 205 ccc att agt gtc taataaggat ccggctgcta acaaagcccg aaaggaagct       2772
Pro Ile Ser Val
210 gagttggctg ctgccaccgc tgagcaataa ctagcataac cccttggggc ctctaaacgg    2832 gtcttgaggg gttttttgct gaaaggagga actatatccg gatcgattaa ataaggagga   2892 ataacat atg agc agc tca gag gag gtg tcc tgg att tcc tgg ttc tgt    2941
        Met Ser Ser Ser Glu Glu Val Ser Trp Ile Ser Trp Phe Cys
            215                 220                 225 ggg ctc cgt ggc aat gaa ttc ttc tgt gaa gtg gat gaa gac tac atc    2989
Gly Leu Arg Gly Asn Glu Phe Phe Cys Glu Val Asp Glu Asp Tyr Ile
        230                 235                 240 cag gac aaa ttt aat ctt act gga ctc aat gag cag gtc cct cac tac    3037
Gln Asp Lys Phe Asn Leu Thr Gly Leu Asn Glu Gln Val Pro His Tyr
    245                 250                 255
```

```
                                                                    -continued cga caa gct cta gac atg atc ttg gac ctg gag cct gat gaa gaa ctg    3085
Arg Gln Ala Leu Asp Met Ile Leu Asp Leu Glu Pro Asp Glu Glu Leu
260                 265                 270                 275 gaa gac aac ccc aac cag agt gac ctg att gag cag gca gcc gag atg    3133
Glu Asp Asn Pro Asn Gln Ser Asp Leu Ile Glu Gln Ala Ala Glu Met
                280                 285                 290 ctt tat gga ttg atc cac gcc cgc tac atc ctt acc aac cgt ggc atc    3181
Leu Tyr Gly Leu Ile His Ala Arg Tyr Ile Leu Thr Asn Arg Gly Ile
            295                 300                 305 gcc cag atg ttg gaa aag tac cag caa gga gac ttt ggt tac tgt cct    3229
Ala Gln Met Leu Glu Lys Tyr Gln Gln Gly Asp Phe Gly Tyr Cys Pro
        310                 315                 320 cgt gtg tac tgt gag aac cag cca atg ctt ccc att ggc ctt tca gac    3277
Arg Val Tyr Cys Glu Asn Gln Pro Met Leu Pro Ile Gly Leu Ser Asp
    325                 330                 335 atc cca ggt gaa gcc atg gtg aag ctc tac tgc ccc aag tgc atg gat    3325
Ile Pro Gly Glu Ala Met Val Lys Leu Tyr Cys Pro Lys Cys Met Asp
340                 345                 350                 355 gtg tac aca ccc aag tca tca aga cac cat cac acg gat ggc gcc tac    3373
Val Tyr Thr Pro Lys Ser Ser Arg His His His Thr Asp Gly Ala Tyr
                360                 365                 370 ttc ggc act ggt ttc cct cac atg ctc ttc atg gtg cat ccc gag tac    3421
Phe Gly Thr Gly Phe Pro His Met Leu Phe Met Val His Pro Glu Tyr
            375                 380                 385 cgg ccc aag aga cct gcc aac cag ttt gtg ccc agg ctc tac ggt ttc    3469
Arg Pro Lys Arg Pro Ala Asn Gln Phe Val Pro Arg Leu Tyr Gly Phe
        390                 395                 400 aag atc cat gcg atg gcc tac cag ctg cag ctc caa gcc gcc agc aac    3517
Lys Ile His Ala Met Ala Tyr Gln Leu Gln Leu Gln Ala Ala Ser Asn
    405                 410                 415 ttc aag agc cca gtc aag acg att cgc taagtcgaca agaaggagat          3564
Phe Lys Ser Pro Val Lys Thr Ile Arg
420                 425 atacat atg tcg gga ccc gtg cca agc agg gcc aga gtt tac aca gat    3612
       Met Ser Gly Pro Val Pro Ser Arg Ala Arg Val Tyr Thr Asp
           430                 435                 440 gtt aat aca cac aga cct cga gaa tac tgg gat tac gag tca cat gtg    3660
Val Asn Thr His Arg Pro Arg Glu Tyr Trp Asp Tyr Glu Ser His Val
            445                 450                 455 gtg gaa tgg gga aat caa gat gac tac cag ctg gtt cga aaa tta ggc    3708
Val Glu Trp Gly Asn Gln Asp Asp Tyr Gln Leu Val Arg Lys Leu Gly
        460                 465                 470 cga ggt aaa tac agt gaa gta ttt gaa gcc atc aac atc aca aat aat    3756
Arg Gly Lys Tyr Ser Glu Val Phe Glu Ala Ile Asn Ile Thr Asn Asn
475                 480                 485                 490 gaa aaa gtt gtt gtt aaa att ctc aag cca gta aaa aag aaa aaa att    3804
Glu Lys Val Val Val Lys Ile Leu Lys Pro Val Lys Lys Lys Lys Ile
                495                 500                 505 aag cgt gaa ata aag att ttg gag aat ttg aga gga ggt ccc aac atc    3852
Lys Arg Glu Ile Lys Ile Leu Glu Asn Leu Arg Gly Gly Pro Asn Ile
            510                 515                 520 atc aca ctg gca gac att gta aaa gac cct gtg tca cga acc ccc gcc    3900
Ile Thr Leu Ala Asp Ile Val Lys Asp Pro Val Ser Arg Thr Pro Ala
        525                 530                 535 ttg gtt ttt gaa cac gta aac aac aca gac ttc aag caa ttg tac cag    3948
Leu Val Phe Glu His Val Asn Asn Thr Asp Phe Lys Gln Leu Tyr Gln
    540                 545                 550 acg tta aca gac tat gat att cga ttt tac atg tat gag att ctg aag    3996
Thr Leu Thr Asp Tyr Asp Ile Arg Phe Tyr Met Tyr Glu Ile Leu Lys
555                 560                 565                 570
```

```
gcc ctg gat tat tgt cac agc atg gga att atg cac aga gat gtc aag    4044
Ala Leu Asp Tyr Cys His Ser Met Gly Ile Met His Arg Asp Val Lys
                575                 580                 585 ccc cat aat gtc atg att gat cat gag cac aga aag cta cga cta ata    4092
Pro His Asn Val Met Ile Asp His Glu His Arg Lys Leu Arg Leu Ile
                590                 595                 600 gac tgg ggt ttg gct gag ttt tat cat cct ggc caa gaa tat aat gtc    4140
Asp Trp Gly Leu Ala Glu Phe Tyr His Pro Gly Gln Glu Tyr Asn Val
                605                 610                 615 cga gtt gct tcc cga tac ttc aaa ggt cct gag cta ctt gta gac tat    4188
Arg Val Ala Ser Arg Tyr Phe Lys Gly Pro Glu Leu Leu Val Asp Tyr
        620                 625                 630 cag atg tac gat tat agt ttg gat atg tgg agt ttg ggt tgt atg ctg    4236
Gln Met Tyr Asp Tyr Ser Leu Asp Met Trp Ser Leu Gly Cys Met Leu
635                 640                 645                 650 gca agt atg atc ttt cgg aag gag cca ttt ttc cat gga cat gac aat    4284
Ala Ser Met Ile Phe Arg Lys Glu Pro Phe Phe His Gly His Asp Asn
                655                 660                 665 tat gat cag ttg gtg agg ata gcc aag gtt ctg ggg aca gaa gat tta    4332
Tyr Asp Gln Leu Val Arg Ile Ala Lys Val Leu Gly Thr Glu Asp Leu
                670                 675                 680 tat gac tat att gac aaa tac aac att gaa tta gat cca cgt ttc aat    4380
Tyr Asp Tyr Ile Asp Lys Tyr Asn Ile Glu Leu Asp Pro Arg Phe Asn
                685                 690                 695 gat atc ttg ggc aga cac tct cga aag cga tgg gaa cgc ttt gtc cac    4428
Asp Ile Leu Gly Arg His Ser Arg Lys Arg Trp Glu Arg Phe Val His
        700                 705                 710 agt gaa aat cag cac ctt gtc agc cct gag gcc ttg gat ttc ctg gac    4476
Ser Glu Asn Gln His Leu Val Ser Pro Glu Ala Leu Asp Phe Leu Asp
715                 720                 725                 730 aaa ctg ctg cga tat gac cac cag tca cgg ctt act gca aga gag gca    4524
Lys Leu Leu Arg Tyr Asp His Gln Ser Arg Leu Thr Ala Arg Glu Ala
                735                 740                 745 atg gag cac ccc tat ttc tac act gtt gtg aag gac cag gct cga atg    4572
Met Glu His Pro Tyr Phe Tyr Thr Val Val Lys Asp Gln Ala Arg Met
                750                 755                 760 ggt tca tct agc atg cca ggg ggc agt acg ccc gtc agc agc gcc aat    4620
Gly Ser Ser Ser Met Pro Gly Gly Ser Thr Pro Val Ser Ser Ala Asn
                765                 770                 775 atg atg tca ggg att tct tca gtg cca acc cct tca ccc ctt gga cct    4668
Met Met Ser Gly Ile Ser Ser Val Pro Thr Pro Ser Pro Leu Gly Pro
780                 785                 790 ctg gca ggc tca cca gtg att gct gct gcc aac ccc ctt ggg atg cct    4716
Leu Ala Gly Ser Pro Val Ile Ala Ala Ala Asn Pro Leu Gly Met Pro
795                 800                 805                 810 gtt cca gct gcc gct ggc gct cag cag taagctagcg tcgacggatc         4763
Val Pro Ala Ala Ala Gly Ala Gln Gln
                815 cggctgctaa caaagcccga aggaagctg agttggctgc tgccaccgct gagcaataac    4823 tagcataacc ccttgggggcc tctaaacggg tcttgagggg ttttttgctg aaaggaggaa   4883 ctatatccgg atatcccgca agaggcccgg cagtaccgg ataaccaagc ctatgcctac    4943 agcatccagg gtgacggtgc cgaggatgac gatgagcgca ttgttagatt tcatacacgg   5003 tgcctgactg cgttagcaat ttaactgtga taaactaccg cattaaagct tactggctta   5063 actatgcggc atcagagcag attgtactga gagtgcacca tatatgcggt gtgaaatacc   5123 gcacagatgc gtaaggagaa aataccgcat caggcgctct tccgcttcct cgctcactga   5183 ctcgctgcgc tcggtcgttc ggctgcggcg agcggtatca gctcactcaa aggcggtaat   5243
```

-continued

```
acgttatcc acagaatcag gggataacgc aggaaagaac atgtgagcaa aaggccagca    5303
aaaggccagg aaccgtaaaa aggccgcgtt gctggcgttt ttccataggc tccgccccc     5363 tgacgagcat cacaaaaatc gacgctcaag tcagaggtgg cgaaacccga caggactata    5423
aagataccag gcgtttcccc ctggaagctc cctcgtgcgc tctcctgttc cgaccctgcc    5483
gcttaccgga tacctgtccg cctttctccc ttcgggaagc gtggcgcttt ctcatagctc    5543
acgctgtagg tatctcagtt cggtgtaggt cgttcgctcc aagctgggct gtgtgcacga    5603
accccccgtt cagcccgacc gctgcgcctt atccggtaac tatcgtcttg agtccaaccc    5663
ggtaagacac gacttatcgc cactggcagc agccactggt aacaggatta gcagagcgag    5723
gtatgtaggc ggtgctacag agttcttgaa gtggtggcct aactacggct acactagaag    5783
gacagtattt ggtatctgcg ctctgctgaa gccagttacc ttcggaaaaa gagttggtag    5843
ctcttgatcc ggcaaacaaa ccaccgctgg tagcggtggt ttttttgttt gcaagcagca    5903
gattacgcgc agaaaaaaag gatctcaaga agatcctttg atcttttcta cggggtctga    5963
cgctcagtgg aacgaaaact cacgttaagg gattttggtc atgaacaata aaactgtctg    6023
cttacataaa cagtaataca agggtgtt atg agc cat att caa cgg gaa acg       6076
                                Met Ser His Ile Gln Arg Glu Thr
                                    820             825 tct tgc tct agg ccg cga tta aat tcc aac atg gat gct gat tta tat      6124
Ser Cys Ser Arg Pro Arg Leu Asn Ser Asn Met Asp Ala Asp Leu Tyr
        830                 835                 840 ggg tat aaa tgg gct cgc gat aat gtc ggg caa tca ggt gcg aca atc      6172
Gly Tyr Lys Trp Ala Arg Asp Asn Val Gly Gln Ser Gly Ala Thr Ile
845                 850                 855 tat cga ttg tat ggg aag ccc gat gcg cca gag ttg ttt ctg aaa cat      6220
Tyr Arg Leu Tyr Gly Lys Pro Asp Ala Pro Glu Leu Phe Leu Lys His
860                 865                 870                 875 ggc aaa ggt agc gtt gcc aat gat gtt aca gat gag atg gtc aga cta      6268
Gly Lys Gly Ser Val Ala Asn Asp Val Thr Asp Glu Met Val Arg Leu
                880                 885                 890 aac tgg ctg acg gaa ttt atg cct ctt ccg acc atc aag cat ttt atc      6316
Asn Trp Leu Thr Glu Phe Met Pro Leu Pro Thr Ile Lys His Phe Ile
            895                 900                 905 cgt act cct gat gat gca tgg tta ctc acc act gcg atc ccc ggg aaa      6364
Arg Thr Pro Asp Asp Ala Trp Leu Leu Thr Thr Ala Ile Pro Gly Lys
        910                 915                 920 aca gca ttc cag gta tta gaa gaa tat cct gat tca ggt gaa aat att      6412
Thr Ala Phe Gln Val Leu Glu Glu Tyr Pro Asp Ser Gly Glu Asn Ile
925                 930                 935 gtt gat gcg ctg gca gtg ttc ctg cgc cgg ttg cat tcg att cct gtt      6460
Val Asp Ala Leu Ala Val Phe Leu Arg Arg Leu His Ser Ile Pro Val
940                 945                 950                 955 tgt aat tgt cct ttt aac agc gat cgc gta ttt cgt ctc gct cag gcg      6508
Cys Asn Cys Pro Phe Asn Ser Asp Arg Val Phe Arg Leu Ala Gln Ala
                960                 965                 970 caa tca cga atg aat aac ggt ttg gtt gat gcg agt gat ttt gat gac      6556
Gln Ser Arg Met Asn Asn Gly Leu Val Asp Ala Ser Asp Phe Asp Asp
            975                 980                 985 gag cgt aat ggc tgg cct gtt gaa caa gtc tgg aaa gaa atg cat aaa      6604
Glu Arg Asn Gly Trp Pro Val Glu Gln Val Trp Lys Glu Met His Lys
        990                 995                 1000 ctt ttg cca ttc tca ccg gat tca gtc gtc act cat ggt gat ttc tca      6652
Leu Leu Pro Phe Ser Pro Asp Ser Val Val Thr His Gly Asp Phe Ser
    1005                1010                1015
```

```
ctt gat aac ctt att ttt gac gag ggg aaa tta ata ggt tgt att gat    6700
Leu Asp Asn Leu Ile Phe Asp Glu Gly Lys Leu Ile Gly Cys Ile Asp
1020                1025                1030                1035 gtt gga cga gtc gga atc gca gac cga tac cag gat ctt gcc atc cta    6748
Val Gly Arg Val Gly Ile Ala Asp Arg Tyr Gln Asp Leu Ala Ile Leu
            1040                1045                1050 tgg aac tgc ctc ggt gag ttt tct cct tca tta cag aaa cgg ctt ttt    6796
Trp Asn Cys Leu Gly Glu Phe Ser Pro Ser Leu Gln Lys Arg Leu Phe
        1055                1060                1065 caa aaa tat ggt att gat aat cct gat atg aat aaa ttg cag ttt cat    6844
Gln Lys Tyr Gly Ile Asp Asn Pro Asp Met Asn Lys Leu Gln Phe His
    1070                1075                1080 ttg atg ctc gat gag ttt ttc taa gaatt                              6873
Leu Met Leu Asp Glu Phe Phe *
    1085                1090
```

<210> SEQ ID NO 2
<211> LENGTH: 213
<212> TYPE: PRT
<213> ORGANISM: Homo sapiens

<400> SEQUENCE: 2

```
Met Pro Arg Glu Thr Ile Glu Ser Leu Ser Ser Glu Gly Ser Ile
 1               5                  10                  15

Thr Glu Tyr Lys Gln Lys Val Glu Lys Val Lys His Glu Asp Gln Gln
                20                  25                  30

Gln Gly Glu Asp Glu His Gln Asp Lys Ile Tyr Pro Ser Phe Gln Pro
            35                  40                  45

Gln Pro Leu Ile Tyr Pro Phe Val Glu Pro Ile Pro Tyr Gly Phe Leu
        50                  55                  60

Pro Gln Asn Ile Leu Pro Leu Ala Gln Pro Ala Val Val Leu Pro Val
    65                  70                  75                  80

Pro Gln Pro Glu Ile Met Glu Val Pro Lys Ala Lys Asp Thr Val Tyr
                85                  90                  95

Thr Lys Gly Arg Val Met Pro Val Leu Lys Ser Pro Thr Ile Pro Phe
            100                 105                 110

Phe Asp Pro Gln Ile Pro Lys Leu Thr Asp Leu Glu Asn Leu His Leu
        115                 120                 125

Pro Leu Pro Leu Leu Gln Pro Leu Met Gln Gln Val Pro Gln Pro Ile
    130                 135                 140

Pro Gln Thr Leu Ala Leu Pro Pro Gln Pro Leu Trp Ser Val Pro Gln
145                 150                 155                 160

Pro Lys Val Leu Pro Ile Pro Gln Gln Val Val Pro Tyr Pro Gln Arg
                165                 170                 175

Ala Val Pro Val Gln Ala Leu Leu Leu Asn Gln Glu Leu Leu Leu Asn
            180                 185                 190

Pro Thr His Gln Ile Tyr Pro Val Thr Gln Pro Leu Ala Pro Val His
        195                 200                 205

Asn Pro Ile Ser Val
    210
```

<210> SEQ ID NO 3
<211> LENGTH: 215
<212> TYPE: PRT
<213> ORGANISM: Homo sapiens

```
<400> SEQUENCE: 3

Met Ser Ser Ser Glu Val Ser Trp Ile Ser Trp Phe Cys Gly Leu
 1               5                  10                  15

Arg Gly Asn Glu Phe Phe Cys Glu Val Asp Glu Asp Tyr Ile Gln Asp
            20                  25                  30

Lys Phe Asn Leu Thr Gly Leu Asn Glu Gln Val Pro His Tyr Arg Gln
            35                  40                  45

Ala Leu Asp Met Ile Leu Asp Leu Glu Pro Asp Glu Leu Glu Asp
 50                  55                  60

Asn Pro Asn Gln Ser Asp Leu Ile Glu Gln Ala Ala Glu Met Leu Tyr
 65                  70                  75                  80

Gly Leu Ile His Ala Arg Tyr Ile Leu Thr Asn Arg Gly Ile Ala Gln
                85                  90                  95

Met Leu Glu Lys Tyr Gln Gln Gly Asp Phe Gly Tyr Cys Pro Arg Val
                100                 105                 110

Tyr Cys Glu Asn Gln Pro Met Leu Pro Ile Gly Leu Ser Asp Ile Pro
            115                 120                 125

Gly Glu Ala Met Val Lys Leu Tyr Cys Pro Lys Cys Met Asp Val Tyr
 130                 135                 140

Thr Pro Lys Ser Ser Arg His His His Thr Asp Gly Ala Tyr Phe Gly
145                 150                 155                 160

Thr Gly Phe Pro His Met Leu Phe Met Val His Pro Glu Tyr Arg Pro
                165                 170                 175

Lys Arg Pro Ala Asn Gln Phe Val Pro Arg Leu Tyr Gly Phe Lys Ile
                180                 185                 190

His Ala Met Ala Tyr Gln Leu Gln Leu Gln Ala Ala Ser Asn Phe Lys
                195                 200                 205

Ser Pro Val Lys Thr Ile Arg
        210                 215

<210> SEQ ID NO 4
<211> LENGTH: 391
<212> TYPE: PRT
<213> ORGANISM: Homo sapiens

<400> SEQUENCE: 4

Met Ser Gly Pro Val Pro Ser Arg Ala Arg Val Tyr Thr Asp Val Asn
 1               5                  10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
            35                  40                  45

Lys Tyr Ser Glu Val Phe Glu Ala Ile Asn Ile Thr Asn Asn Glu Lys
 50                  55                  60

Val Val Val Lys Ile Leu Lys Pro Val Lys Lys Lys Ile Lys Arg
 65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
            115                 120                 125

Thr Asp Tyr Asp Ile Arg Phe Tyr Met Tyr Glu Ile Leu Lys Ala Leu
 130                 135                 140
```

-continued

```
Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
    290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Asn Pro Leu Gly Met Pro Val Pro
    370                 375                 380

Ala Ala Ala Gly Ala Gln Gln
385                 390

<210> SEQ ID NO 5
<211> LENGTH: 271
<212> TYPE: PRT
<213> ORGANISM: Homo sapiens

<400> SEQUENCE: 5

Met Ser His Ile Gln Arg Glu Thr Ser Cys Ser Arg Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125
```

```
Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
            195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270

<210> SEQ ID NO 6
<211> LENGTH: 8430
<212> TYPE: DNA
<213> ORGANISM: Homo sapiens
<220> FEATURE:
<221> NAME/KEY: CDS
<222> LOCATION: (6124)...(6939)
<223> OTHER INFORMATION: KANR - kanamycin resistance in forward
      orientation

<400> SEQUENCE: 6
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatcga taagctttaa tgcggtagtt tatcacagtt aaattgctaa cgcagtcagg     240
caccgtgtat gaaatctaac aatgcgctca tcgtcatcct cggcaccgtc accctggatg     300
ctgtaggcat aggcttggtt atgccggtac tgccgggcct cttgcgggat atccggatat     360
agttcctcct ttcagcaaaa aacccctcaa gacccgttta gaggccccaa ggggttatgc     420
tagttattgc tcagcggtgg cagcagccaa ctcagcttcc tttcgggctt tgttagcagc     480
cggatccgtc gacgctagct tactgctgag cgccagcggc agctggaaca ggcatcccaa     540
gggggttggc agcagcaatc actggtgagc ctgccagagg tccaagggt gaaggggttg      600 gcactgaaga atccctgac atcatattgg cgctgctgac gggcgtactg ccccctggca     660
tgctagatga acccattcga gcctggtcct tcacaacagt gtagaaatag gggtgctcca     720
ttgcctctct tgcagtaagc cgtgactggt ggtcatatcg cagcagtttg tccaggaaat     780
ccaaggcctc agggctgaca aggtgctgat tttcactgtg acaaagcgt tcccatcgct     840 ttcgagagtg tctgcccaag atatcattga acgtggatc taattcaatg ttgtatttgt     900
caatatagtc atataaatct tctgtcccca gaaccttggc tatcctcacc aactgatcat     960
aattgtcatg tccatggaaa atggctcct tccgaaagat catacttgcc agcatacaac    1020
ccaaactcca catatccaaa ctataatcgt acatctgata gtctacaagt agctcaggac    1080
ctttgaagta tcgggaagca actcggacat tatattcttg gccaggatga taaaactcag    1140
ccaaacccca gtctattagt cgtagctttc tgtgctcatg atcaatcatg acattatggg    1200
```

-continued

```
gcttgacatc tctgtgcata attcccatgc tgtgacaata atccaggccc ttcagaatct    1260
catacatgta aaatcgaata tcatagtctg ttaacgtctg gtacaattgc ttgaagtctg    1320
tgttgtttac gtgttcaaaa accaaggcgg gggttcgtga cacagggtct tttacaatgt    1380
ctgccagtgt gatgatgttg ggacctcctc tcaaattctc caaaatcttt atttcacgct    1440
taattttctt ctttttttact ggcttgagaa ttttaacaac aacttttca ttatttgtga    1500 tgttgatggc ttcaaatact tcactgtatt tacctcggcc taattttcga accagctggt    1560
agtcatcttg atttccccat ccaccacat gtgactcgta atcccagtat tctcgaggtc    1620
tgtgtgtatt aacatctgtg taaactctgg ccctgcttgg cacgggtccc gacatatgta    1680
tatctccttc ttgtcgactt agcgaatcgt cttgactggg ctcttgaagt tgctggcggc    1740
ttggagctgc agctggtagg ccatcgcatg gatcttgaaa ccgtagagcc tgggcacaaa    1800
ctggttggca ggtctcttgg gccggtactc gggatgcacc atgaagagca tgtgagggaa    1860
accagtgccg aagtaggcgc catccgtgtg atggtgtctt gatgacttgg gtgtgtacac    1920
atccatgcac ttggggcagt agagcttcac catggcttca cctgggatgt ctgaaaggcc    1980
aatgggaagc attggctggt tctcacagta cacacgagga cagtaaccaa agtctccttg    2040
ctggtacttt tccaacatct gggcgatgcc acgttggta aggatgtagc gggcgtggat    2100
caatccataa agcatctcgg ctgcctgctc aatcaggtca ctctggttgg ggttgtcttc    2160
cagttcttca tcaggctcca ggtccaagat catgtctaga gcttgtcggt agtgagggac    2220
ctgctcattg agtccagtaa gattaaattt gtcctggatg tagtcttcat ccacttcaca    2280
gaagaattca ttgccacgga gcccacagaa ccaggaaatc caggacacct cctctgagct    2340
gctcatatgt tattcctcct tatttaatcg atccggatat agttcctcct ttcagcaaaa    2400 aaccctcaa gacccgttta gaggccccaa ggggttatgc tagttattgc tcagcggtgg    2460
cagcagccaa ctcagcttcc tttcgggctt tgttagcagc cggatcctta ttagacacta    2520
atggggttat gaactggggc aagtggctga gtcacagggt agatctggtg gtgggggtta    2580
agtagaagtt cttggttgag cagaagggct tgaacaggca cagctctctg agggtagggc    2640
accacttgct gggggatagg caggactttg ggctgaggaa cagaccacag gggctgaggg    2700
ggaagtgcaa gagtctgagg aataggctga gggacctgct gcatcaaggg ctggagcaga    2760
ggcagaggaa gatgcagatt ttcaagatca gtgagttttg ggatttgagg gtcaaaaaag    2820
ggtatcgttg gagatttaag gacaggcatc actctgccct tagtgtagac agtgtcttta    2880
gctttaggga cttccattat ttcaggctga gggacaggca gcaccacagc aggctgagca    2940
agaggcagaa tgttttgtgg aagaaaacca tagggggatag gttcaacgaa tggatagatc    3000
agaggctgtg gctggaaaga ggggtagatt ttatcctggt gttcatcctc tccttgctgc    3060
tggtcctcgt gtttaacttt ttcaactttc tgtttgtatt cggtgatcga ttcttcgctc    3120
gagctcaggg attcgatggt ttcacgtggc atatgtatat ctccttctta aagttaaaca    3180
aaattatttc tagagggaaa ccgttgtggt ctccctatag tgagtcgtat taatttcgcg    3240
ggatcgagat ctcgatcctc tacgccggac gcatcgtggc cggcatcacc ggcgccacag    3300
gtgcggttgc tggcgcctat atcgccgaca tcaccgatgg ggaagatcgg gctcgccact    3360
tcgggctcat gagcgcttgt ttcggcgtgg gtatggtggc aggccccgtg gccggggggac    3420 tgttgggcgc catctccttg catgcaccat tccttgcggc ggcggtgctc aacggcctca    3480
acctactact gggctgcttc ctaatgcagg agtcgcataa gggagagcgt cgaccgatgc    3540
ccttgagagc cttcaaccca gtcagctcct tccggtgggc gcggggcatg actatcgtcg    3600
```

```
ccgcacttat gactgtcttc tttatcatgc aactcgtagg acaggtgccg gcagcgctct    3660
gggtcatttt cggcgaggac cgctttcgct ggagcgcgac gatgatcggc ctgtcgcttg    3720
cggtattcgg aatcttgcac gccctcgctc aagccttcgt cactggtccc gccaccaaac    3780
gtttcggcga gaagcaggcc attatcgccg gcatggcggc cgacgcgctg ggctacgtct    3840
tgctggcgtt cgcgacgcga ggctggatgg ccttccccat tatgattctt ctcgcttccg    3900
gcggcatcgg gatgcccgcg ttgcaggcca tgctgtccag gcaggtagat gacgaccatc    3960
agggacagct caaggatcg ctcgcggctc ttaccagcct aacttcgatc actgaccgc     4020
tgatcgtcac ggcgatttat gccgcctcgg cgagcacatg gaacgggttg gcatggattg    4080
taggcgccgc cctataccct gtctgcctcc ccgcgttgcg tcgcggtgca tggagccggg    4140
ccacctcgac ctgaatggaa gccggcggca cctcgctaac ggattcacca ctccaagaat    4200
tggagccaat caattcttgc ggagaactgt gaatgcgcaa accaacccct ggcagaacat    4260
atccatcgcg tccgccatct ccagcagccg cacgcggcgc atctcgggca gcgttgggtc    4320
ctggccacgg gtgcgcatga tcgtgctcct gtcgttgagg acccggctag gctggcgggg    4380
ttgccttact ggttagcaga atgaatcacc gatacgcgag cgaacgtgaa gcgactgctg    4440
ctgcaaaacg tctgcgacct gagcaacaac atgaatggtc ttcggtttcc gtgtttcgta    4500
aagtctggaa acgcggaagt cagcgccctg caccattatg ttccggatct gcatcgcagg    4560
atgctgctgg ctaccctgtg aacacctac atctgtatta acgaagcgct ggcattgacc     4620
ctgagtgatt tttctctggt cccgccgcat ccataccgcc agttgtttac cctcacaacg    4680
ttccagtaac cggcatgtt catcatcagt aacccgtatc gtgagcatcc tctctcgttt     4740
catcggtatc attaccccca tgaacagaaa tccccttac acggaggcat cagtgaccaa     4800
acaggaaaaa accgccctta acatggcccg ctttatcaga agccagacat taacgcttct    4860
ggagaaactc aacgagctgg acgcggatga acaggcagca atctgtgaat cgcttcacga    4920
ccacgctgat gagctttacc gcagctgcct cgcgcgtttc ggtgatgacg gtgaaaacct    4980
ctgacacatg cagctcccgg agacggtcac agcttgtctg taagcggatg ccgggagcag    5040
acaagcccgt cagggcgcgt cagcgggtgt tggcgggtgt cggggcgcag ccatgaccca    5100
gtcacgtagc gatagcggag tgtatactgg cttaactatg cggcatcaga gcagattgta    5160
ctgagagtgc accatatatg cggtgtgaaa taccgcacag atgcgtaagg agaaaatacc    5220
gcatcaggcg ctcttccgct tcctcgctca ctgactcgct gcgctcggtc gttcggctgc    5280
ggcgagcggt atcagctcac tcaaaggcgg taatacggtt atccacagaa tcagggata    5340
acgcaggaaa gaacatgtga gcaaaaggcc agcaaaaggc caggaaccgt aaaaaggccg    5400
cgttgctggc gttttccat aggctccgcc ccctgacga gcatcacaaa aatcgacgct     5460
caagtcagag gtggcgaaac ccgacaggac tataaagata ccaggcgttt ccccctggaa    5520
gctccctcgt gcgctctcct gttccgaccc tgccgcttac cggatacctg tccgcctttc    5580
tcccttcggg aagcgtggcg ctttctcata gctcacgctg taggtatctc agttcggtgt    5640
aggtcgttcg ctccaagctg ggctgtgtgc acgaaccccc cgttcagccc gaccgctgcg    5700
ccttatccgg taactatcgt cttgagtcca acccggtaag acacgactta tcgccactgg    5760
cagcagccac tggtaacagg attagcagag cgaggtatgt aggcggtgct acagagttct    5820
tgaagtggtg gcctaactac ggctacacta aaggacagt atttggtatc tgcgctctgc     5880
tgaagccagt taccttcgga aaaagagttg gtagctcttg atccggcaaa caaaccaccg    5940
ctggtagcgg tggttttttt gtttgcaagc agcagattac gcgcagaaaa aaggatctc    6000
```

```
aagaagatcc tttgatcttt tctacggggt ctgacgctca gtggaacgaa aactcacgtt      6060
aagggatttt ggtcatgaac aataaaactg tctgcttaca taaacagtaa tacaagggt       6120 gtt atg agc cat att caa cgg gaa acg tct tgc tcg agg ccg cga tta       6168
    Met Ser His Ile Gln Arg Glu Thr Ser Cys Ser Arg Pro Arg Leu
    1               5                   10                  15 aat tcc aac atg gat gct gat tta tat ggg tat aaa tgg gct cgc gat       6216
Asn Ser Asn Met Asp Ala Asp Leu Tyr Gly Tyr Lys Trp Ala Arg Asp
                20                  25                  30 aat gtc ggg caa tca ggt gcg aca atc tat cga ttg tat ggg aag ccc       6264
Asn Val Gly Gln Ser Gly Ala Thr Ile Tyr Arg Leu Tyr Gly Lys Pro
            35                  40                  45 gat gcg cca gag ttg ttt ctg aaa cat ggc aaa ggt agc gtt gcc aat       6312
Asp Ala Pro Glu Leu Phe Leu Lys His Gly Lys Gly Ser Val Ala Asn
        50                  55                  60 gat gtt aca gat gag atg gtc aga cta aac tgg ctg acg gaa ttt atg       6360
Asp Val Thr Asp Glu Met Val Arg Leu Asn Trp Leu Thr Glu Phe Met
    65                  70                  75 cct ctt ccg acc atc aag cat ttt atc cgt act cct gat gat gca tgg       6408
Pro Leu Pro Thr Ile Lys His Phe Ile Arg Thr Pro Asp Asp Ala Trp
80                  85                  90                  95 tta ctc acc act gcg atc ccc ggg aaa aca gca ttc cag gta tta gaa       6456
Leu Leu Thr Thr Ala Ile Pro Gly Lys Thr Ala Phe Gln Val Leu Glu
                100                 105                 110 gaa tat cct gat tca ggt gaa aat att gtt gat gcg ctg gca gtg ttc       6504
Glu Tyr Pro Asp Ser Gly Glu Asn Ile Val Asp Ala Leu Ala Val Phe
            115                 120                 125 ctg cgc cgg ttg cat tcg att cct gtt tgt aat tgt cct ttt aac agc       6552
Leu Arg Arg Leu His Ser Ile Pro Val Cys Asn Cys Pro Phe Asn Ser
        130                 135                 140 gat cgc gta ttt cgt ctc gct cag gcg caa tca cga atg aat aac ggt       6600
Asp Arg Val Phe Arg Leu Ala Gln Ala Gln Ser Arg Met Asn Asn Gly
    145                 150                 155 ttg gtt gat gcg agt gat ttt gat gac gag cgt aat ggc tgg cct gtt       6648
Leu Val Asp Ala Ser Asp Phe Asp Asp Glu Arg Asn Gly Trp Pro Val
160                 165                 170                 175 gaa caa gtc tgg aaa gaa atg cat aag ctt ttg cca ttc tca ccg gat       6696
Glu Gln Val Trp Lys Glu Met His Lys Leu Leu Pro Phe Ser Pro Asp
                180                 185                 190 tca gtc gtc act cat ggt gat ttc tca ctt gat aac ctt att ttt gac       6744
Ser Val Val Thr His Gly Asp Phe Ser Leu Asp Asn Leu Ile Phe Asp
            195                 200                 205 gag ggg aaa tta ata ggt tgt att gat gtt gga cga gtc gga atc gca       6792
Glu Gly Lys Leu Ile Gly Cys Ile Asp Val Gly Arg Val Gly Ile Ala
        210                 215                 220 gac cga tac cag gat ctt gcc atc cta tgg aac tgc ctc ggt gag ttt       6840
Asp Arg Tyr Gln Asp Leu Ala Ile Leu Trp Asn Cys Leu Gly Glu Phe
    225                 230                 235 tct cct tca tta cag aaa cgg ctt ttt caa aaa tat ggt att gat aat       6888
Ser Pro Ser Leu Gln Lys Arg Leu Phe Gln Lys Tyr Gly Ile Asp Asn
240                 245                 250                 255 cct gat atg aat aaa ttg cag ttt cat ttg atg ctc gat gag ttt ttc       6936
Pro Asp Met Asn Lys Leu Gln Phe His Leu Met Leu Asp Glu Phe Phe
                260                 265                 270 taa gaattactgt ctcatgagcg gatacatatt tgaatgtatt tagaaaata             6989
* aacaaaagag tttgtagaaa cgcaaaaagg ccatccgtca ggatggcctt ctgcttaatt     7049
tgatgcctgg cagtttatgg cgggcgtcct gcccgccacc ctccgggccg ttgcttcgca     7109
```

```
acgttcaaat ccgctcccgg cggatttgtc ctactcagga gagcgttcac cgacaaacaa      7169
cagataaaac gaaaggccca gtctttcgac tgagcctttc gttttatttg atgcctggca      7229
gttccctact ctcgcatggg gagacccac actaccatcg cgctacggc gtttcacttc        7289 tgagttcggc atggggtcag gtgggaccac cgcgctactg ccgccaggca aattctgttt      7349
tatcagaccg cttctgcgtt ctgatttaat ctgtatcagg ctgaaaatct tctctcatcc      7409
gccaaaacag ccaagcttgg ctcgacctag tcctggctga ttaaccagtc agacaacagc      7469
tcttgatact tggcattttc ctggacaaaa ggcatgtggc cgcagccggc aaagagctcc      7529
cagcgggcat ttggcaagtg atcgtacatg cttttagcca ctaggggagt gcacaagtcg      7589
tcagtgccgc tggtaatcaa ggccggcaag tccaggtcct ttaagcggtc agtgtactca      7649
tagccgtgca ggttgccaat cggcgtatat tcattagggc cccagcctgt caagtaggcc      7709
aggttgccgc cctttttttt gcgcaaaact ggctccggca ggtccggcgt aagcttgatg      7769
gcgtgctggt ccatgaagtg ggcattggcc gcctggtagg ccggggagtc gtagttgcca      7829
gttgtttcag cttccttgat agcggcctgc tcgcccttgg gcaggtactt gatcaagcgg      7889
tgcagttcct ggctccaaag cttggcggag gctaaagtgg aggagaggat caggctcttg      7949 accccttag gctggtagtc gcacaggtag atcaaagcca gcatcccgcc ccagctttgc        8009
cccaaaaggt ggatctggtc aaggcccagc tgctctctga cattttccag ctccttgacc      8069
caggtttggg ccgtgtaggc tgtttccgcc tggtcgtcgg ggatgctgga gttgccgcag      8129
cctaattggt catacatgat gacctggcgg ccgcttttt cagcgacttg gtcgaggact        8189
tcaaaatagt tgtgactgct gccgggcccg ccgtggagaa ggaggagcgg ggcgcggtca      8249
gtagcctcgc ccacgatccg gcagtaggtt tgccaatttc caaatggaag atatttttct      8309
gtgatttgca tcttgaatta attctgtttc ctgtgtgaaa ttgttatccg ctcacaattc      8369
cacacattat acgagccgat gattaattgt caacagctca tttcagaata tttgccagta      8429
a                                                                      8430
```

<210> SEQ ID NO 7
<211> LENGTH: 271
<212> TYPE: PRT
<213> ORGANISM: Homo sapiens

<400> SEQUENCE: 7

```
Met Ser His Ile Gln Arg Glu Thr Ser Cys Ser Arg Pro Arg Leu Asn
 1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125
```

| | | | | | | | | | | | |
|---|---|---|---|---|---|---|---|---|---|---|---|
|Arg|Arg|Leu|His|Ser|Ile|Pro|Val|Cys|Asn|Cys|Pro|Phe|Asn|Ser|Asp|
| |130| | | |135| | | |140| | |

Arg Val Phe Arg Leu Ala Gln Ala Gln Ser Arg Met Asn Asn Gly Leu
145             150                 155                 160

Val Asp Ala Ser Asp Phe Asp Asp Glu Arg Asn Gly Trp Pro Val Glu
            165                 170                 175

Gln Val Trp Lys Glu Met His Lys Leu Leu Pro Phe Ser Pro Asp Ser
        180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
            245                 250                 255

Asp Met Asn Lys Leu Gln Phe His Leu Met Leu Asp Glu Phe Phe
            260                 265                 270

<210> SEQ ID NO 8
<211> LENGTH: 6873
<212> TYPE: DNA
<213> ORGANISM: Homo sapiens
<220> FEATURE:
<221> NAME/KEY: CDS
<222> LOCATION: (5983)...(6865)
<223> OTHER INFORMATION: PEPI in reverse orientation
<221> NAME/KEY: misc_feature
<222> LOCATION: (5896)...(6062)
<223> OTHER INFORMATION: PTAC in reverse orientation
<221> NAME/KEY: misc_feature
<222> LOCATION: (1493)...(1529)
<223> OTHER INFORMATION: ORI in reverse orientation

<400> SEQUENCE: 8

```
aattcttaga aaaactcatc gagcatcaaa tgaaactgca atttattcat atcaggatta      60
tcaataccat attttgaaa  aagccgtttc tgtaatgaag gagaaaactc accgaggcag     120
ttccatagga tggcaagatc ctggtatcgg tctgcgattc cgactcgtcc aacatcaata    180
caacctatta atttcccctc gtcaaaaata aggttatcaa gtgagaaatc accatgagtg    240
acgactgaat ccggtgagaa tggcaaaagt ttatgcattt cttccagac  ttgttcaaca    300
ggccagccat tacgctcgtc atcaaaatca ctcgcatcaa ccaaaccgtt attcattcgt    360
gattgcgcct gagcgagacg aaatacgcga tcgctgttaa aaggacaatt acaaacagga    420
atcgaatgca accggcgcag gaacactgcc agcgcatcaa caatattttc acctgaatca    480
ggatattctt ctaatacctg gaatgctgtt ttcccgggga tcgcagtggt gagtaaccat    540
gcatcatcag gagtacggat aaaatgcttg atggtcggaa gaggcataaa ttccgtcagc    600
cagtttagtc tgaccatctc atctgtaaca tcattggcaa cgctacctt  gccatgtttc    660
agaaacaact ctggcgcatc gggcttccca tacaatcgat agattgtcgc acctgattgc    720
ccgacattat cgcgagccca tttataccca tataaatcag catccatgtt ggaatttaat    780
cgcggcctag agcaagacgt ttcccgttga atatggctca taacacccct tgtattactg    840
tttatgtaag cagacagttt tattgttcat gaccaaaatc ccttaacgtg agttttcgtt    900
ccactgagcg tcagaccccg tagaaaagat caaaggatct tcttgagatc ctttttttct    960
gcgcgtaatc tgctgcttgc aaacaaaaaa accaccgcta ccagcggtgg tttgtttgcc   1020
```

-continued

```
ggatcaagag ctaccaactc tttttccgaa ggtaactggc ttcagcagag cgcagatacc      1080
aaatactgtc cttctagtgt agccgtagtt aggccaccac ttcaagaact ctgtagcacc      1140
gcctacatac ctcgctctgc taatcctgtt accagtggct gctgccagtg gcgataagtc      1200
gtgtcttacc gggttggact caagacgata gttaccggat aaggcgcagc ggtcgggctg      1260 aacgggggt tcgtgcacac agcccagctt ggagcgaacg acctacaccg aactgagata       1320
cctacagcgt gagctatgag aaagcgccac gcttcccgaa gggagaaagg cggacaggta      1380
tccggtaagc ggcagggtcg gaacaggaga gcgcacgagg gagcttccag ggggaaacgc      1440
ctggtatctt tatagtcctg tcgggtttcg ccacctctga cttgagcgtc gattttgtg       1500 atgctcgtca gggggcgga gcctatggaa aaacgccagc aacgcggcct ttttacggtt       1560
cctggccttt tgctggcctt ttgctcacat gttctttcct gcgttatccc ctgattctgt      1620
ggataaccgt attaccgcct ttgagtgagc tgataccgct cgccgcagcc gaacgaccga      1680
gcgcagcgag tcagtgagcg aggaagcgga agagcgcctg atgcggtatt ttctccttac      1740
gcatctgtgc ggtatttcac accgcatata tggtgcactc tcagtacaat ctgctctgat      1800
gccgcatagt taagccagta agctttaatg cggtagttta tcacagttaa attgctaacg      1860
cagtcaggca ccgtgtatga aatctaacaa tgcgctcatc gtcatcctcg gcaccgtcac      1920
cctggatgct gtaggcatag gcttggttat gccggtactg ccgggcctct tgcgggatat      1980
ccggatatag ttcctccttt cagcaaaaaa cccctcaaga cccgtttaga ggccccaagg      2040
ggttatgcta gttattgctc agcggtgca gcagccaact cagcttcctt tccgggctttg      2100 ttagcagccg gatccgtcga cgctagctta ctgctgagcg ccagcggcag ctggaacagg      2160
catcccaagg gggttggcag cagcaatcac tggtgagcct gccagaggtc caaggggtga      2220 agggggttggc actgaagaaa tccctgacat catattggcg ctgctgacgg gcgtactgcc      2280
ccctggcatg ctagatgaac ccattcgagc ctggtccttc acaacagtgt agaaataggg      2340
gtgctccatt gcctctcttg cagtaagccg tgactggtgg tcatatcgca gcagtttgtc      2400
caggaaatcc aaggcctcag ggctgacaag gtgctgattt tcactgtgga caaagcgttc      2460
ccatcgcttt cgagagtgtc tgcccaagat atcattgaaa cgtggatcta attcaatgtt      2520
gtatttgtca atatagtcat ataaatcttc tgtccccaga accttggcta tcctcaccaa      2580
ctgatcataa ttgtcatgtc catggaaaaa tggctccttc cgaaagatca tacttgccag      2640
catacaaccc aaactccaca tatccaaact ataatcgtac atctgatagt ctacaagtag      2700
ctcaggacct ttgaagtatc gggaagcaac tcggacatta tattcttggc caggatgata      2760
aaactcagca aaaccccagt ctattagtcg tagcttttctg tgctcatgat caatcatgac      2820
attatggggc ttgacatctc tgtgcataat tcccatgctg tgacaataat ccagggcctt      2880
cagaatctca tacatgtaaa atcgaatatc atagtctgtt aacgtctggt acaattgctt      2940
gaagtctgtg ttgtttacgt gttcaaaaac caaggcgggg gttcgtgaca cagggtcttt      3000
tacaatgtct gccagtgtga tgatgttggg acctcctctc aaattctcca aaatctttat      3060
ttcacgctta attttcttct tttttactgg cttgagaatt ttaacaacaa cttttttcatt     3120 atttgtgatg ttgatggctt caaatacttc actgtattta cctcggccta attttcgaac      3180
cagctggtag tcatcttgat ttccccattc caccacatgt gactcgtaat cccagtattc      3240
tcgaggtctg tgtgtattaa catctgtgta aactctggcc ctgcttggca cgggtcccga      3300
catatgtata tctccttctt gtcgacttag cgaatcgtct tgactgggct cttgaagttg      3360
ctggcggctt ggagctgcag ctggtaggcc atcgcatgga tcttgaaacc gtagagcctg      3420
```

```
ggcacaaact ggttggcagg tctcttgggc cggtactcgg gatgcaccat gaagagcatg    3480
tgagggaaac cagtgccgaa gtaggcgcca tccgtgtgat ggtgtcttga tgacttgggt    3540
gtgtacacat ccatgcactt ggggcagtag agcttcacca tggcttcacc tgggatgtct    3600
gaaaggccaa tgggaagcat tggctggttc tcacagtaca cacgaggaca gtaaccaaag    3660
tctccttgct ggtactttc caacatctgg gcgatgccac ggttggtaag gatgtagcgg    3720
gcgtggatca atccataaag catctcggct gcctgctcaa tcaggtcact ctggttgggg    3780
ttgtcttcca gttcttcatc aggctccagg tccaagatca tgtctagagc ttgtcggtag    3840
tgagggacct gctcattgag tccagtaaga ttaaatttgt cctggatgta gtcttcatcc    3900
acttcacaga agaattcatt gccacggagc ccacagaacc aggaaatcca ggacacctcc    3960
tctgagctgc tcatatgtta ttcctcctta tttaatcgat ccggatatag ttcctccttt    4020
cagcaaaaaa cccctcaaga cccgtttaga ggccccaagg ggttatgcta gttattgctc    4080
agcggtggca gcagccaact cagcttcctt tcgggctttg ttagcagccg gatccttatt    4140
agacactaat ggggttatga actggggcaa gtggctgagt cacagggtag atctggtggg    4200
tggggttaag tagaagttct tggttgagca gaagggcttg aacaggcaca gctctctgag    4260
ggtagggcac cacttgctgg gggataggca ggactttggg ctgaggaaca gaccacaggg    4320
gctgaggggg aagtgcaaga gtctgaggaa taggctgagg gacctgctgc atcaagggct    4380
ggagcagagg cagaggaaga tgcagatttt caagatcagt gagttttggg atttgagggt    4440
caaaaaaggg tatcgttgga gatttaagga caggcatcac tctgcccta gtgtagacag    4500 tgtctttagc tttagggact tccattattt caggctgagg gacaggcagc accacagcag    4560
gctgagcaag aggcagaatg ttttgtggaa gaaaaccata ggggataggt tcaacgaatg    4620
gatagatcag aggctgtggc tggaaagagg ggtagatttt atcctggtgt tcatcctctc    4680
cttgctgctg gtcctcgtgt ttaacttttt caactttctg tttgtattcg gtgatcgatt    4740
cttcgctcga gctcagggat tcgatggttt cacgcggcat atgtatatct ccttcttaaa    4800
gttaaacaaa attatttcta gagggaaacc gttgtggtct ccctatagtg agtcgtatta    4860
atttcgcggg atcgagatct cgatcctcta cgccggacgc atcgtggccg gcatcaccgg    4920
cgccacaggt gcggttgctg gcgcctatat cgccgacatc accgatgggg aagatcgggc    4980
tcgccacttc gggctcatga gcgcttgttt cggcgtgggt atggtggcag gccccgtggc    5040
cgggggactg ttgggcgcca tctccttgca tgcaccattc cttgcggcgg cggtgctcaa    5100
cggcctcaac ctactactgg gctgcttcct aatgcaggag tcgcataagg gagagcgtcg    5160
accgatgccc ttgagagcct tcaacccagt cagctccttc cggtgggcgc ggggcatgac    5220
tatcgtcgcc gcacttatga ctgtcttctt tatcatgcaa ctcgtaggac aggtgccggc    5280
agcgctctgg gtcattttcg gcgaggaccg ctttcgctgg agcgcgacga tgatcggcct    5340
gtcgcttgcg gtattcggaa tcttgcacgc cctcgctcaa gccttcgtca ctggtcccgc    5400
caccaaacgt ttcggcgaga agcaggccat tatcgccggc atggcggccg acgcgctggg    5460
ctacgtcttg ctggcgttcg tacactccgc tatcgctacg tgactgggtc atggctgcgc    5520
cccgacaccc gccaacaccc gctgacgcgc cctgacgggc ttgtctgctc ccggcatccg    5580
cttacagaca agctgtgacc gtctccggga gctgcatgtg tcagaggttt tcaccgtcat    5640
caccgaaacg cgcgaggcag ctgcggtaaa gctcatcagc gtggtcgtga agcgattcca    5700
attgatccgg gcttatcgac tgcacggtgc accaatgctt ctggcgtcag gcagccatcg    5760
gaagctgtgg tatggctgtg caggtcgtaa atcactgcat aattcgtgtc gctcaaggcg    5820
```

```
cactcccgtt ctggataatg ttttttgcgc cgacatcata acggttctgg caaatattct    5880
gaaatgagct gttgacaatt aatcatcggc tcgtataatg tgtggaattg tgagcggata    5940
acaatttcac acaggaaaca gaattcccgg ggatcaattc aag atg caa atc aca     5995
                                              Met Gln Ile Thr
                                                1 gaa aaa tat ctt cca ttt gga aat tgg caa acc tac tgc cgg atc gtg     6043
Glu Lys Tyr Leu Pro Phe Gly Asn Trp Gln Thr Tyr Cys Arg Ile Val
  5              10                  15                  20 ggc gag gct act gac cgc gcc ccg ctc ctc ctt ctc cac ggc ggg ccc     6091
Gly Glu Ala Thr Asp Arg Ala Pro Leu Leu Leu Leu His Gly Gly Pro
                 25                  30                  35 ggc agc agt cac aac tat ttt gaa gtc ctc gac caa gtc gct gaa aaa     6139
Gly Ser Ser His Asn Tyr Phe Glu Val Leu Asp Gln Val Ala Glu Lys
             40                  45                  50 agc ggc cgc cag gtc atc atg tat gac caa tta ggc tgc ggc aac tcc     6187
Ser Gly Arg Gln Val Ile Met Tyr Asp Gln Leu Gly Cys Gly Asn Ser
         55                  60                  65 agc atc ccc gac gac cag gcg gaa aca gcc tac acg gcc caa acc tgg     6235
Ser Ile Pro Asp Asp Gln Ala Glu Thr Ala Tyr Thr Ala Gln Thr Trp
     70                  75                  80 gtc aag gag ctg gaa aat gtc aga gag cag ctg ggc ctt gac cag atc     6283
Val Lys Glu Leu Glu Asn Val Arg Glu Gln Leu Gly Leu Asp Gln Ile
 85                  90                  95                 100 cac ctt ttg ggg caa agc tgg ggc ggg atg ctg gct ttg atc tac ctg     6331
His Leu Leu Gly Gln Ser Trp Gly Gly Met Leu Ala Leu Ile Tyr Leu
                105                 110                 115 tgc gac tac cag cct aaa ggg gtc aag agc ctg atc ctc tcc tcc act     6379
Cys Asp Tyr Gln Pro Lys Gly Val Lys Ser Leu Ile Leu Ser Ser Thr
            120                 125                 130 tta gcc tcc gcc aag ctt tgg agc cag gaa ctg cac cgc ttg atc aag     6427
Leu Ala Ser Ala Lys Leu Trp Ser Gln Glu Leu His Arg Leu Ile Lys
        135                 140                 145 tac ctg ccc aag ggc gag cag gcc gct atc aag gaa gct gaa aca act     6475
Tyr Leu Pro Lys Gly Glu Gln Ala Ala Ile Lys Glu Ala Glu Thr Thr
    150                 155                 160 ggc aac tac gac tcc ccg gcc tac cag gcg gcc aat gcc cac ttc atg     6523
Gly Asn Tyr Asp Ser Pro Ala Tyr Gln Ala Ala Asn Ala His Phe Met
165                 170                 175                 180 gac cag cac gcc atc aag ctt acg ccg gac ctg ccg gag cca gtt ttg     6571
Asp Gln His Ala Ile Lys Leu Thr Pro Asp Leu Pro Glu Pro Val Leu
                185                 190                 195 cgc aaa aaa aag ggc ggc aac ctg gcc tac ttg aca ggc tgg ggc cct     6619
Arg Lys Lys Lys Gly Gly Asn Leu Ala Tyr Leu Thr Gly Trp Gly Pro
            200                 205                 210 aat gaa tat acg ccg att ggc aac ctg cac ggc tat gag tac act gac     6667
Asn Glu Tyr Thr Pro Ile Gly Asn Leu His Gly Tyr Glu Tyr Thr Asp
        215                 220                 225 cgc tta aag gac ctg gac ttg ccg gcc ttg att acc agc ggc act gac     6715
Arg Leu Lys Asp Leu Asp Leu Pro Ala Leu Ile Thr Ser Gly Thr Asp
    230                 235                 240 gac ttg tgc act ccc cta gtg gct aaa agc atg tac gat cac ttg cca     6763
Asp Leu Cys Thr Pro Leu Val Ala Lys Ser Met Tyr Asp His Leu Pro
245                 250                 255                 260 aat gcc cgc tgg gag ctc ttt gcc ggc tgc ggc cac atg cct ttt gtc     6811
Asn Ala Arg Trp Glu Leu Phe Ala Gly Cys Gly His Met Pro Phe Val
                265                 270                 275 cag gaa aat gcc aag tat caa gag ctg ttg tct gac tgg tta atc agc     6859
Gln Glu Asn Ala Lys Tyr Gln Glu Leu Leu Ser Asp Trp Leu Ile Ser
            280                 285                 290
```

```
cag gac tag gtcga                                                                  6873
Gln Asp  *
```

<210> SEQ ID NO 9
<211> LENGTH: 294
<212> TYPE: PRT
<213> ORGANISM: Homo sapiens

<400> SEQUENCE: 9

```
Met Gln Ile Thr Glu Lys Tyr Leu Pro Phe Gly Asn Trp Gln Thr Tyr
 1               5                  10                  15

Cys Arg Ile Val Gly Glu Ala Thr Asp Arg Ala Pro Leu Leu Leu Leu
                20                  25                  30

His Gly Gly Pro Gly Ser Ser His Asn Tyr Phe Glu Val Leu Asp Gln
            35                  40                  45

Val Ala Glu Lys Ser Gly Arg Gln Val Ile Met Tyr Asp Gln Leu Gly
        50                  55                  60

Cys Gly Asn Ser Ser Ile Pro Asp Asp Gln Ala Glu Thr Ala Tyr Thr
65                  70                  75                  80

Ala Gln Thr Trp Val Lys Glu Leu Glu Asn Val Arg Glu Gln Leu Gly
                85                  90                  95

Leu Asp Gln Ile His Leu Leu Gly Gln Ser Trp Gly Gly Met Leu Ala
                100                 105                 110

Leu Ile Tyr Leu Cys Asp Tyr Gln Pro Lys Gly Val Lys Ser Leu Ile
            115                 120                 125

Leu Ser Ser Thr Leu Ala Ser Ala Lys Leu Trp Ser Gln Glu Leu His
        130                 135                 140

Arg Leu Ile Lys Tyr Leu Pro Lys Gly Glu Gln Ala Ala Ile Lys Glu
145                 150                 155                 160

Ala Glu Thr Thr Gly Asn Tyr Asp Ser Pro Ala Tyr Gln Ala Ala Asn
                165                 170                 175

Ala His Phe Met Asp Gln His Ala Ile Lys Leu Thr Pro Asp Leu Pro
                180                 185                 190

Glu Pro Val Leu Arg Lys Lys Gly Gly Asn Leu Ala Tyr Leu Thr
            195                 200                 205

Gly Trp Gly Pro Asn Glu Tyr Thr Pro Ile Gly Asn Leu His Gly Tyr
        210                 215                 220

Glu Tyr Thr Asp Arg Leu Lys Asp Leu Asp Leu Pro Ala Leu Ile Thr
225                 230                 235                 240

Ser Gly Thr Asp Asp Leu Cys Thr Pro Leu Val Ala Lys Ser Met Tyr
                245                 250                 255

Asp His Leu Pro Asn Ala Arg Trp Glu Leu Phe Ala Gly Cys Gly His
                260                 265                 270

Met Pro Phe Val Gln Glu Asn Ala Lys Tyr Gln Glu Leu Leu Ser Asp
            275                 280                 285

Trp Leu Ile Ser Gln Asp
        290
```

<210> SEQ ID NO 10
<211> LENGTH: 8430
<212> TYPE: DNA
<213> ORGANISM: Homo sapiens
<220> FEATURE:
<221> NAME/KEY: CDS
<222> LOCATION: (111)...(995)
<223> OTHER INFORMATION: Pepi in reverse orientation
<221> NAME/KEY: CDS
<222> LOCATION: (5279)...(5920)

```
<223> OTHER INFORMATION: HBCN in reverse orientation
<221> NAME/KEY: CDS
<222> LOCATION: (6085)...(6732)
<223> OTHER INFORMATION: CKIIb in reverse orientation
<221> NAME/KEY: CDS
<222> LOCATION: (6756)...(7931)
<223> OTHER INFORMATION: CKIIa in reverse orientation
<221> NAME/KEY: misc_feature
<222> LOCATION: (3)...(100)
<223> OTHER INFORMATION: PTAC in reverse orientation
<221> NAME/KEY: misc_feature
<222> LOCATION: (1000)...(1485)
<223> OTHER INFORMATION: RRNBT1T2Term in reverse orientation
<221> NAME/KEY: misc_feature
<222> LOCATION: (2979)...(3015)
<223> OTHER INFORMATION: ORI in reverse orientation
<221> NAME/KEY: misc_feature
<222> LOCATION: (5198)...(5214)
<223> OTHER INFORMATION: T7 Promoter in reverse orientation
<221> NAME/KEY: misc_feature
<222> LOCATION: (5988)...(6034)
<223> OTHER INFORMATION: T7 Terminator in reverse orientation
<221> NAME/KEY: misc_feature
<222> LOCATION: (1008)...(1053)
<223> OTHER INFORMATION: T7 Terminator in reverse orientation

<400> SEQUENCE: 10
ttactggcaa atattctgaa atgagctgtt gacaattaat catcggctcg tataatgtgt      60
ggaattgtga gcggataaca atttcacaca ggaaacagaa ttaattcaag atg caa     116
                                                        Met Gln
                                                        1 atc aca gaa aaa tat ctt cca ttt gga aat tgg caa acc tac tgc cgg    164
Ile Thr Glu Lys Tyr Leu Pro Phe Gly Asn Trp Gln Thr Tyr Cys Arg
    5                  10                 15 atc gtg ggc gag gct act gac cgc gcc ccg ctc ctc ctt ctc cac ggc    212
Ile Val Gly Glu Ala Thr Asp Arg Ala Pro Leu Leu Leu Leu His Gly
 20                 25                  30 ggg ccc ggc agc agt cac aac tat ttt gaa gtc ctc gac caa gtc gct    260
Gly Pro Gly Ser Ser His Asn Tyr Phe Glu Val Leu Asp Gln Val Ala
 35                 40                  45                 50 gaa aaa agc ggc cgc cag gtc atc atg tat gac caa tta ggc tgc ggc    308
Glu Lys Ser Gly Arg Gln Val Ile Met Tyr Asp Gln Leu Gly Cys Gly
                 55                  60                 65 aac tcc agc atc ccc gac gac cag gcg gaa aca gcc tac acg gcc caa    356
Asn Ser Ser Ile Pro Asp Asp Gln Ala Glu Thr Ala Tyr Thr Ala Gln
                 70                  75                 80 acc tgg gtc aag gag ctg gaa aat gtc aga gag cag ctg ggc ctt gac    404
Thr Trp Val Lys Glu Leu Glu Asn Val Arg Glu Gln Leu Gly Leu Asp
             85                  90                  95 cag atc cac ctt ttg ggg caa agc tgg ggc ggg atg ctg gct ttg atc    452
Gln Ile His Leu Leu Gly Gln Ser Trp Gly Gly Met Leu Ala Leu Ile
100                 105                 110 tac ctg tgc gac tac cag cct aaa ggg gtc aag agc ctg atc ctc tcc    500
Tyr Leu Cys Asp Tyr Gln Pro Lys Gly Val Lys Ser Leu Ile Leu Ser
115                 120                 125                 130 tcc act tta gcc tcc gcc aag ctt tgg agc cag gaa ctg cac cgc ttg    548
Ser Thr Leu Ala Ser Ala Lys Leu Trp Ser Gln Glu Leu His Arg Leu
                135                 140                 145 atc aag tac ctg ccc aag ggc gag cag gcc gct atc aag gaa gct gaa    596
Ile Lys Tyr Leu Pro Lys Gly Glu Gln Ala Ala Ile Lys Glu Ala Glu
                150                 155                 160 aca act ggc aac tac gac tcc ccg gcc tac cag gcg gcc aat gcc cac    644
Thr Thr Gly Asn Tyr Asp Ser Pro Ala Tyr Gln Ala Ala Asn Ala His
165                 170                 175
```

```
ttc atg gac cag cac gcc atc aag ctt acg ccg gac ctg ccg gag cca        692
Phe Met Asp Gln His Ala Ile Lys Leu Thr Pro Asp Leu Pro Glu Pro
    180                 185                 190 gtt ttg cgc aaa aaa aag ggc ggc aac ctg gcc tac ttg aca ggc tgg        740
Val Leu Arg Lys Lys Lys Gly Gly Asn Leu Ala Tyr Leu Thr Gly Trp
195                 200                 205                 210 ggc cct aat gaa tat acg ccg att ggc aac ctg cac ggc tat gag tac        788
Gly Pro Asn Glu Tyr Thr Pro Ile Gly Asn Leu His Gly Tyr Glu Tyr
            215                 220                 225 act gac cgc tta aag gac ctg gac ttg ccg gcc ttg att acc agc ggc        836
Thr Asp Arg Leu Lys Asp Leu Asp Leu Pro Ala Leu Ile Thr Ser Gly
        230                 235                 240 act gac gac ttg tgc act ccc cta gtg gct aaa agc atg tac gat cac        884
Thr Asp Asp Leu Cys Thr Pro Leu Val Ala Lys Ser Met Tyr Asp His
    245                 250                 255 ttg cca aat gcc cgc tgg gag ctc ttt gcc ggc tgc ggc cac atg cct        932
Leu Pro Asn Ala Arg Trp Glu Leu Phe Ala Gly Cys Gly His Met Pro
260                 265                 270 ttt gtc cag gaa aat gcc aag tat caa gag ctg ttg tct gac tgg tta        980
Phe Val Gln Glu Asn Ala Lys Tyr Gln Glu Leu Leu Ser Asp Trp Leu
275                 280                 285                 290 atc agc cag gac tag gtcgagccaa gcttggctgt tttggcggat gagagaagat       1035
Ile Ser Gln Asp * tttcagcctg atacagatta aatcagaacg cagaagcggt ctgataaaac agaatttgcc    1095
tggcggcagt agcgcggtgg tcccacctga ccccatgccg aactcagaag tgaaacgccg    1155
tagcgccgat ggtagtgtgg ggtctcccca tgcgagagta gggaactgcc aggcatcaaa    1215
taaaacgaaa ggctcagtcg aaagactggg cctttcgttt tatctgttgt ttgtcggtga    1275
acgctctcct gagtaggaca atccgccgg gagcggattt gaacgttgcg aagcaacggc     1335
ccggagggtg gcgggcagga cgcccgccat aaactgccag gcatcaaatt aagcagaagg    1395
ccatcctgac ggatggcctt tttgcgtttc tacaaactct tttgtttatt tttctaaata    1455
cattcaaata tgtatccgct catgagacag taattcttag aaaaactcat cgagcatcaa    1515
atgaaactgc aatttattca tatcaggatt atcaatacca tatttttgaa aaagccgttt    1575
ctgtaatgaa ggagaaaact caccgaggca gttccatagg atggcaagat cctggtatcg    1635
gtctgcgatt ccgactcgtc caacatcaat acaacctatt aatttcccct cgtcaaaaat    1695
aaggttatca agtgagaaat caccatgagt gacgactgaa tccggtgaga atggcaaaag    1755
cttatgcatt tctttccaga cttgttcaac aggccagcca ttacgctcgt catcaaaatc    1815
actcgcatca accaaaccgt tattcattcg tgattgcgcc tgagcgagac gaaatacgcg    1875
atcgctgtta aaaggacaat tacaaacagg aatcgaatgc aaccggcgca ggaacactgc    1935
cagcgcatca acaatatttt cacctgaatc aggatattct tctaatacct ggaatgctgt    1995
tttcccgggg atcgcagtgg tgagtaacca tgcatcatca ggagtacgga taaaatgctt    2055
gatggtcgga agaggcataa attccgtcag ccagtttagt ctgaccatct catctgtaac    2115
atcattggca acgctacctt tgccatgttt cagaaacaac tctggcgcat cgggcttccc    2175
atacaatcga tagattgtcg cacctgattg cccgacatta tcgcgagccc atttataccc    2235
atataaatca gcatccatgt tggaatttaa tcgcggcctc gagcaagacg tttcccgttg    2295
aatatggctc ataacacccc ttgtattact gtttatgtaa gcagacagtt ttattgttca    2355
tgaccaaaat cccttaacgt gagttttcgt tccactgagc gtcagacccc gtagaaaaga    2415
tcaaaggatc ttcttgagat cctttttttc tgcgcgtaat ctgctgcttg caaacaaaaa    2475
```

-continued

| | | | | | |
|---|---|---|---|---|---|
| aaccaccgct | accagcggtg | gtttgtttgc | cggatcaaga | gctaccaact | ctttttccga | 2535 |
| aggtaactgg | cttcagcaga | gcgcagatac | caaatactgt | ccttctagtg | tagccgtagt | 2595 |
| taggccacca | cttcaagaac | tctgtagcac | cgcctacata | cctcgctctg | ctaatcctgt | 2655 |
| taccagtggc | tgctgccagt | ggcgataagt | cgtgtcttac | cgggttggac | tcaagacgat | 2715 |
| agttaccgga | taaggcgcag | cggtcgggct | gaacgggggg | ttcgtgcaca | cagcccagct | 2775 |
| tggagcgaac | gacctacacc | gaactgagat | acctacagcg | tgagctatga | gaaagcgcca | 2835 |
| cgcttcccga | agggagaaag | gcggacaggt | atccggtaag | cggcagggtc | ggaacaggag | 2895 |
| agcgcacgag | ggagcttcca | gggggaaacg | cctggtatct | ttatagtcct | gtcgggtttc | 2955 |
| gccacctctg | acttgagcgt | cgattttgt | gatgctcgtc | aggggggcgg | agcctatgga | 3015 |
| aaaacgccag | caacgcggcc | tttttacggt | tcctggcctt | ttgctggcct | tttgctcaca | 3075 |
| tgttctttcc | tgcgttatcc | cctgattctg | tggataaccg | tattaccgcc | tttgagtgag | 3135 |
| ctgataccgc | tcgccgcagc | cgaacgaccg | agcgcagcga | gtcagtgagc | gaggaagcgg | 3195 |
| aagagcgcct | gatgcggtat | tttctcctta | cgcatctgtg | cggtatttca | caccgcatat | 3255 |
| atggtgcact | ctcagtacaa | tctgctctga | tgccgcatag | ttaagccagt | atacactccg | 3315 |
| ctatcgctac | gtgactgggt | catggctgcg | ccccgacacc | cgccaacacc | cgctgacgcg | 3375 |
| ccctgacggg | cttgtctgct | cccggcatcc | gcttacagac | aagctgtgac | cgtctccggg | 3435 |
| agctgcatgt | gtcagaggtt | ttcaccgtca | tcaccgaaac | gcgcgaggca | gctgcggtaa | 3495 |
| agctcatcag | cgtggtcgtg | aagcgattca | cagatgtctg | cctgttcatc | cgcgtccagc | 3555 |
| tcgttgagtt | tctccagaag | cgttaatgtc | tggcttctga | taaagcgggc | catgttaagg | 3615 |
| gcggtttttt | cctgtttggt | cactgatgcc | tccgtgtaag | ggggatttct | gttcatgggg | 3675 |
| gtaatgatac | cgatgaaacg | agagaggatg | ctcacgatac | gggttactga | tgatgaacat | 3735 |
| gcccggttac | tggaacgttg | tgagggtaaa | caactggcgg | tatggatgcg | gcgggaccag | 3795 |
| agaaaaatca | ctcagggtca | atgccagcgc | ttcgttaata | cagatgtagg | tgttccacag | 3855 |
| ggtagccagc | agcatcctgc | gatgcagatc | cggaacataa | tggtgcaggg | cgctgacttc | 3915 |
| cgcgtttcca | gactttacga | aacacggaaa | ccgaagacca | ttcatgttgt | tgctcaggtc | 3975 |
| gcagacgttt | tgcagcagca | gtcgcttcac | gttcgctcgc | gtatcggtga | ttcattctgc | 4035 |
| taaccagtaa | ggcaaccccg | ccagcctagc | cgggtcctca | acgacaggag | cacgatcatg | 4095 |
| cgcacccgtg | gccaggaccc | aacgctgccc | gagatgcgcc | gcgtgcggct | gctggagatg | 4155 |
| gcggacgcga | tggatatgtt | ctgccaaggg | ttggtttgcg | cattcacagt | tctccgcaag | 4215 |
| aattgattgg | ctccaattct | tggagtggtg | aatccgttag | cgaggtgccg | ccggcttcca | 4275 |
| ttcaggtcga | ggtggcccgg | ctccatgcac | cgcgacgcaa | cgcggggagg | cagacaaggt | 4335 |
| atagggcggc | gcctacaatc | catgccaacc | cgttccatgt | gctcgccgag | gcggcataaa | 4395 |
| tcgccgtgac | gatcagcggt | ccagtgatcg | aagttaggct | ggtaagagcc | gcgagcgatc | 4455 |
| cttgaagctg | tccctgatgg | tcgtcatcta | cctgcctgga | cagcatggcc | tgcaacgcgg | 4515 |
| gcatcccgat | gccgccggaa | gcgagaagaa | tcataatggg | gaaggccatc | cagcctcgcg | 4575 |
| tcgcgaacgc | cagcaagacg | tagcccagcg | cgtcggccgc | catgccggcg | ataatggcct | 4635 |
| gcttctcgcc | gaaacgtttg | gtggcgggac | cagtgacgaa | ggcttgagcg | agggcgtgca | 4695 |
| agattccgaa | taccgcaagc | gacaggccga | tcatcgtcgc | gctccagcga | aagcggtcct | 4755 |
| cgccgaaaat | gacccagagc | gctgccggca | cctgtcctac | gagttgcatg | ataaagaaga | 4815 |
| cagtcataag | tgcggcgacg | atagtcatgc | cccgcgccca | ccggaaggag | ctgactgggt | 4875 |

```
                                                       -continued tgaaggctct caagggcatc ggtcgacgct ctcccttatg cgactcctgc attaggaagc     4935
agcccagtag taggttgagg ccgttgagca ccgccgccgc aaggaatggt gcatgcaagg     4995
agatggcgcc caacagtccc ccggccacgg ggcctgccac catacccacg ccgaaacaag     5055
cgctcatgag cccgaagtgg cgagcccgat cttccccatc ggtgatgtcg gcgatatagg     5115
cgccagcaac cgcacctgtg gcgccggtga tgccggccac gatgcgtccg gcgtagagga     5175
tcgagatctc gatcccgcga attaatacg actcactata gggagaccac aacggtttcc      5235
ctctagaaat aattttgttt aactttaaga aggagatata cat atg cca cgt gaa       5290
                                                Met Pro Arg Glu
                                                         295 acc atc gaa tcc ctg agc tcg agc gaa gaa tcg atc acc gaa tac aaa       5338
Thr Ile Glu Ser Leu Ser Ser Ser Glu Glu Ser Ile Thr Glu Tyr Lys
        300             305                 310 cag aaa gtt gaa aaa gtt aaa cac gag gac cag cag caa gga gag gat       5386
Gln Lys Val Glu Lys Val Lys His Glu Asp Gln Gln Gln Gly Glu Asp
315             320                 325                 330 gaa cac cag gat aaa atc tac ccc tct ttc cag cca cag cct ctg atc       5434
Glu His Gln Asp Lys Ile Tyr Pro Ser Phe Gln Pro Gln Pro Leu Ile
                335                 340                 345 tat cca ttc gtt gaa cct atc ccc tat ggt ttt ctt cca caa aac att       5482
Tyr Pro Phe Val Glu Pro Ile Pro Tyr Gly Phe Leu Pro Gln Asn Ile
            350                 355                 360 ctg cct ctt gct cag cct gct gtg gtg ctg cct gtc cct cag cct gaa       5530
Leu Pro Leu Ala Gln Pro Ala Val Val Leu Pro Val Pro Gln Pro Glu
        365                 370                 375 ata atg gaa gtc cct aaa gct aaa gac act gtc tac act aag ggc aga       5578
Ile Met Glu Val Pro Lys Ala Lys Asp Thr Val Tyr Thr Lys Gly Arg
380             385                 390 gtg atg cct gtc ctt aaa tct cca acg ata ccc ttt ttt gac cct caa       5626
Val Met Pro Val Leu Lys Ser Pro Thr Ile Pro Phe Phe Asp Pro Gln
395             400                 405                 410 atc cca aaa ctc act gat ctt gaa aat ctg cat ctt cct ctg cct ctg       5674
Ile Pro Lys Leu Thr Asp Leu Glu Asn Leu His Leu Pro Leu Pro Leu
                415                 420                 425 ctc cag ccc ttg atg cag cag gtc cct cag cct att cct cag act ctt       5722
Leu Gln Pro Leu Met Gln Gln Val Pro Gln Pro Ile Pro Gln Thr Leu
            430                 435                 440 gca ctt ccc cct cag ccc ctg tgg tct gtt cct cag ccc aaa gtc ctg       5770
Ala Leu Pro Pro Gln Pro Leu Trp Ser Val Pro Gln Pro Lys Val Leu
        445                 450                 455 cct atc ccc cag caa gtg gtg ccc tac cct cag aga gct gtg cct gtt       5818
Pro Ile Pro Gln Gln Val Val Pro Tyr Pro Gln Arg Ala Val Pro Val
460             465                 470 caa gcc ctt ctg ctc aac caa gaa ctt cta ctt aac ccc acc cac cag       5866
Gln Ala Leu Leu Leu Asn Gln Glu Leu Leu Leu Asn Pro Thr His Gln
475             480                 485                 490 atc tac cct gtg act cag cca ctt gcc cca gtt cat aac ccc att agt       5914
Ile Tyr Pro Val Thr Gln Pro Leu Ala Pro Val His Asn Pro Ile Ser
                495                 500                 505 gtc taa taaggatccg gctgctaaca aagcccgaaa ggaagctgag ttggctgctg       5970
Val * ccaccgctga gcaataacta gcataacccc ttggggcctc taaacgggtc ttgaggggtt    6030
ttttgctgaa aggaggaact atatccggat cgattaaata aggaggaata acat atg      6087
                                                              Met agc agc tca gag gag gtg tcc tgg att tcc tgg ttc tgt ggg ctc cgt      6135
Ser Ser Ser Glu Glu Val Ser Trp Ile Ser Trp Phe Cys Gly Leu Arg
        510                 515                 520
```

-continued

```
ggc aat gaa ttc ttc tgt gaa gtg gat gaa gac tac atc cag gac aaa    6183
Gly Asn Glu Phe Phe Cys Glu Val Asp Glu Asp Tyr Ile Gln Asp Lys
525                 530                 535                 540 ttt aat ctt act gga ctc aat gag cag gtc cct cac tac cga caa gct    6231
Phe Asn Leu Thr Gly Leu Asn Glu Gln Val Pro His Tyr Arg Gln Ala
            545                 550                 555 cta gac atg atc ttg gac ctg gag cct gat gaa gaa ctg gaa gac aac    6279
Leu Asp Met Ile Leu Asp Leu Glu Pro Asp Glu Glu Leu Glu Asp Asn
        560                 565                 570 ccc aac cag agt gac ctg att gag cag gca gcc gag atg ctt tat gga    6327
Pro Asn Gln Ser Asp Leu Ile Glu Gln Ala Ala Glu Met Leu Tyr Gly
    575                 580                 585 ttg atc cac gcc cgc tac atc ctt acc aac cgt ggc atc gcc cag atg    6375
Leu Ile His Ala Arg Tyr Ile Leu Thr Asn Arg Gly Ile Ala Gln Met
590                 595                 600 ttg gaa aag tac cag caa gga gac ttt ggt tac tgt cct cgt gtg tac    6423
Leu Glu Lys Tyr Gln Gln Gly Asp Phe Gly Tyr Cys Pro Arg Val Tyr
605                 610                 615                 620 tgt gag aac cag cca atg ctt ccc att ggc ctt tca gac atc cca ggt    6471
Cys Glu Asn Gln Pro Met Leu Pro Ile Gly Leu Ser Asp Ile Pro Gly
            625                 630                 635 gaa gcc atg gtg aag ctc tac tgc ccc aag tgc atg gat gtg tac aca    6519
Glu Ala Met Val Lys Leu Tyr Cys Pro Lys Cys Met Asp Val Tyr Thr
        640                 645                 650 ccc aag tca tca aga cac cat cac acg gat ggc gcc tac ttc ggc act    6567
Pro Lys Ser Ser Arg His His His Thr Asp Gly Ala Tyr Phe Gly Thr
    655                 660                 665 ggt ttc cct cac atg ctc ttc atg gtg cat ccc gag tac cgg ccc aag    6615
Gly Phe Pro His Met Leu Phe Met Val His Pro Glu Tyr Arg Pro Lys
670                 675                 680 aga cct gcc aac cag ttt gtg ccc agg ctc tac ggt ttc aag atc cat    6663
Arg Pro Ala Asn Gln Phe Val Pro Arg Leu Tyr Gly Phe Lys Ile His
685                 690                 695                 700 gcg atg gcc tac cag ctg cag ctc caa gcc gcc agc aac ttc aag agc    6711
Ala Met Ala Tyr Gln Leu Gln Leu Gln Ala Ala Ser Asn Phe Lys Ser
            705                 710                 715 cca gtc aag acg att cgc taa gtcgacaaga aggagatata cat atg tcg gga    6764
Pro Val Lys Thr Ile Arg *                             Met Ser Gly
        720                                                   725 ccc gtg cca agc agg gcc aga gtt tac aca gat gtt aat aca cac aga    6812
Pro Val Pro Ser Arg Ala Arg Val Tyr Thr Asp Val Asn Thr His Arg
            730                 735                 740 cct cga gaa tac tgg gat tac gag tca cat gtg gtg gaa tgg gga aat    6860
Pro Arg Glu Tyr Trp Asp Tyr Glu Ser His Val Val Glu Trp Gly Asn
        745                 750                 755 caa gat gac tac cag ctg gtt cga aaa tta ggc cga ggt aaa tac agt    6908
Gln Asp Asp Tyr Gln Leu Val Arg Lys Leu Gly Arg Gly Lys Tyr Ser
    760                 765                 770 gaa gta ttt gaa gcc atc aac atc aca aat aat gaa aaa gtt gtt gtt    6956
Glu Val Phe Glu Ala Ile Asn Ile Thr Asn Asn Glu Lys Val Val Val
775                 780                 785 aaa att ctc aag cca gta aaa aag aag aaa att aag cgt gaa ata aag    7004
Lys Ile Leu Lys Pro Val Lys Lys Lys Lys Ile Lys Arg Glu Ile Lys
790                 795                 800                 805 att ttg gag aat ttg aga gga ggt ccc aac atc atc aca ctg gca gac    7052
Ile Leu Glu Asn Leu Arg Gly Gly Pro Asn Ile Ile Thr Leu Ala Asp
            810                 815                 820 att gta aaa gac cct gtg tca cga acc ccc gcc ttg gtt ttt gaa cac    7100
Ile Val Lys Asp Pro Val Ser Arg Thr Pro Ala Leu Val Phe Glu His
825                 830                 835
```

-continued

```
gta aac aac aca gac ttc aag caa ttg tac cag acg tta aca gac tat    7148
Val Asn Asn Thr Asp Phe Lys Gln Leu Tyr Gln Thr Leu Thr Asp Tyr
        840                 845                 850 gat att cga ttt tac atg tat gag att ctg aag gcc ctg gat tat tgt    7196
Asp Ile Arg Phe Tyr Met Tyr Glu Ile Leu Lys Ala Leu Asp Tyr Cys
855                 860                 865 cac agc atg gga att atg cac aga gat gtc aag ccc cat aat gtc atg    7244
His Ser Met Gly Ile Met His Arg Asp Val Lys Pro His Asn Val Met
870                 875                 880                 885 att gat cat gag cac aga aag cta cga cta ata gac tgg ggt ttg gct    7292
Ile Asp His Glu His Arg Lys Leu Arg Leu Ile Asp Trp Gly Leu Ala
        890                 895                 900 gag ttt tat cat cct ggc caa gaa tat aat gtc cga gtt gct tcc cga    7340
Glu Phe Tyr His Pro Gly Gln Glu Tyr Asn Val Arg Val Ala Ser Arg
        905                 910                 915 tac ttc aaa ggt cct gag cta ctt gta gac tat cag atg tac gat tat    7388
Tyr Phe Lys Gly Pro Glu Leu Leu Val Asp Tyr Gln Met Tyr Asp Tyr
        920                 925                 930 agt ttg gat atg tgg agt ttg ggt tgt atg ctg gca agt atg atc ttt    7436
Ser Leu Asp Met Trp Ser Leu Gly Cys Met Leu Ala Ser Met Ile Phe
935                 940                 945 cgg aag gag cca ttt ttc cat gga cat gac aat tat gat cag ttg gtg    7484
Arg Lys Glu Pro Phe Phe His Gly His Asp Asn Tyr Asp Gln Leu Val
950                 955                 960                 965 agg ata gcc aag gtt ctg ggg aca gaa gat tta tat gac tat att gac    7532
Arg Ile Ala Lys Val Leu Gly Thr Glu Asp Leu Tyr Asp Tyr Ile Asp
        970                 975                 980 aaa tac aac att gaa tta gat cca cgt ttc aat gat atc ttg ggc aga    7580
Lys Tyr Asn Ile Glu Leu Asp Pro Arg Phe Asn Asp Ile Leu Gly Arg
        985                 990                 995 cac tct cga aag cga tgg gaa cgc ttt gtc cac agt gaa aat cag cac    7628
His Ser Arg Lys Arg Trp Glu Arg Phe Val His Ser Glu Asn Gln His
        1000                1005                1010 ctt gtc agc cct gag gcc ttg gat ttc ctg gac aaa ctg ctg cga tat    7676
Leu Val Ser Pro Glu Ala Leu Asp Phe Leu Asp Lys Leu Leu Arg Tyr
        1015                1020                1025 gac cac cag tca cgg ctt act gca aga gag gca atg gag cac ccc tat    7724
Asp His Gln Ser Arg Leu Thr Ala Arg Glu Ala Met Glu His Pro Tyr
1030                1035                1040                1045 ttc tac act gtt gtg aag gac cag gct cga atg ggt tca tct agc atg    7772
Phe Tyr Thr Val Val Lys Asp Gln Ala Arg Met Gly Ser Ser Ser Met
                1050                1055                1060 cca ggg ggc agt acg ccc gtc agc agc gcc aat atg atg tca ggg att    7820
Pro Gly Gly Ser Thr Pro Val Ser Ser Ala Asn Met Met Ser Gly Ile
        1065                1070                1075 tct tca gtg cca acc cct tca ccc ctt gga cct ctg gca ggc tca cca    7868
Ser Ser Val Pro Thr Pro Ser Pro Leu Gly Pro Leu Ala Gly Ser Pro
        1080                1085                1090 gtg att gct gct gcc aac ccc ctt ggg atg cct gtt cca gct gcc gct    7916
Val Ile Ala Ala Ala Asn Pro Leu Gly Met Pro Val Pro Ala Ala Ala
        1095                1100                1105 ggc gct cag cag taa gctagcgtcg acggatccgg ctgctaacaa agcccgaaag    7971
Gly Ala Gln Gln *
1110 gaagctgagt tggctgctgc caccgctgag caataactag cataacccct tggggcctct    8031 aaacgggtct tgagggggttt tttgctgaaa ggaggaacta tatccggata tcccgcaaga    8091 ggcccggcag taccggcata accaagccta tgcctacagc atccagggtg acggtgccga    8151 ggatgacgat gagcgcattg ttagatttca tacacggtgc ctgactgcgt tagcaattta    8211
```

-continued

```
actgtgataa actaccgcat taaagcttat cgatcccgca agaggcccgg cagtaccggc    8271
ataaccaagc ctatgcctac agcatccagg gtgacggtgc cgaggatgac gatgagcgca    8331
ttgttagatt tcatacacgg tgcctgactg cgttagcaat ttaactgtga taaactaccg    8391
cattaaagct tatcgatgat aagctgtcaa acatgagaa                           8430
```

<210> SEQ ID NO 11
<211> LENGTH: 294
<212> TYPE: PRT
<213> ORGANISM: Homo sapiens

<400> SEQUENCE: 11

```
Met Gln Ile Thr Glu Lys Tyr Leu Pro Phe Gly Asn Trp Gln Thr Tyr
 1               5                  10                  15

Cys Arg Ile Val Gly Glu Ala Thr Asp Arg Ala Pro Leu Leu Leu Leu
            20                  25                  30

His Gly Gly Pro Gly Ser Ser His Asn Tyr Phe Glu Val Leu Asp Gln
        35                  40                  45

Val Ala Glu Lys Ser Gly Arg Gln Val Ile Met Tyr Asp Gln Leu Gly
    50                  55                  60

Cys Gly Asn Ser Ser Ile Pro Asp Asp Gln Ala Glu Thr Ala Tyr Thr
65                  70                  75                  80

Ala Gln Thr Trp Val Lys Glu Leu Glu Asn Val Arg Glu Gln Leu Gly
                85                  90                  95

Leu Asp Gln Ile His Leu Leu Gly Gln Ser Trp Gly Gly Met Leu Ala
            100                 105                 110

Leu Ile Tyr Leu Cys Asp Tyr Gln Pro Lys Gly Val Lys Ser Leu Ile
        115                 120                 125

Leu Ser Ser Thr Leu Ala Ser Ala Lys Leu Trp Ser Gln Glu Leu His
    130                 135                 140

Arg Leu Ile Lys Tyr Leu Pro Lys Gly Glu Gln Ala Ala Ile Lys Glu
145                 150                 155                 160

Ala Glu Thr Thr Gly Asn Tyr Asp Ser Pro Ala Tyr Gln Ala Ala Asn
                165                 170                 175

Ala His Phe Met Asp Gln His Ala Ile Lys Leu Thr Pro Asp Leu Pro
            180                 185                 190

Glu Pro Val Leu Arg Lys Lys Gly Gly Asn Leu Ala Tyr Leu Thr
        195                 200                 205

Gly Trp Gly Pro Asn Glu Tyr Thr Pro Ile Gly Asn Leu His Gly Tyr
    210                 215                 220

Glu Tyr Thr Asp Arg Leu Lys Asp Leu Asp Leu Pro Ala Leu Ile Thr
225                 230                 235                 240

Ser Gly Thr Asp Asp Leu Cys Thr Pro Leu Val Ala Lys Ser Met Tyr
                245                 250                 255

Asp His Leu Pro Asn Ala Arg Trp Glu Leu Phe Ala Gly Cys Gly His
            260                 265                 270

Met Pro Phe Val Gln Glu Asn Ala Lys Tyr Gln Glu Leu Leu Ser Asp
        275                 280                 285

Trp Leu Ile Ser Gln Asp
    290
```

<210> SEQ ID NO 12
<211> LENGTH: 213
<212> TYPE: PRT
<213> ORGANISM: Homo sapiens

```
<400> SEQUENCE: 12

Met Pro Arg Glu Thr Ile Glu Ser Leu Ser Ser Glu Glu Ser Ile
 1               5                  10                  15

Thr Glu Tyr Lys Gln Lys Val Glu Lys Val Lys His Glu Asp Gln Gln
             20                  25                  30

Gln Gly Glu Asp Glu His Gln Asp Lys Ile Tyr Pro Ser Phe Gln Pro
         35                  40                  45

Gln Pro Leu Ile Tyr Pro Phe Val Glu Pro Ile Pro Tyr Gly Phe Leu
     50                  55                  60

Pro Gln Asn Ile Leu Pro Leu Ala Gln Pro Ala Val Val Leu Pro Val
 65                  70                  75                  80

Pro Gln Pro Glu Ile Met Glu Val Pro Lys Ala Lys Asp Thr Val Tyr
                 85                  90                  95

Thr Lys Gly Arg Val Met Pro Val Leu Lys Ser Pro Thr Ile Pro Phe
            100                 105                 110

Phe Asp Pro Gln Ile Pro Lys Leu Thr Asp Leu Glu Asn Leu His Leu
        115                 120                 125

Pro Leu Pro Leu Leu Gln Pro Leu Met Gln Gln Val Pro Gln Pro Ile
130                 135                 140

Pro Gln Thr Leu Ala Leu Pro Pro Gln Pro Leu Trp Ser Val Pro Gln
145                 150                 155                 160

Pro Lys Val Leu Pro Ile Pro Gln Gln Val Val Pro Tyr Pro Gln Arg
                165                 170                 175

Ala Val Pro Val Gln Ala Leu Leu Asn Gln Glu Leu Leu Leu Asn
            180                 185                 190

Pro Thr His Gln Ile Tyr Pro Val Thr Gln Pro Leu Ala Pro Val His
        195                 200                 205

Asn Pro Ile Ser Val
    210

<210> SEQ ID NO 13
<211> LENGTH: 215
<212> TYPE: PRT
<213> ORGANISM: Homo sapiens

<400> SEQUENCE: 13

Met Ser Ser Ser Glu Glu Val Ser Trp Ile Ser Trp Phe Cys Gly Leu
 1               5                  10                  15

Arg Gly Asn Glu Phe Phe Cys Glu Val Asp Glu Asp Tyr Ile Gln Asp
             20                  25                  30

Lys Phe Asn Leu Thr Gly Leu Asn Glu Gln Val Pro His Tyr Arg Gln
         35                  40                  45

Ala Leu Asp Met Ile Leu Asp Leu Glu Pro Asp Glu Glu Leu Glu Asp
     50                  55                  60

Asn Pro Asn Gln Ser Asp Leu Ile Glu Gln Ala Ala Glu Met Leu Tyr
 65                  70                  75                  80

Gly Leu Ile His Ala Arg Tyr Ile Leu Thr Asn Arg Gly Ile Ala Gln
                 85                  90                  95

Met Leu Glu Lys Tyr Gln Gln Gly Asp Phe Gly Tyr Cys Pro Arg Val
            100                 105                 110

Tyr Cys Glu Asn Gln Pro Met Leu Pro Ile Gly Leu Ser Asp Ile Pro
        115                 120                 125

Gly Glu Ala Met Val Lys Leu Tyr Cys Pro Lys Cys Met Asp Val Tyr
130                 135                 140
```

```
Thr Pro Lys Ser Ser Arg His His His Thr Asp Gly Ala Tyr Phe Gly
145                 150                 155                 160

Thr Gly Phe Pro His Met Leu Phe Met Val His Pro Glu Tyr Arg Pro
            165                 170                 175

Lys Arg Pro Ala Asn Gln Phe Val Pro Arg Leu Tyr Gly Phe Lys Ile
            180                 185                 190

His Ala Met Ala Tyr Gln Leu Gln Leu Gln Ala Ala Ser Asn Phe Lys
            195                 200                 205

Ser Pro Val Lys Thr Ile Arg
    210                 215

<210> SEQ ID NO 14
<211> LENGTH: 391
<212> TYPE: PRT
<213> ORGANISM: Homo sapiens

<400> SEQUENCE: 14

Met Ser Gly Pro Val Pro Ser Arg Ala Arg Val Tyr Thr Asp Val Asn
1               5                   10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
            35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
            165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
            195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
            245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
    290                 295                 300
```

```
Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
            325                 330                 335

Ser Ser Met Pro Gly Gly Ser Thr Pro Val Ser Ser Ala Asn Met Met
        340                 345                 350

Ser Gly Ile Ser Ser Val Pro Thr Pro Ser Pro Leu Gly Pro Leu Ala
        355                 360                 365

Gly Ser Pro Val Ile Ala Ala Ala Asn Pro Leu Gly Met Pro Val Pro
    370                 375                 380

Ala Ala Ala Gly Ala Gln Gln
385                 390
```

<210> SEQ ID NO 15
<211> LENGTH: 41
<212> TYPE: DNA
<213> ORGANISM: Artificial Sequence
<220> FEATURE:
<223> OTHER INFORMATION: Primer RO190

<400> SEQUENCE: 15
ggagatatac tatgcchcgt gaaaccatcg aatccctgag c                          41

<210> SEQ ID NO 16
<211> LENGTH: 19
<212> TYPE: DNA
<213> ORGANISM: Artificial Sequence
<220> FEATURE:
<223> OTHER INFORMATION: Primer RO74

<400> SEQUENCE: 16
gctagttatt gctcagcgg                                                   19

<210> SEQ ID NO 17
<211> LENGTH: 31
<212> TYPE: DNA
<213> ORGANISM: Artificial Sequence
<220> FEATURE:
<223> OTHER INFORMATION: Primer RO204

<400> SEQUENCE: 17
gcatttatca ggagtactgt ctcatgagcg g                                     31

<210> SEQ ID NO 18
<211> LENGTH: 21
<212> TYPE: DNA
<213> ORGANISM: Artificial Sequence
<220> FEATURE:
<223> OTHER INFORMATION: Primer RO221

<400> SEQUENCE: 18
cgacatcata acagtactgg c                                                21

<210> SEQ ID NO 19
<211> LENGTH: 35
<212> TYPE: DNA
<213> ORGANISM: Artificial Sequence
<220> FEATURE:
<223> OTHER INFORMATION: Primer RO117

<400> SEQUENCE: 19
tcagaggaat tcaagatgca aatcacagaa aaata                                 35

```
<210> SEQ ID NO 20
<211> LENGTH: 35
<212> TYPE: DNA
<213> ORGANISM: Artificial Sequence
<220> FEATURE:
<223> OTHER INFORMATION: Primer RO118

<400> SEQUENCE: 20
gtgtccgtcg acctagtcct ggctgattaa ccagt                            35

<210> SEQ ID NO 21
<211> LENGTH: 31
<212> TYPE: DNA
<213> ORGANISM: Artificial Sequence
<220> FEATURE:
<223> OTHER INFORMATION: Primer RO77

<400> SEQUENCE: 21
tatgccgcgt gaaccatcga atccctgagc t                                31

<210> SEQ ID NO 22
<211> LENGTH: 26
<212> TYPE: DNA
<213> ORGANISM: Artificial Sequence
<220> FEATURE:
<223> OTHER INFORMATION: Primer RO78

<400> SEQUENCE: 22
cagggattcg atggtttcac gcggca                                      26
```